US010119115B2

(12) United States Patent
Blaschek et al.

(10) Patent No.: US 10,119,115 B2
(45) Date of Patent: Nov. 6, 2018

(54) METHODS AND COMPOSITIONS FOR PRODUCING SOLVENTS

(71) Applicants: The Board of Trustees of the University of Illinois, Urbana, IL (US); Eastman Renewable Materials, LLC, Kingsport, TN (US)

(72) Inventors: Hans P. Blaschek, Champaign, IL (US); Steven F. Stoddard, Cerro Gordo, IL (US); Zhen Shi, Champaign, IL (US)

(73) Assignees: The Board of Trustees of the University of Illinois, Urbana, IL (US); Eastman Renewable Materials, LLC, Kingsport, TN (US)

( * ) Notice: Subject to any disclaimer, the term of this patent is extended or adjusted under 35 U.S.C. 154(b) by 0 days.

(21) Appl. No.: 14/796,253

(22) Filed: Jul. 10, 2015

(65) Prior Publication Data

US 2016/0068802 A1 Mar. 10, 2016

Related U.S. Application Data

(62) Division of application No. 12/154,027, filed on May 19, 2008, now Pat. No. 9,080,187.

(60) Provisional application No. 60/930,775, filed on May 17, 2007.

(51) Int. Cl.

| | |
|---|---|
| ***C12P 7/16*** | (2006.01) |
| ***C12N 1/20*** | (2006.01) |
| ***C12N 1/14*** | (2006.01) |
| ***C12N 1/19*** | (2006.01) |
| ***C12N 9/04*** | (2006.01) |
| ***C12N 9/02*** | (2006.01) |
| ***C12N 9/12*** | (2006.01) |
| ***C12P 7/06*** | (2006.01) |
| ***C12P 7/28*** | (2006.01) |
| ***C12N 15/70*** | (2006.01) |
| ***C12R 1/145*** | (2006.01) |

(52) U.S. Cl.

CPC ............... *C12N 1/20* (2013.01); *C12N 9/001* (2013.01); *C12N 9/0006* (2013.01); *C12N 9/1217* (2013.01); *C12N 15/70* (2013.01); *C12P 7/065* (2013.01); *C12P 7/16* (2013.01); *C12P 7/28* (2013.01); *C12R 1/145* (2013.01); *C12Y 101/01001* (2013.01); *Y02E 50/10* (2013.01); *Y02E 50/17* (2013.01)

(58) Field of Classification Search

None

See application file for complete search history.

(56) References Cited

U.S. PATENT DOCUMENTS

| | | | |
|---|---|---|---|
| 6,358,717 | B1 | 3/2002 | Blaschek et al. |
| 6,372,457 | B1 | 4/2002 | Berry et al. |
| 6,884,614 | B1 | 4/2005 | Pompejus et al. |
| 6,960,465 | B1 | 11/2005 | Papoutsakis et al. |
| 6,962,794 | B2 | 11/2005 | Valle et al. |
| 7,226,761 | B2 | 6/2007 | Miasnikov et al. |
| 7,332,304 | B2 | 2/2008 | Deng et al. |
| 7,381,548 | B2 | 6/2008 | Sheremet'eva et al. |
| 7,524,660 | B2 | 4/2009 | Caimi et al. |
| 8,124,381 | B2 | 2/2012 | Deng et al. |
| 8,236,525 | B2 | 8/2012 | San et al. |
| 8,389,214 | B2 | 3/2013 | Cervin et al. |
| 2005/0089979 | A1 | 4/2005 | Ezeji et al. |
| 2006/0292674 | A1 | 12/2006 | Pompejus et al. |
| 2007/0118916 | A1 | 5/2007 | Puzio et al. |
| 2008/0182308 | A1 | 7/2008 | Donaldson et al. |
| 2009/0111154 | A1 | 4/2009 | Liao et al. |
| 2009/0155869 | A1 | 6/2009 | Buelter et al. |
| 2009/0275097 | A1 | 11/2009 | Sun et al. |

FOREIGN PATENT DOCUMENTS

| | | | | |
|---|---|---|---|---|
| WO | 06/007530 A2 | 1/2006 | | |
| WO | WO-2007041269 A2 * | 4/2007 | ........... C12N 9/0004 | |
| WO | 08/080124 A2 | 7/2008 | | |
| WO | 08/131286 A1 | 10/2008 | | |
| WO | 08/143704 A2 | 11/2008 | | |
| WO | 08/144060 A2 | 11/2008 | | |
| WO | 09/036076 A1 | 3/2009 | | |

OTHER PUBLICATIONS

Sang, H., Mechanisms of Development 121:1179-1186, 2004 (Year: 2004).*

GenBank Accession No. NC_009617, Jun. 2007, 2 pages (Year: 2007).*

Mermelstein et al., Biotechnol. Bioengineer. 42:1053-1060, 1993 (Year: 1993).*

Wilkinson et al., J. Bacteriol. 177:439-448, 1995 (Year: 1995).*

Harris et al., "Characterization of Recombinant Strains of the Clostridium acetobutylicum Butyrate Kinase Inactivation Mutant: Need for New Phenomenological Models?", Biotechnol. Bioengineer. 67:1-11, 2000 (Year: 2000).*

Desai et al., "Antisense RNA Strategies for Metabolic Engineering of Clostridium acetobutylicum", Appl. Environ. Microbiol. 65:936-945, 1999 (Year: 1999).*

(Continued)

*Primary Examiner* — David Steadman

(74) *Attorney, Agent, or Firm* — McDonell Boehnen Hulbert & Berghoff LLP

(57) ABSTRACT

Described herein are methods, compositions and synthetic biology approaches for solvent production, including but not limited to butanol production. Described herein are recombinant bacteria and yeast strains which may be used in production of a solvent, including but not limited to butanol, from lignocellulosic and other plant-based feedstocks. Described herein are methods of producing solvents, including but not limited to butanol, using bacteria and yeast strains. Described herein are methods of producing organisms that display highly efficient butanol production.

16 Claims, 24 Drawing Sheets

Specification includes a Sequence Listing.

(56) References Cited

OTHER PUBLICATIONS

Peretz et al., "Molecular Cloning, Nucleotide Sequencing, and Expression of Genes Encoding Alcohol Dehydrogenases From the Thermophile thermoanaerobacter brockii and the Mesophile Clostridium beijerinckii", Anaerobe, 3(4):259-270 (1997)*.
Bogin et al., "Enhanced thermal stability of Clostridium beijerinckii alcohol dehydrogenase after strategic substitution of amino acid residues with prolines from homolgous thermophilic Thermoanaerobacter brockii alcohol dehydrogenase", Protein Science, 7(5):1156-1163 (1998)*.
Bogin et al., "Structural basis for the enhanced thermal stability of alcohol dehydrogenase mutants from the mesophilic bacterium Clostridium beijerinckii: contribution of salt bridging", Protein Science, 11(11):2561-2574 (2002)*.
Goihberg et al., "A Single Proline Substitution is Critical for the Thermostabilization of Clostridium beijerinckii Alcohol Dehydrogenase", Proteins: Structure, Function and Bioinformatics, 66(1):196-204 (2007)*.
Peretz et al., "Thermal stability and enzymatic activity of subunit hybrids of tetrameric alcohol dehydrogenases from the extreme thermophile Thermoanaerobacter brockii and the mesophile Clostridium beijerinckii", FEBS Journal, 272 (Supplement 1):385 (abstract G2-094P) (2005)*.
Ismaiel et al., "Purification and Characterization of a Primary-Secondary Alcohol Dehydrogenase from Two Strains of Clostridium beijerinckii", Journal of Bacteriology, 175(16):5097-5105 (1993)*.
GenBank Accession No. AY616585, dated May 4, 2004*.
Chen, "Alcohol dehydrogenase: multiplicity and relatedness in the solvent-producing clostridia", FEMS Microbiology Reviews, 17:263-273 (1995)*.
Toth et al., "The ald gene, encoding a coenzyme A-acylating aldehyde dehydrogenase, distinguishes Clostridium beijerinckii and two other solvent-producing clostridia from Clostridium acetobutylicum", Applied and Environmental Microbiology, 65(11):4973-4980 (1999)*.
Tummala et al., "Antisense RNA downregulation of coenzyme A transferase combined with alcohol-aldehyde dehydrogenase overexpression leads to predominantly alcohologenic Clostridium acetobutylicum fermentations", Journal of Bacteriology,185(12):3644-53 (2003)*.
Walter et al., "Studies of recombinant Clostridium acetobutylicum with increased dosages of butyrate formation genes", Ann N Y Acad Sci., 721:69-72 (1994)*.
Yan et al., "Coenzyme A-acylating aldehyde dehydrogenase from Clostridium beijerinckii NRRL B592", Appl Environ Microbiol., 56(9):2591-9 (1990)*.
Alasker et al., "Transcriptional analysis of spo0A overexpression in Clostridium acetobutylicum and its effect on the cell's response to butanol stress", J Bacteriol., 186(7):1959-71 (2004)*.
Fontaine, et al., "Molecular characterization and transcriptional analysis of adhE2, the gene encoding the NADH-dependent aldehyde/ alcohol dehydrogenase responsible for butanol production in alcohologenic cultures of Clostridium acetobutylicum ATCC 824", J Bacteriol., 184(3):821-30 (2002)*.
Lee et al., "Glucose uptake in Clostridium beijerinckii NCIMB 8052 and the solvent-hyperproducing mutant BA101", Appl Environ Microbiol., 67(11):5025-31 (2001)*.
Tomas et al., "DNA array-based transcriptional analysis of asporogenous, nonsolventogenic Clostridium acetobutylicum strains SKO1 and M5", J Bacteriol.,185(15):4539-47, (2003)*.
Tummala et al., "Transcriptional analysis of product-concentration driven changes in cellular programs of recombinant Clostridium acetobutylicumstrains", Biotechnol Bioeng., 84(7):842-54 (2003)*.
Woods, "The genetic engineering of microbial solvent production", Trends Biotechnol., 13(7):259-64 (1995)*.
Youngleson et al., "Cloning and Expression of a Clostridium acetobutylicum Alcohol Dehydrogenase Gene in *Escherichia coli*", Appl Environ Microbiol., 54(3):676-682 (1988)*.
Alasker et al., "Transcriptional program of early sporulation and stationary-phase events in Clostridium acetobutylicum" J Bacteriol., 187(20):7103-7118 (2005)*.
Boynton et al., "Cloning, sequencing, and expression of clustered genes encoding beta-hydroxybutyryl-coenzyme A (CoA) dehydrogenase, crotonase, and butyryl-CoA dehydrogenase from Clostridium acetobutylicum ATCC 824", J Bacteriol., 178(11):3015-3024 (1996)*.
Broda et al., "*Clostridium algidixylanolyticum* sp. nov., a psychrotolerant, xylan-degrading, spore-forming bacterium", Int J Syst Evol Microbiol., 50 Pt 2:623-31 (2000)*.
Ezeji et al., "Acetone butanol ethanol (ABE) production from concentrated substrate: reduction in substrate inhibition by fed-batch technique and product inhibition by gas stripping", Appl Microbiol Biotechnol., 63(6):653-8 (2004)*.
Ezeji et al., "Butanol fermentation research: upstream and downstream manipulations", Chem Rec. 2004;4(5):305-14 (2004)*.
Fromanek et al., "Enhanced Butanol Production by Clostridium beijerinckii BA101 Grown in Semidefined P2 Medium Containing 6 Percent Maltodextrin or Glucose", Appl Environ Microbiol., 63(6):2306-10 (1997)*.
Green et al., "Genetic manipulation of acid and solvent formation in clostridium acetobutylicum ATCC 824", Biotechnol Bioeng., 58(2-3):215-21 (1998)*.
Jones et al., "The transcriptional program underlying the physiology of clostridial sporulation", Genome Biol., 9(7): R114. doi: 10.1186/ gb-2008-9-7-r114 (2008)*.
Jones et al., "Acetone-butanol fermentation revisited", Microbiol Rev., 50(4):484-524 (1986)*.
Peterson et al., "Cloning of the Clostridium acetobutylicum ATCC 824 acetyl coenzyme A acetyltransferase (thiolase; EC 2.3.1.9) gene", Appl Environ Microbiol., 57(9):2735-41 (1991)*.
Peterson et al., "Molecular cloning of an alcohol (butanol) dehydrogenase gene cluster from Clostridium acetobutylicum ATCC 824", J Bacteriol., 173(5):1831-4 (1991)*.
Querishi et al., "Butanol production using Clostridium beijerinckii BA101 hyper-butanol producing mutant strain and recovery by pervaporation", Appl Biochem Biotechnol., 84-86:225-3 (2000)*.
Shi et al., "Transcriptional analysis of Clostridium beijerinckii NCIMB 8052 and the hyper-butanol-producing mutant BA101 during the shift from acidogenesis to solventogenesis", Appl Environ Microbiol., 74(24):7709-14. doi: 10.1128/ AEM.01948-08 (2008).
Erni, B., et al., "The mannose permease of *Escherichia coli* consists of three different proteins. Amino acid sequence and function in sugar transport, sugar phosphorylation, and penetration of phage lambda DNA", The Journal of Biological Chemistry, vol. 262, No. 11, pp. 5238-45237 (1987)*.
Saier, M. H., et al., "Energetics of the bacterial phosphotransferase system in sugar transport and the regulation of carbon metabolism", In: Bacteria: A Treatise on Structure and Function, Gunslaus et al., Eds., pp. 273-299 (1990)*.
Snoep, J. L., et al., "Reconstruction of glucose uptake and phosphorylation in a glucose-negative mutant of *Escherichia coli* by using *Zymomonas mobilis* genes encoding the glucose facilitator protein and glucokinase," Journal of Bacteriology, vol. 176, No. 7, pp. 2133-2135 (1994)*.
Flores N. et al., "Pathway engineering for the production of aromatic compounds in *Escherichia coli*", Nature Biotechnology, vol. 14, pp. 620-623 (1996)*.
Siebold, C., et al., "Carbohydrate transporters of the bacterial phosphoenolpyruvate:sugar phosphotransferase system (PTS)", FEBS Letters, vol. 504, pp. 104-111 (2001)*.
Flores, S., et al., "Analysis of carbon metabolism in *Escherichia coli* strains with an inactive phosphotransferase system by 13C labeling and NMR spectroscopy", Metabolic Engineering, vol. 4, pp. 124-137 (2002)*.
Hernandez-Montalvo, V,. et al., "Expression of gaiP and glk in a *Escherichia coli* PTS mutant restores glucose transport and increases glycolytic flux to fermentation products", Biotechnology and Bioengineering, vol. 83, No. 6, pp. 687-694 (2003)*.
Deutscher, J., et al., "Loss of protein kinase catalyzed phosphorylation of HPr, a phosphocarrier protein of the phosphotransferase system , by mutation of the ptsH gene confers catabolite repression resistance to several catabolic genes of *Bacillus subtilis*", Journal of Bacteriology, vol. 176, No. 11 , pp. 3336-3344 (1994)*.

(56) References Cited

OTHER PUBLICATIONS

Picon, A., et al., "Reducing the glucose uptake rate in *Escherichia coli* affects growth rate but not protein production", Biotechnology and Bioengineering, vol. 90, No. 2, pp. 191-200 (2005)*.

Yu, Y., et al., "Analysis of the mechanism and regulation of lactose transport and metabolism in Clostridium acetobutylicum ATCC 824", Applied and Environmental Microbiology, vol. 73, No. 6, pp. 1842-1850 (2007)*.

Gaigalat, L. , et al., "The DeoR-type transcriptional regulator SugR acts as a repressor for genes encoding the phosphoenolpyruvate:sugar phosphotransferase system (PTS) in Corynebacterium glutamicum", BMC Molecular Biology, vol. 8, pp. 104-104 (2007)*.

Guillaume, C., et al., "Molecular basis of fructose utilization by the wine yeast *Saccharomyces cerevisiae*: A mutated HXT3 allele enhances fructose fermentation", Applied and Environmental Microbiology, vol. 73, No. 8, pp. 2432-2439 (2007)*.

Joergensen, T. R., et al., "Glucose uptake and growth of glucose-limited chemostat cultures of Aspergillus niger and a disruptant lacking MstA, a high-affinity glucose transporter", Microbiology, vol. 153, No. 6, pp. 1963-1973 (2007)*.

Saloheimo, A., et al., "Xylose transport studies with xylose-utilizing *Saccharomyces cerevisiae* strains expressing heterologous and homologous permeases", Applied Microbiology and Biotechnology, vol. 74, No. 5, pp. 1041-1052 (2007)*.

Picon, A., et al., "Protein production by *Escherichia coli* wild-type and .deltal.ptsG mutant strains with IPTG induction and the onset", Journal of Industrial Microbiology and Biotechnology, vol. 35, pp. 213-218 (2008)*.

Barabote et al. , Comparative genomic analyses of the bacterial phosphotransferase system, Microbial Mol Bioi Rev. 69(4):608-34 (2005)*.

Lee et al., Evidence for the presence of an alternative glucose transport system in Clostridium beijerinckii NCIMB 8052 and the solvent hyperproducing mutant BA 101, Appl Environ Microbial. 71 (6):3384-7 (2005)*.

Shi et al., "Large number of phosphotransferase genes in the Clostridium beijernickii NCIMB 8052 genome and the study of their evolution", BMC Bioinformatics; 11(59):2-8 (2010)*.

Durre, "New insights and novel developments in clostridial acetone/butanol/isopropanol fermentation", Appl. Microbiol. Biotechnol., 49:639-648 (1998)*.

* cited by examiner

FIG. 1. Growth curves (A) and pH profiles (B) for the fermentor cultures of *C. beijerinckii* NCIMB 8052 (◆) and BA101 (o).
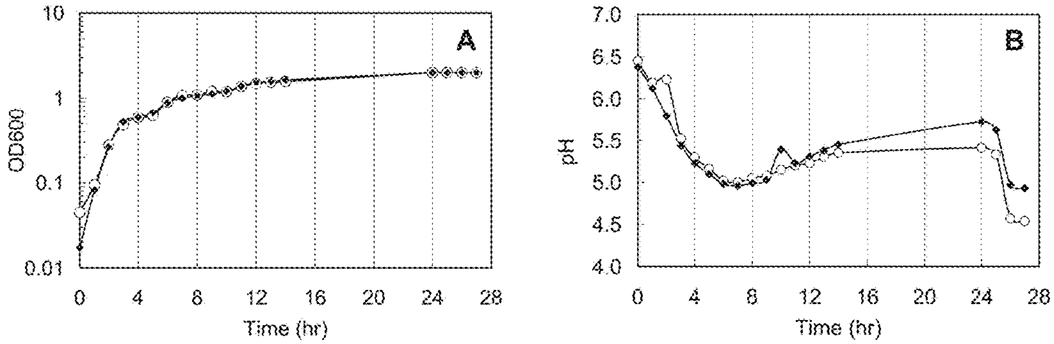

FIG. 2. Product formation in the fermentor cultures of *C. beijerinckii* NCIMB 8052 (♦) and BA101 (o).
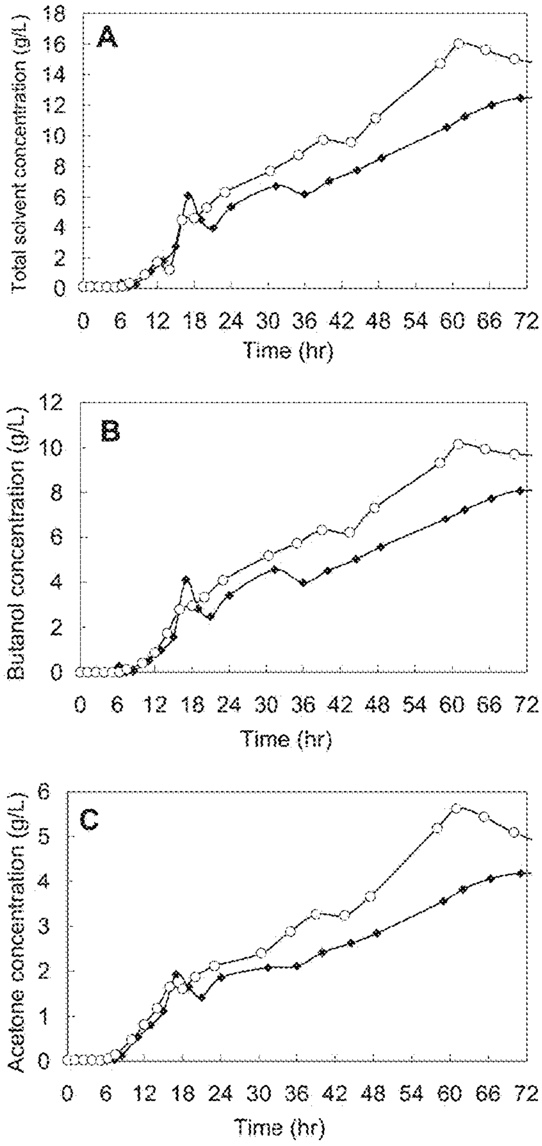

FIG. 3. Gene expression profiles analyzed by DNA microarray for *C. beijerinckii* NCIMB 8052 (A) and BA101 (B) over the time course of fermentation.
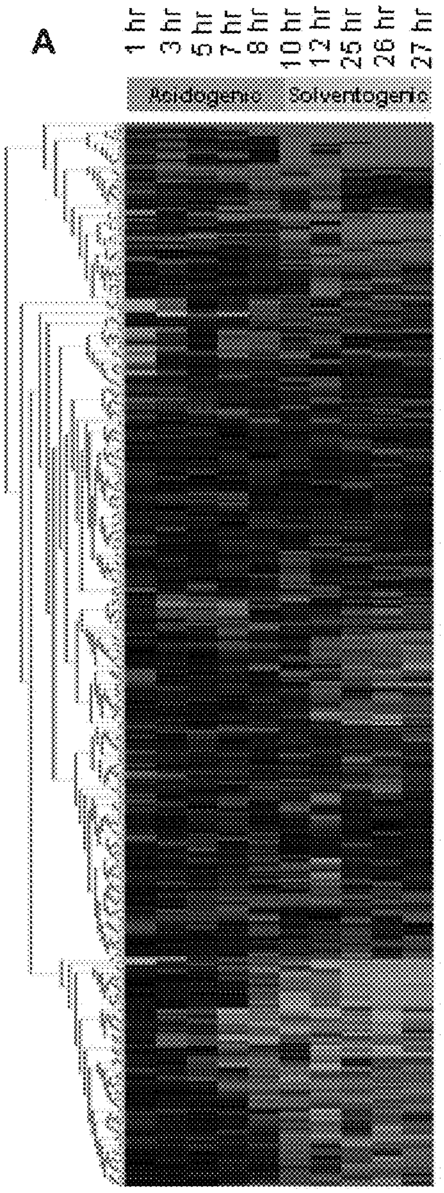

FIG. 4. Differential expression of solventogenic genes in *C. beijerinckii* NCIMB 8052 (♦) and BA101 (o).
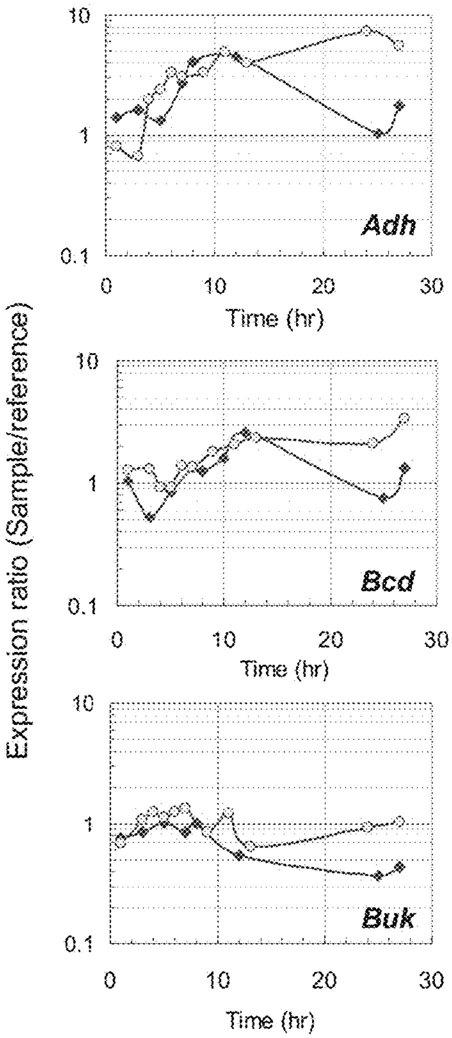

FIG. 5. Differential expression of sugar transporters in *C. beijerinckii* NCIMB 8052 (◆) and BA101 (o).
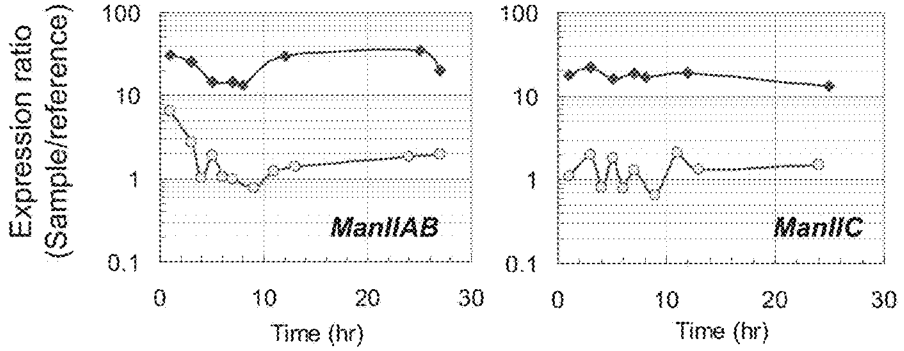

FIG. 6. Differential expression of sporulation genes in *C. beijerinckii* NCIMB 8052 (♦) and BA101 (o).
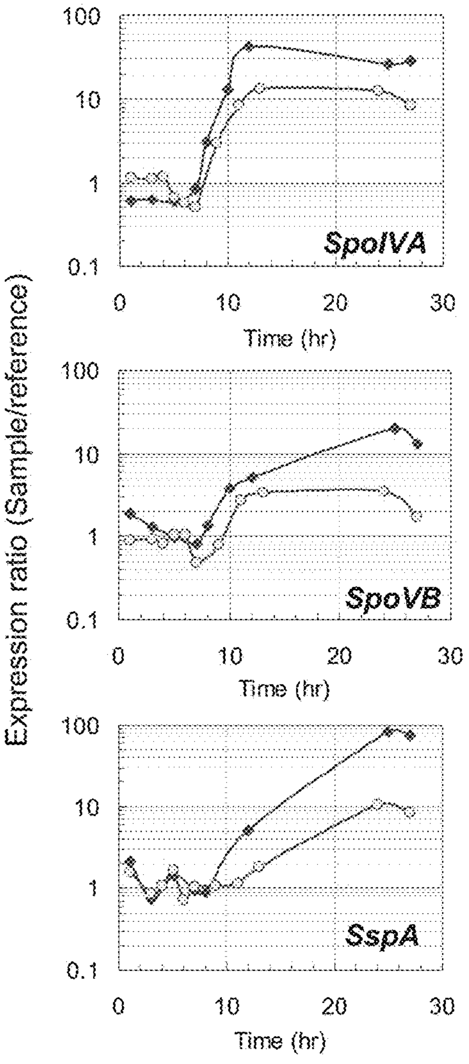

FIG. 7. Differential expression of chemotaxis genes in *C. beijerinckii* NCIMB 8052 (◆) and BA101 (o).
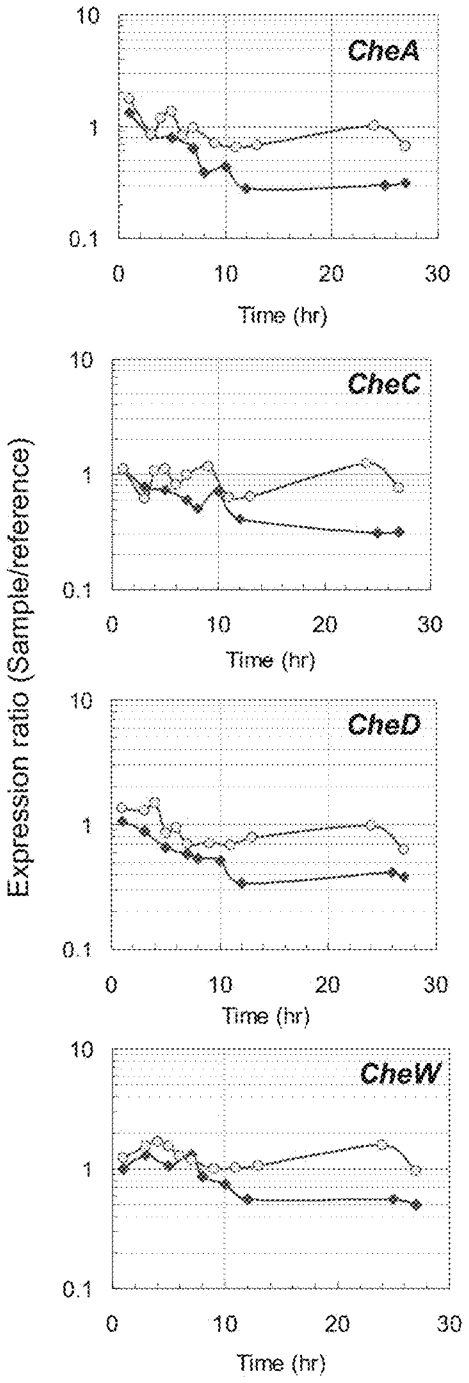

FIG. 8. Solventogenic genes with comparable expression kinetics in *C. beijerinckii* NCIMB 8052 (◆) and BA101 (o).
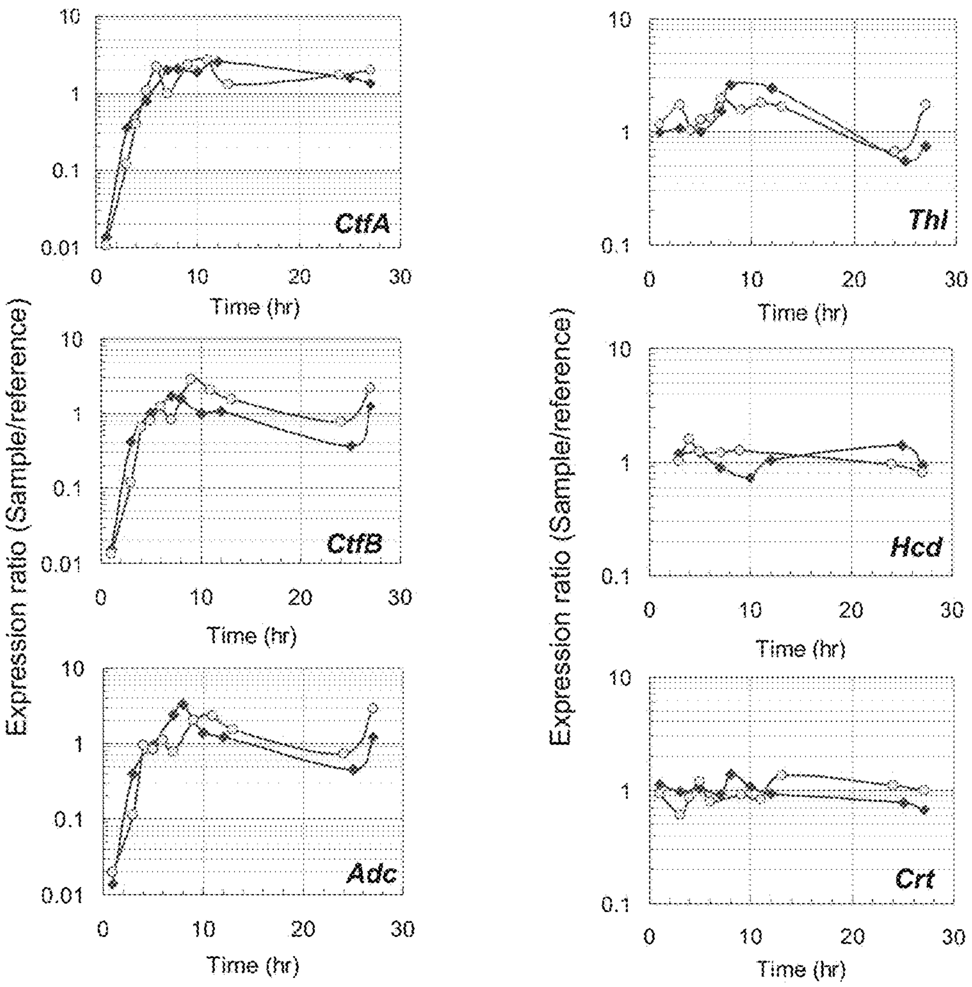

FIG. 9. Reactions in the clostridial solventogenic pathway.
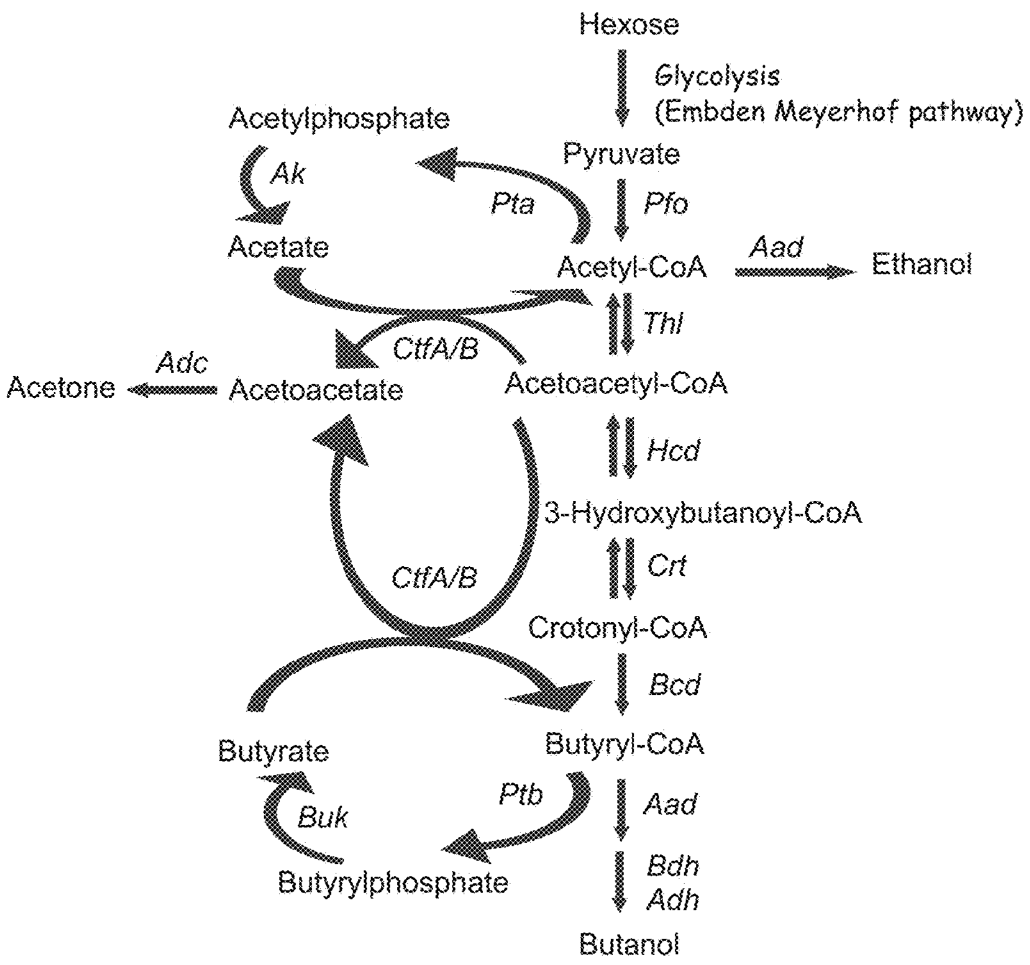

**FIG. 10. Adh (Alcohol dehydrogenase) *C. beijerinckii* NCIMB 8052 DNA sequence** atggcacgttttactttaccaagagacatttatcatggagaaggagcacttgaggcactt
aaaactttaaaaggtaagaaagctttcttagtagttggtggcggatcaatgaaaagattt
ggatttcttaaacaagttgaagattatttaaaagaagcaggaatggaagtagaattattt
gaaggtgttgaaccagatccatcagtggaaacagtaatgaaaggcgcagaagctatgaga
aactttgagcctgattggatagttgcaatgggtggaggatcaccaattgatgctgcaaag
gctatgtggatattctacgaatacccagattttacttttgaacaagcagttgttccattt
ggattaccagaccttagacaaaaagctaagtttgtagctattccatcaacaagcggtaca
gctacagaagttacagcattctcagttatcacaaattattcagaaaaattaaatatcct
ttagctgattttaacataactccagatatagcaatagttgatccagcacttgctcaaact
atgccaaaaactttaacagctcatactggaatggatgcattaactcacgctatagaagca
tacactgcatcacttcaatcaaatttctcagatccattagcaattaaagctgtagaaatg
gttcaagaaaatttaatcaaatcatttgaaggagataaagaagctagaaatctaatgcat
gaagctcaatgtttagctggaatggcattttctaatgcattacttggaatagttcactca
atggctcataaggttggtgctgtattccatattcctcatggatgtgcaaatgctatattt
ttaccatatgtaattgagtataacagaacaaaatgcgaaaatagatatggagatattgcg
agagccttaaaattaaaggaaacaatgatgccgagttaactgattcattaattgaatta
attaatggattaaatgataagttagagattcctcactcaatgaaagagtatggagttact
gaagaagattttaaagctaatctttcatttatcgctcataacgcagtattagatgcatgc
acaggatcaaatcctagagaaatagatgatgctacaatggaaaaattatttgaatgcaca
tactatggaactaaagttaatttgtaa
(SEQ ID NO: 1)

**FIG. 11. Bcd (Butyryl-CoA dehydrogenase) *C. beijerinckii* NCIMB 8052 DNA sequence**

```
atgaattttaagttaactagagaacaacaattagtacaacaaatggttagagaattcgca
gtaaatgaagttaagccaatagctgccgaaatcgacgaaacagaaagattccctatggaa
aacgttgaaaaaatggctaagcttaaaatgatggggatcccattttttaaagaatttggt
ggagcaggcggagatgttctttcatatataattgctgtggaagaattatcaaaagtttgt
ggtactacaggagttattctttcagcgcatacatcattatgtgcatcagtaattaatgaa
aatggaactaacgaacaaagagcaaaatatttacctgatctttgcagcggtaaaaagatc
ggtgctttcggattaacagaaccaggtgctggtacagatgctgcaggacaacaaacaact
gctgtattagaaggggaccattatgtattaaatggttcaaaaatcttcataacaaatggt
ggagttgctgaaactttcataatatttgctatgacagataagagtcaaggaacaaaagga
atttctgcattcatagtagaaaagttattcccaggattctcaataggaaaattagaaaac
aagatgggaatcagagcatcttcaactactgagttagttatggaaaactgcatagtacca
aaagaaaacctacttagcaaagaaggtaagggatttggtatagcaatgaaaactcttgat
ggaggaagaattggtatagctgctcaagctttaggtattgcagaaggagcttttgaagaa
gctgttaactatatgaaagaaagaaaacaatttggtaaaccattatcagcattccaagga
ttacaatggtatatagctgaaatggatgttaaaatccaagctgctaaatacttagtatac
ctagctgcaacaaagaagcaagctggtgagccttactcagtggatgctgcaagagctaaa
ttatttgctgcagatgttgcaatggaagttacaactaaggcagttcaaatctttggtgga
tatggttacactaaagaatacccagtagaaagaatgatgagagatgctaaaatatgcgaa
atctacgaaggaacttcagaagttcaaaagatggttatcgcaggaagcattttaagatag
(SEQ ID NO: 2)
```

**FIG. 12. Buk (Butyrate kinase) *C. beijerinckii* NCIMB 8052 DNA sequence** atgtcatataagctattaataatcaatccaggttcaacatcaacaaagattggtgtttac
gaaggagaaaaggaactatttgaagaaactttgagacacacaaatgaagaaataaagaga
tatgatacaatatatgatcaatttgaatttagaaaagaagttatattaaatgttcttaaa
gaaaagaattttgatataaagactctaagtgctattgttggtagaggtggaatgcttaga
ccagttgaaggtggaacatatgcagtaaatgatgcaatggttgaagatttaaaagttgga
gttcaaggacctcatgcttctaaccttggcggaataattgccaagtcaattggagatgaa
ttaaatattccatcatttatagtagatccagttgttacagatgagttagcagatgtagca
agactatctggagtaccagaactaccaagaaaaagtaaattccatgctttaatcaaaaa
gcggtagctaaaagatatggaaaagaaagtggacaaggatatgaaaacctaaatcttgta
gttgtacatatgggtggaggcgtttcagttggtgctcacaatcatgggaaagttgtcgat
gtaaataatgcattagatggagatggcccattctcaccagaaagagctggatcagttcca
attggtgatttagttaaaatgtgttttagtggaaaatatagtgaagcagaagtatatggc
aaggctgtaggaaaaggtggatttgttggttatctaaacacaaatgatgtaaaaggtgtt
attgataagatggaagaaggagataaagaatgtgaatcaatatacaaagcatttgtttat
caaatttcaaaagcaatcggagaaatgtcagttgtattagaaggtaaagttgatcaaatt
atttttaccggaggaattgcatactcaccaacacttgttccagaccttaaagcaaaagtt
gaatggatagccccagttacagtttatcctggagaagatgaattacttgctctagctcaa
ggtgctataagagtacttgatggagaagaacaagctaaggtttactag
(SEQ ID NO: 3)

**FIG. 13. CheA (Chemotaxis protein) *C. beijerinckii* NCIMB 8052 DNA sequence** atggatttgaaaaagcatcaacctttatttataaaaagatatagaggaggagtaaggatg
gatacatctcaatatatgtcaatgtttttagaggagtcattggaaaatttacaaacattg
aacgaatcattattagatttagagcaaaatccagatgatacagataaggttaatgaaata
tttagagttgcccacacaattaaggggatggcagcgactatgggatttactgatttagca
gaacttacccataagatggaagatgtattagctgaatttagagaaggaaaactaaaagta
actcaggatgtagtaacagtattatttgattgccttgatacattagaaaagatggttgat
aacgttcaagaaggttctgaggaaaaaatagatatagatggaataatgaaagccttagct
gatataaaagaaaatggaaacaatagtaacacacaagaagaaacacaagatagtgaaatc
aagtcagaagaaggaagaaaaatgatatcaggtgatgaatttgatttagatttaaatcaa
tatgacacgtctgttattagacaagctagagaaaaaggttttaactctattgaattaaaa
gtaacattaagtgaaaatactttgttaaaatcagcaagagcctttttaatagttaaagat
cttgaagatcacggagaaatactaaaatcagacccatcaactcaagaaattgaaaatgaa
gagtttgattttgagttgaaatttgtattagtaactaaaaatactgtagatgaaatatta
actgttgtaaatggaatttcagaagttgcaaaagttgaagcttctttaatagaattagaa
agcccagatatagctccaaaagaagcagaagtaaaagaagtgccacaggtaccagctata
gaaaaagcttcaggagaaaagccggctgaagcaaaagttgagacaaagcaaccagttgct
aaaaagcctactcaaaagaaagaagttaagaaggcacatcaatcagtaagagttgattta
gagagaatagataatttaatgaatatggtttctgagcttgtaatttatagaactcgatta
gaacaaatcgtaaatgttcataaatctcaagagttaaatgaaacattggaacaagtagga
aggacaacatctgatcttcaagatttagtcatgaagattagaatgcttccgctagataca
gtattcaatagattcccaagaatgataagggatatatcagtagagttaaataaggaaatt
aactttgttatagaaggtgctgatactgaacttgatagaactgttattgatgaaataggt
gaaccattaatacatttattaagaaatgcagcggatcatgggatagaatctgctgaaaag
agaattgcacaaggcaagcctccagttggaactgtgaagcttattgcataccaagaagga
acaaaagcattaataaaagtatcagatgatggagcaggaataaatcttgaaagagtaaaa
gctaaggcagagcaaaaaggaataaacacagaaggattgtcagatagtgatattaagaat
ttgatttttgctcaaggatttagcactaatgaagttgtaacagatatctcaggaagagga
gttggaatggatgttgttaagacaaaaattgcagcactcggtggtactgtagatctacta
agtgaagaaggcaaaggctcaacttttgtaattaagcttccacttacattacaaataata
caagctttacttgtaaaagtaggagaggaaacattagcaatatcattaggatttattgat
agagtaattgactataaagaggaaaatataaagaagagtaatggaaaagaagttattatt
tatagagaaaatgtaattccattagtaagattaaatgaaactttagatatagaggctagt
aatactgataagaaatttgttataatagttaatgtaggtgataaaactataggtttatta
gtcgattcattacttggacaacaagaaatagttataaagccactcggaaaaacattaaag
aatttagatcagtatattggtgcgactatacttggtaatggtttagtaacgctgatacta
gatgtaggggcattattataa
(SEQ ID NO: 4)

Figure 14:
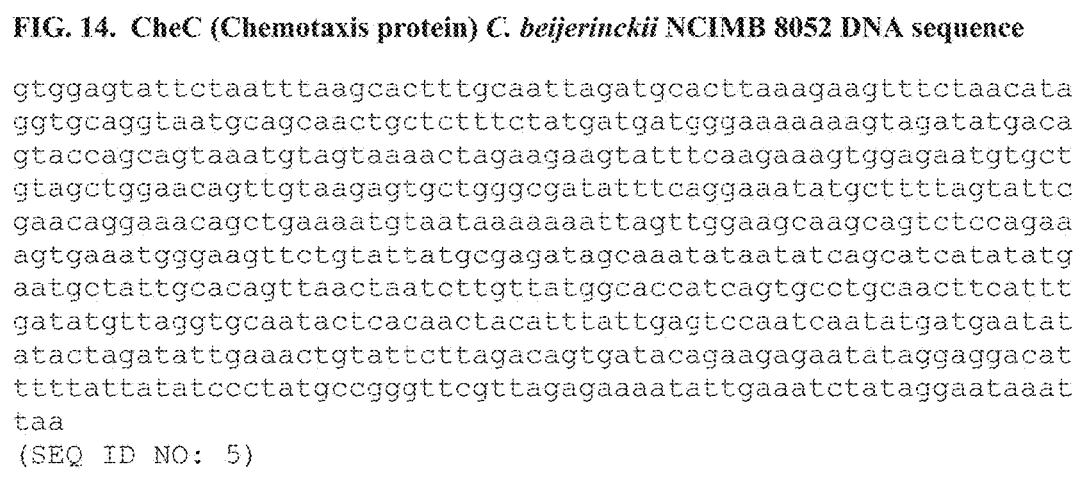

**FIG. 14. CheC (Chemotaxis protein) *C. beijerinckii* NCIMB 8052 DNA sequence** gtggagtattctaatttaagcactttgcaattagatgcacttaaagaagtttctaacata
ggtgcaggtaatgcagcaactgctctttctatgatgatgggaaaaaagtagatatgaca
gtaccagcagtaaatgtagtaaaactagaagaagtatttcaagaaagtggagaatgtgct
gtagctggaacagttgtaagagtgctgggcgatatttcaggaaatatgcttttagtattc
gaacaggaaacagctgaaaatgtaataaaaaaattagttggaagcaagcagtctccagaa
agtgaaatgggaagttctgtattatgcgagatagcaaatataatatcagcatcatatatg
aatgctattgcacagttaactaatcttgttatggcaccatcagtgcctgcaacttcattt
gatatgttaggtgcaatactcacaactacatttattgagtccaatcaatatgatgaatat
atactagatattgaaactgtattcttagacagtgatacagaagagaatataggaggacat
ttttattatatccctatgccgggttcgttagagaaatattgaaatctataggaataaat
taa
(SEQ ID NO: 5)

**FIG. 15. CheD (Chemotaxis protein) *C. beijerinckii* NCIMB 8052 DNA sequence** atgataagtgcagaagtaaaagtagggatagctgatctaaatttagtgctagatccagga
ataataatgacaataggactagggtcatgtataggaattgccttatatgataagataagt
aaggtggcagggttagcacacataatgcttcctgatagtacacaatttaaaagtagtgca
aaccccatgaaatttgcagatttagctattccaatattaattgataaaatggaaaagcaa
gggtgtaaaaagagaaatctcgtggctaaaatagctggaggagcttcgatgtttaatttt
tctgataagagcataataagtgatattggaaaaaggaatagtgatgcagtgaagaaaagg
ttaaaagaagagtcaattcctataattgctgaagagataggtggaaataaaggtagaact
atgatcctttacgctagcgatggaaaagtaatacttaaagttgtagggcatggaattgta
gaattgtag
(SEQ ID NO: 6)

**FIG. 16. ManIIAB (Mannose-specific PTS system component IIAB) *C. beijerinckii* NCIMB 8052 DNA sequence** atggtaggaattattcttgctagtcacggagaatttgctaaaggcatcatgcaatctggt
gcgatgattttcggagaacaagaaaacgtaaaagctgttacgttgatgcctagcgaagga
cctgatgatcttagagcaaaaatgaaagatgcaatcgcatcctttgacaaccaagatgag
gttttattcttagttgatctttggggtggtacaccattcaaccaagcgaatatgctattt
gaagaacataaagataaatgggcaatcgtagctggtttgaatttaccaatgctgattgaa
acttatggtgcacgtctttcaatggaatctgctcatgaaattgcagcttatatcttaaat
gcaggtaaagaaggagttaaagttaaacccgaggagttagaaccagcagatactggtaat
gcttcaggagcgggagcagggcaatctaatgcaggtgcacctggatcgtttgaatacgtt
ttagctcgtatcgactctcgtttacttcatggtcaagtagcaactgcttggacaaaaact
gtaaatcctacacgaattattgtcgtgtcagatgatgtagctagagatactcttcgtaag
aatttgattacgcaagcttctcctccgggggttaaggctcatgttgttccagttgatcat
atgattaaacttgcaaaagatgataagcattttggaggccaacgtgcaatgcttcttttt
gaaaatccaaaagatgtgcttagagctgtagaagggggaataccgctaaagataatcaat
gttggttcaatggctcattctccaggtaaggttcaaccaagcaaagttttagctttcaat
caagaagatattgatatattcaataagcttaaacaagctggacttacttttgatgtgcgt
aaagtaccaaatgattcaaaagcaaatatggacgaaatacttaaaaaagcacaagaagaa
ttaaaaaaattaaaataa
(SEQ ID NO: 7)

**FIG. 17. ManIIC (Mannose-specific PTS system component IIC) *C. beijerinckii* NCIMB 8052 DNA sequence**

```
atgactttaaatatagttcaaattatattagtcattttaatagcatttttagctggtgta
gaaggtatcttagatgaattccaatttcaccaaccgataattgcttgtacattaattggc
ttggttacaggtaatttactaccatgcttaatcttaggtggtactcttcaaatgatagcc
ttaggttgggcaaatattggtgctgctgtagcacctgatgcagcattagccgctgttgca
tctgcaattattttagttcttggaggtcaaggtgaagcaggagttgcttcagcaatcgct
attgctgttcctttagcagttgcaggattattattaacaattatttgtcgtacacttgct
acagcgttcgtacattttatggatgctgctgctaaagaaggaaatcttagagctattgat
atgtggcaaatcgctgctatttgtctacaaggtatacgtattgcgattccagcagcacta
gtattagcaatcggtgcaggtcctattagttcattacttgctgctatgcctacttggtta
actggtggtttagcaattggtggtggaatggttgtagctgttggttatgcaatggtaatc
aacatgatggctacaaaagaagtatggccattcttcgcaattggttttgtattagcaact
gtttcacaaattacacttatcggacttggtgcaataggtgtagctttagcacttctttac
ttagcacttagcaaacaaggtggctcaggtaatggtggaaattcaaatactggtgatcct
ttaggggatctaatagatagatactaa
(SEQ ID NO: 8)
```

**FIG. 18. SpoIVA (Stage IV sporulation protein A) *C. beijerinckii* NCIMB 8052 DNA sequence** atgggagggaaaaatgtggacaattttaacatatacaaagatatagccgatagaacccaa
ggggacatatatgtaggagtcgtaggaccagttaggacagggaaatctacatttattaaa
aagttcatggatcttatggtaatacctaaaattgataatacttataaaaaggaaagagca
aaagatgagttaccacagagtggctcaggaaaaaatattcacacaacagaacctaaattt
gtacctaatgaagcagtagaaataaatttaggggatgaaataaaatttaaagtaaggatg
gttgactgcgtaggatatattgtaaaaggagcattaggatatctagatggtgaggaaact
aaaatggttcatacaccatggtatgattacgaaataccttttgaggatgcagcagaaatt
gggacaagaaaagttataaaagaccattcaacaataggattagtaattacaactgatgga
agtataactggaatagatagaaatgactatgtagaaccagaagaaagagtaatatatgaa
ttacagtcactaaataaaccatttattgtagttcttaatactaataagcctaattctcaa
gaaactaaggcattgaaaaaagaattagaagataaatataatgtaactgttcaagttatg
gatgtttataatatggaagaacaagatattgaggatttatttaaacacgtacttaaggaa
ttccctgtaaaagaaataaatattgatatgcctgaatggttagaaaaattggaatgtaac
cattggctaaaaaaagatttttcaacataattatgaacatgagtcaagatgtctctaag
gtaagagacataaaatactgcttaaatgattttgaaaatgaagactttatgggaaaggca
accataaatgaagttgatttgggtagtggaacagcaaaaatatctatgaaacctaaggat
ggaattttctataaggttcttagtgagatatgtaatttagaagttggttcagaaagtgac
ttgctcagcataataaatgacctaagtcatgcaaaatgtgaatatgataaggttaaagat
gcattggaagatgtaagagagagcggctatggattggttgcaccacaactttcggaaatg
aagtttgaggagcctgaaatagttaaacaaggtaataaatatggagttaaattaaaggca
agtgctccaagcttacatcttataaagtgtgatattaaaactgagataagccctataatg
ggatcagaaaaggaatcggaagaactagtaaaaggccttctagaacaatttgaaacagat
ccagcccttctttggcaaagtaatatgtttggaaaatctttagaagtgttagtaaaagaa
ggattacaaaacaagctatataaaatgccagaagatgttcaagttaagattcaaaagact
ttgcagaaaattattaatgaaggtaatggtggattaatctgtataatactttaa
(SEQ ID NO: 9)

**FIG. 19. SpoVB (Stage V sporulation protein B) *C. beijerinckii* NCIMB 8052 DNA sequence** atgaaaaaacaatccctaataagagggagcataattcttggagttgcaggaatattaaca
agatttttaggtctattctttagatggccactaataatgttaattggagatgagggaatt
ggatattatcaaatgtcatacccgctatatatgtttttatagctatggcttctggagtt
ccagttgcaatttctaagatgatatcagaaaagaatgcaacaaatgatatatatggaagc
tttgaagtaatgaaagaatctgctattttaatgacaataatagggacaggcacaacttta
gcattattctttttttgcaaaaccaatagtattatttttgaagtgggatccaaaagcgtat
tattcattaatcggaatatcatttgcaccaattgtaatatcatttgtaactatatttaga
ggattctttcaagggttacaaaatatgactccgtcagctatatcacagataatagagcag
attggtagagtcatattcggtgttggacttgctgtatttttactacctagaggcatagag
tactcagcaggtggtgcagcatttggagcaactgcgggagctgttcttggaggagcttat
ttatactcgaattataaaagagtaaagaaacgttatgccattaaaaaaataaaaagcaat
ccagaaatattaaatactatattaaagattgcaataccaatatcattaggtactacagta
tcaagtattatgaatttaatagattccatttagtaccacaaaaactattagatgcggga
ttcacaaatgtacaatcaactgtattatatgcgcaattaacaggtaaagcgtctgtaatt
gtaaatattccattaactctttctatggctatttgtacatctctaattcctatcatagct
gagaatttcatacttaagaaacagaaagagctaaaaagtaaaatagatgcatctatgaaa
atggcatcagtaattgctattccgtgcacttttgggttattctttttagctgaaccagta
atgaagtttatatttccaggcaggtttgaaggaatagagatattaaatatttatcatta
acaattcctttttataataattactcaaacaacaacagcaatactacaaggaacagggcat
tatataaaacctgttattaacctcttgattgggtgtttgattaaaattgtattaacgtgg
gtattagttcctatgcaaatgtttaacatatatggtgctgttttggcgagctttggagct
tatttaacagtaagtattttaaatatagtgatgatgaaatttacactaagagtaagactt
aatttatacgaaatattaataaaaccttgctatgcatccagtattatgatgttaattgta
ttaataagttataatattttatataagaatacaattagtaatggaatatcttgcttgaca
tctatatttttgggtatgatagtatatattataatgataattgtattcaaggtatttaat
gttgaagaaataagagatagatttaaaagaaagtaa
(SEQ ID NO: 10)

**FIG. 20. SspA (Small acid-soluble spore protein) *C. beijerinckii* NCIMB 8052 DNA sequence**

```
ttgatgtatatgtcatcaaataacagtggaagaaatagaacattagtaccagaagcaaag
gcaggattaaacagattaaaaactgaggttgcttcagaagttggattaagtgattatgaa
aacatcgataaaggaagcctttcttcaagacaaaatggatatgttggcggttatatggta
aaacatatgattcaagattacgaacaaggtcttaagtaa
(SEQ ID NO: 11)
```

FIG. 21A. Cbei_0322 DNA sequence atgaattttaagttaactagagaacaacaattagtacaacaaatggttagagaattcgcagtaa
atgaagttaagccaatagctgccgaaatcgacgaaacagaaagattccctatggaaaacgttga
aaaaatggctaagcttaaaatgatggggatcccatttttaaagaatttggtggagcaggcgga
gatgttctttcatatataattgctgtggaagaattatcaaaagtttgtggtactacaggagtta
ttctttcagcgcatacatcattatgtgcatcagtaattaatgaaaatggaactaacgaacaaag
agcaaaatatttacctgatctttgcagcggtaaaaagatcggtgctttcggattaacagaacca
ggtgctggtacagatgctgcaggacaacaaacaactgctgtattagaaggggaccattatgtat
taaatggttcaaaaatcttcataacaaatggtggagttgctgaaactttcataatatttgctat
gacagataagagtcaaggaacaaaaggaatttctgcattcatagtagaaaagttattcccagga
ttctcaataggaaaattagaaaacaagatgggaatcagagcatcttcaactactgagttagtta
tggaaaactgcatagtaccaaaagaaaacctacttagcaaagaaggtaagggatttggtatagc
aatgaaaactcttgatggaggaagaattggtatagctgctcaagctttaggtattgcagaagga
gcttttgaagaagctgttaactatatgaaagaaagaaaacaatttggtaaaccattatcagcat
tccaaggattacaatggtatatagctgaaatggatgttaaaatccaagctgctaaatacttagt
atacctagctgcaacaaagaagcaagctggtgagccttactcagtggatgctgcaagagctaaa
ttatttgctgcagatgttgcaatggaagttacaactaaggcagttcaaatctttggtggatatg
gttacactaaagaatacccagtagaaagaatgatgagagatgctaaaatatgcgaaatctacga
aggaacttcagaagttcaaaagatggttatcgcaggaagcattttaagatag
(SEQ ID NO: 12)

FIG. 21B. Cbei_0322 protein sequence mnfqltreqqlvqqmvrefavnevkpiaaeideserfpmenvekmaklkmmgipfskefggagg
dvlsyiisveelskvcgttgvilsahtslcasvinengtneqrakylpdlcsgkkigafgltep
gagtdaagqqttavlegdhyvlngskifitnggvaetfiifamtdksqgtkgisafiveksfpg
fsigklenkmgirassttelvmencivpkenllskegkgfgiamktldggrigiaaqalgiaeg
afeeavnymkerkqfgkplsafqglqwyiaemdvkiqaakylvylaatkkqagepysvdaarak
lfaadvamevttkavqifggygytkeypvermmrdakiceiyegtsevqkmviagsilr
(SEQ ID NO: 13)

FIG. 22A. DNA sequence of Cbei_1722 adh gene atggcacgttttactttaccaagagacatttatcatggagaaggagcacttgaggcacttaaaa
ctttaaaaggtaagaaagctttcttagtagttggtggcggatcaatgaaaagatttggatttct
taaacaagttgaagattatttaaaagaagcaggaatggaagtagaattatttgaaggtgttgaa
ccagatccatcagtggaaacagtaatgaaaggcgcagaagctatgagaaactttgagcctgatt
ggatagttgcaatgggtggaggatcaccaattgatgctgcaaaggctatgtggatattctacga
atacccagattttacttttgaacaagcagttgttccatttggattaccagaccttagacaaaaa
gctaagtttgtagctattccatcaacaagcggtacagctacagaagttacagcattctcagtta
tcacaaattattcagaaaaaattaaatatcctttagctgattttaacataactccagatatagc
aatagttgatccagcacttgctcaaactatgccaaaaactttaacagctcatactggaatggat
gcattaactcacgctatagaagcatacactgcatcacttcaatcaaatttctcagatccattag
caattaaagctgtagaaatggttcaagaaaatttaatcaaatcatttgaaggagataaagaagc
tagaaatctaatgcatgaagctcaatgtttagctggaatggcattttctaatgcattacttgga
atagttcactcaatggctcataaggttggtgctgtattccatattcctcatggatgtgcaaatg
ctatatttttaccatatgtaattgagtataacagaacaaaatgcgaaaatagatatggagatat
tgcgagagccttaaaattaaaggaaacaatgatgccgagttaactgattcattaattgaatta
attaatggattaaatgataagttagagattcctcactcaatgaaagagtatggagttactgaag
aagattttaaagctaatctttcatttatcgctcataacgcagtattagatgcatgcacaggatc
aaatcctagagaaatagatgatgctacaatggaaaaattatttgaatgcacatactatggaact
aaagttaatttgtaa
(SEQ ID NO: 14)

FIG. 22B. Predicted amino Acid sequence of Cbei_1722 adh protein

MARFTLPRDLYHGEGALEVLKTLKGKKAFVVVGGGSMKRFGFLKQVEDYLTEAGMEVELFEGVE
PDPSVETVMKGAEAMRNFEPDWIVAMGGGSPIDAAKAMWIFYEYPDFTFEQAVVPFGLPELRQK
AKFVAIPSTSGTATEVTAFSVITNYTEKIKYPLADFNITPDIAIVDPVLAQTMPKTLTAHTGMD
ALTHAIEAYTASLRSNFSDPLAIKALQMVQENLIKSFEGDKEARNLMHEAQCLAGMAFSNALLG
IVHSMAHKVGAVFHIPHGCANAIFLPYVIQYNRTKCEDRYADIARALKLEGNTDSELTDSLIGM
INKMNSDLNIPHSMKEYGVTEEDFKANLSFIAHNAVLDACTGSNPREIDDATMEKLFECTYYGT
KVEL
(SEQ ID NO: 15)

FIG. 23A. Cbei_3111 DNA sequence atgcatatgtcatcaaataatagtggaagaaatagaacattagtaccagaagcaaaacaaggat
taaacagattaaaaactgaggttgcttcagaagttggattaagcaattatgaaagcatggataa
aggaaacctttcttcaagacaaaatggatatgttggcggatatatggtaaaacatatgatcgaa
gattatgaacaaggtcttaagtaa
(SEQ ID NO: 16)

FIG. 23B. Cbei_3111 protein sequence mhmssnnsgrnrtlvpeakqglnrlktevasevglsnyesmdkgnlssrqngyvggymvkhmie
dyeqglk
(SEQ ID NO: 17)

FIG. 24A. Cbei_3250 DNA seq atgtcatcaaataatagtggaagaaacagaacattagtaccagaagcaaaacaaggattaaaca
gattaaaaactgaggttgcttcagaagtaggattacatgattacgaaaatcaagataaaggaaa
tttatcttcaagacaaaatggatacgttggcggatacatggttaagcacatgattgaaagctac
gaacaaggtttaaagtaa
(SEQ ID NO: 18)

FIG. 24B. Cbei_3250 Protein seq

MSSNNSGRNRTLVPEAKQGLNRLKTEVASEVGLHDYENQDKGNLSSRQNGYVGGYMVKHMIESY
EQGLK
(SEQ ID NO: 19)

METHODS AND COMPOSITIONS FOR PRODUCING SOLVENTS

CROSS-REFERENCE TO RELATED APPLICATIONS

This application is a divisional application of U.S. Ser. No. 12/154,027, filed on May 19, 2008, now U.S. Pat. No. 9,080,187, which claims the benefit of priority to U.S. Provisional Application Ser. No. 60/930,775, filed May 17, 2007, the contents of these applications are incorporated by reference herein in their entirety.

STATEMENT REGARDING FEDERALLY SPONSORED RESEARCH OR DEVELOPMENT

This invention was made with government support under grant number 2001-35504-10668 awarded by the United States Department of Agriculture. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 2710 bytes ASCII (text) file named "131127seqlist" created on Jul. 8, 2015.

FIELD OF INVENTION

The compositions and methods described herein pertain to the generation of solvents, including but not limited to the generation of butanol. Specifically, the invention relates to genetic modification of solventogenic microorganisms to enhance production of solvents. More specifically, the invention relates to genetic modification of solventogenic clostridia to enhance efficiency of production of butanol.

BACKGROUND OF THE INVENTION

With the inevitable depletion of petroleum reserves, fast-growing global populations, and widespread industrialization, there has been an increasing worldwide interest in renewable energies. There is a growing consensus that producing liquid biofuels such as ethanol from renewable and inexpensive lignocellulosic-based plant materials (biomass) has a great potential to meet a large portion of this nation's energy demand in the transportation sector. Moreover, producing biofuels from biomass will simultaneously address three important societal concerns: security of supply (biofuels can be produced locally in sustainable systems), lower greenhouse gas (biofuels recycle carbon dioxide), and support of agriculture. The U.S. Department of Energy (DOE) has set a goal to replace 30% of the liquid transportation fuel with biofuels by 2030.

Similar to ethanol, butanol has many favorable attributes as a fuel molecule. However, it is an underexploited biofuel. Butanol can be produced as a co-product with ethanol and acetone from carbohydrates through fermentation by several solventogenic Clostridia. Compared to the currently popular fuel additive, ethanol, butanol has several advantages. It contains around 22% oxygen which when used as a fuel will result in more complete combustion and low exhaust smoke. In addition, it has a higher energy content (BTU/volume) than ethanol, is more miscible with gasoline and diesel, and has a lower vapor pressure and solubility characteristics which would allow for it to be shipped by pipeline, unlike ethanol.

Solventogenic clostridia are well-known as natural producers of organic solvents via fermentation process. *C. acetobutylicum* and *C. beijerinckii* are among the prominent solvent-producing strains capable of producing acetone and butanol as the main fermentation products (Jones, D. T., and D. R. Woods. 1986. Acetone-butanol fermentation revisited. Microbiol. Mol. Biol. Rev. 50:484-524.) Efforts have been made to improve the Clostridia-based butanol fermentation processes by developing new strains and downstream technologies. For example, as described in U.S. Pat. No. 6,358,717, which is incorporated herein by reference in its entirety, Blaschek and others used chemical mutagenesis to develop a mutant strain of *Clostridium beijerinckii*, BA101 with higher butanol concentration. To circumvent butanol inhibition, Blaschek and others also developed various downstream processes including gas stripping, pervaporation, and liquid-liquid extraction. See, e.g., Ezeji, T. C., Qureshi, N. & Blaschek, H. P. Butanol fermentation research: Upstream and downstream manipulations. Chem Rec 4, 305-314 (2004); US Pat. Pub. No. 2005/0089979; Qureshi et al., Butanol production using *Clostridium beijerinckii* BA101 hyper-butanol producing mutant strain and recovery by pervaporation, Appl Biochem Biotech 84-6, 225-235 (2000); Formanek et al., Enhanced butanol production by *Clostridium beijerinckii* BA101 grown in semidefined P2 medium containing 6 percent maltodextrin or glucose. Applied and Env. Microbiol. 63(6):2306-2310 (1997); and Ezeji et al., Acetone butanol ethanol (ABE) production from concentrated substrate: reduction in substrate inhibition by fed-batch technique and product inhibition by gas stripping, Appl Microbiol Biot 63, 653-658 (2004), each of which is incorporated herein by reference in its entirety.

The butanol biosynthesis pathway of the solvent producing Clostridia has been studied, and some of the enzymes involved therein have been purified and characterized. See, e.g., Boynton et al., Cloning, sequencing, and expression of clustered genes encoding beta-hydroxybutyryl-coenzyme A (CoA) dehydrogenase, crotonase, and butyryl-CoA dehydrogenase from *Clostridium acetobutylicum* ATCC 824, Journal of Bacteriology 178, 3015-3024 (1996); Petersen & Bennett, Cloning of the *Clostridium acetobutylicum* ATCC 824 Acetyl Coenzyme-a Acetyltransferase (Thiolase-Ec 2.3.1.9) Gene, Applied and Environmental Microbiology 57, 2735-2741 (1991); Petersen et al., Molecular-Cloning of an Alcohol (Butanol) Dehydrogenase Gene-Cluster from *Clostridium acetobutylicum* ATCC-824, Journal of Bacteriology 173, 1831-1834 (1991); and Durre et al., Solventogenic Enzymes of *Clostridium acetobutylicum*—Catalytic Properties, Genetic Organization, and Transcriptional Regulation, Fems Microbiol Rev 17, 251-262 (1995), each of which is incorporated herein by reference in its entirety.

Butanol fermentation has traditionally been constrained by self-limitation of the reaction due to the toxic effect of the product on the microorganism involved in the process. There is a need for producing solventogenic microorganisms such as clostridia that achieve increased efficiency in the production of bio-butanol.

BRIEF SUMMARY OF THE INVENTION

Described herein are methods, systems and synthetic biology approaches for solvent production, including but not limited to butanol production. Described herein are recombinant bacteria and yeast strains which may be used in production of butanol from lignocellulosic and other plant-based feedstocks. Described herein are methods of producing solvents, including but not limited to butanol, using recombinant bacteria and yeast strains.

Described herein are genetically-modified solventogenic organism strains comprising altered expression or structure of a gene relative to the original organism strain, wherein such genetic modifications result in increased efficiency of solvent production. Described herein are genetically-modified solventogenic clostridia strains comprising altered expression or structure of a gene relative to the clostridia strain prior to its genetic modification, wherein such genetic modifications result in increased efficiency of butanol production. In some modifications the clostridia species is *Clostridium beijerinckii* which is an anaerobic bacterium known for the fermentative production of acetone and butanol. In some embodiments, the genetic modifications are introduced by genetic recombination. In some embodiments, the genetic modifications are introduced by nucleic acid transformation.

Described herein are methods for producing genetically-modified solventogenic organism strains wherein such genetic modifications result in increased efficiency of solvent production. Described herein are methods for identifying genetic signatures associated with increased efficiency of butanol production wherein the genetic signatures include, but are not limited to, increased or decreased expression of genes related to butanol production pathway and variants thereof, and modified or altered sequences of genes involved in or related to the butanol production pathway. Genes and sequence variants thereof that have been identified in relation to increased efficiency of solvent production are used to transform bacteria (e.g., clostridia) or other microorganisms and increased or decreased expression of these genes are correlated with more efficient butanol production by these recombinant solventogenic organisms.

Increased efficiency of solvent production can be determined in any number of ways including but not limited to: concentration (weight/volume) of solvent in fermentation medium, yield (weight/weight) of solvent per amount of substrate, and rate of solvent formation (weight/volume/time).

Described herein are recombinant solventogenic organism strains comprising increased expression of a gene selected from the group consisting of Adh, Bcd, and Buk and variants thereof, relative to the organism strain prior to its transformation.

Described herein are recombinant solventogenic organisms comprising increased expression of a gene selected from the group consisting of CheA, CheC, and CheD and variants thereof relative to the organism strain prior to its transformation.

Described herein are recombinant solventogenic organisms comprising decreased expression of a gene selected from the group consisting of ManIIAB and ManIIC and variants thereof relative to the organism strain prior to its transformation.

Described herein are recombinant solventogenic organisms comprising decreased expression of a gene selected from the group consisting of SpoIVA, SpoVB, and SspA and variants thereof relative to the organism strain prior to its transformation.

In some variations, the recombinant solventogenic organisms described herein comprise a heterologous nucleic acid sequence. In some variations, the recombinant solventogenic organisms described herein comprise an introduced heterologous nucleic acid. In some variations, expression of the heterologous nucleic acid sequence is controlled by an inducible promoter. In some variations, expression of the heterologous nucleic acid sequence is controlled by a constitutive promoter.

In some variations, the recombinant solventogenic organisms described herein comprise an mRNA resulting from transcription of the heterologous nucleic acid sequence, wherein the mRNA accumulates to a higher or lower level relative to the organism strain prior to transformation.

In some variations, the recombinant solventogenic organisms described herein comprise a protein resulting from the heterologous nucleic acid, and the protein accumulates to a higher or lower level relative to the organism strain prior to its transformation.

In some variations, the recombinant solventogenic organisms described herein comprise a protein with an altered activation state which is correlated with increased production of a solvent, relative to the organism strain prior to its transformation.

In some variations, the recombinant solventogenic organisms described herein are yeast.

In some variations, the recombinant solventogenic organisms described herein are bacteria. In some variations, the recombinant solventogenic organisms described herein are *Escherichia*. In some variations, the recombinant solventogenic organisms described herein are *Escherichia coli*. In some variations, the recombinant solventogenic organisms described herein are *Clostridium*. In some variations, the recombinant solventogenic organisms described herein are *Clostridium beijerinckii*. In some variations, the recombinant solventogenic organisms described herein are *Clostridium acetobutylicum*.

In some variations, the recombinant solventogenic organisms described herein are cellulolytic.

In some variations, the recombinant solventogenic organisms described herein are non-cellulolytic.

In some variations, the recombinant solventogenic organisms described herein comprise an siRNA, DNAzyme, or antisense nucleic acid.

In some variations, the recombinant solventogenic organisms described herein comprise a heterologous nucleic acid from a *Clostridium*. In some variations, the recombinant solventogenic organisms described herein comprise a heterologous nucleic acid from a solventogenic *Clostridium*. In some variations, the recombinant solventogenic organisms described herein a heterologous nucleic acid from a *Clostridium beijerinckii*. In some variations, the recombinant solventogenic organisms described herein comprise a heterologous nucleic acid from *Clostridium beijerinckii* 8052. In some variations, the recombinant solventogenic organisms described herein comprise a heterologous nucleic acid from *Clostridium beijerinckii* BA101.

In some variations, the recombinant solventogenic organisms described herein produce butanol. In some variations, the recombinant solventogenic organisms described herein produce ethanol. In some variations, the recombinant solventogenic organisms described herein produce acetone.

Described herein are methods of producing a solvent comprising culturing the recombinant solventogenic organisms described herein.

Described herein are methods for producing butanol, comprising culturing the recombinant solventogenic organisms described herein.

Described herein are methods for producing ethanol, comprising culturing the recombinant solventogenic organisms described herein.

Described herein are methods of identifying a gene related to production of a solvent comprising culturing cells in a medium comprising a material which can be acted on to produce the solvent, comprising measuring the level of the solvent, and correlating an accumulation of a specific mRNA population via microarray with production of the solvent.

Described herein are methods of identifying the solventogenic potential of an organism comprising culturing cells in a medium comprising a material which can be acted on to produce the solvent, and correlating an accumulation of an mRNA population selected from the group consisting of Adh, Bcd, Buk, CheA, CheC, CheD, ManIIAB, ManIIC, SpoIVA, SpoVB, and SspA mRNA. In some variations the organism is yeast. In some variations the organism is bacteria. In some variations the organism is an *Escherichia coli*. In some variations the organism is a *Clostridium*. In some variations the organism is a *Clostridium beijerinckii*. In some variations the organism is a *Clostridium acetobutylicum*. In some variations the organism is cellulolytic. In some variations the organism is non-cellulolytic. In some variations the organism is recombinant.

These and other embodiments, features and advantages will become more apparent to those skilled in the art when taken with reference to the following more detailed description of the invention in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated herein and constitute part of this specification, illustrate presently preferred embodiments of the invention, and, together with the general description given above and the detailed description given below, serve to explain features of the invention.

FIG. 1 depicts growth curves (panel A) and pH profiles (panel B), respectively, for the fermentor cultures of *C. beijerinckii* NCIMB 8052 (♦) and *C. beijerinckii* BA101 (o). This figure is described in Example 2.

FIG. 2 depicts formation of total solvents (panel A), butanol (panel B), and acetone (panel C), respectively, in the fermentor cultures of *C. beijerinckii* NCIMB 8052 (♦) and *C. beijerinckii* BA101 (o). Time courses are shown for the production of solvents in *C. beijerinckii* BA101 in comparison with *C. beijerinckii* NCIMB 8052. This figure is described in Example 2.

FIG. 3 depicts mRNA accumulation profiles analyzed by DNA microarray for *C. beijerinckii* NCIMB 8052 (panel A) and *C. beijerinckii* BA101 (panel B), respectively, over the time course of fermentation. This figure is in color, and is described in Example 4.

FIG. 4 quantitatively depicts differential mRNA accumulation of solventogenic genes in *C. beijerinckii* NCIMB 8052 (♦) and *C. beijerinckii* BA101 (o). Increased expression in *C. beijerinckii* BA101 during the solventogenic stage is shown for alcohol dehydrogenase (Adh), butyryl-CoA dehydrogenase (Bcd) and butyrate kinase (Buk). This figure is described in Example 4.

FIG. 5 depicts differential mRNA accumulation of sugar transporters in *C. beijerinckii* NCIMB 8052 (♦) and *C. beijerinckii* BA101 (o). Components of mannose-family phosphoenolpyruvate (PEP)-dependent phosphotransferase system IIA, IIB (ManIIAB) and IIC (ManIIC) were significantly down-regulated in *C. beijerinckii* BA101. This figure is described in Example 4.

FIG. 6 depicts differential mRNA accumulation of sporulation genes in *C. beijerinckii* NCIMB 8052 (♦) and *C. beijerinckii* BA101 (o). Induction of late stage sporulation factors was much weaker in *C. beijerinckii* BA101 than in the wild-type strain. Lowered activation in *C. beijerinckii* BA101 through the solventogenic phase is shown for coat morphosis sporulation protein (SpoIVA), Stage V sporulation protein B (SpoVB) and small acid-soluble spore protein (SspA). This figure is described in Example 4.

FIG. 7 depicts differential mRNA accumulation of chemotaxis genes in *C. beijerinckii* NCIMB 8052 (♦) and *C. beijerinckii* BA101 (o). Higher expression levels of CheA, CheC, CheD and CheW in a chemotaxis gene cluster are shown for *C. beijerinckii* BA101 during the solventogenic stage.

FIG. 8 depicts solventogenic mRNAs with comparable accumulation kinetics in *C. beijerinckii* NCIMB 8052 (♦) and *C. beijerinckii* BA101 (o). Expression of aceto-acetyl CoA:acetate-butyrate CoA transferase subunit α/β (CtfA/B) and acetoacetate decarboxylase (Adc) were highly activated at the onset of solventogenic phase in *C. beijerinckii* BA101 and *C. beijerinckii* NCIMB 8052. Changes in expression levels were much smaller for thiolase (Thl), 3-hydroxybutyryl-CoA dehydrogenase (Hcd) and crotonase (Crt) in *C. beijerinckii* BA101 and *C. beijerinckii* NCIMB 8052. This figure is described in Example 4.

FIG. 9 depicts reactions in the clostridial solventogenic pathway. Genes involved in catalyzing the conversion of intermediate metabolites are indicated.

FIG. 10 shows the Adh (Alcohol dehydrogenase) gene Cbei_2181 of *C. beijerinckii* NCIMB 8052 DNA sequence (SEQ ID NO: 1).

FIG. 11 shows the Bcd (Butyryl-CoA dehydrogenase) gene Cbei_2035 of *C. beijerinckii* NCIMB 8052 DNA sequence (SEQ ID NO: 2).

FIG. 12 shows the Buk (Butyrate kinase) *C. beijerinckii* NCIMB 8052 DNA sequence (SEQ ID NO: 3).

FIG. 13 shows the CheA (Chemotaxis protein) *C. beijerinckii* NCIMB 8052 DNA sequence (SEQ ID NO: 4).

FIG. 14 shows the CheC (Chemotaxis protein) *C. beijerinckii* NCIMB 8052 DNA sequence (SEQ ID NO: 5).

FIG. 15 shows the CheD (Chemotaxis protein) *C. beijerinckii* NCIMB 8052 DNA sequence (SEQ ID NO: 6).

FIG. 16 shows the ManIIAB (Mannose-specific PTS system component IIAB) *C. beijerinckii* NCIMB 8052 DNA sequence (SEQ ID NO: 7).

FIG. 17 shows the ManIIC (Mannose-specific PTS system component IIC) *C. beijerinckii* NCIMB 8052 DNA sequence (SEQ ID NO: 8).

FIG. 18 shows the SpoIVA (Stage IV sporulation protein A) *C. beijerinckii* NCIMB 8052 DNA sequence (SEQ ID NO: 9).

FIG. 19 shows the SpoVB (Stage V sporulation protein B) *C. beijerinckii* NCIMB 8052 DNA sequence (SEQ ID NO: 10).

FIG. 20 shows the SspA (Small acid-soluble spore protein) *C. beijerinckii* NCIMB 8052 DNA sequence (SEQ ID NO: 11).

The DNA sequence (SEQ ID NO: 12) of the Cbei_0322 gene homologous to Bcd (Butyryl-CoA dehydrogenase) gene Cbei_2035 of *C. beijerinckii* NCIMB 8052 is shown in FIG. 21A and the protein sequence of Cbei_0322 (SEQ ID NO: 13) shown in FIG. 21B.

The DNA sequence (SEQ ID NO: 14) of the Cbei_1722 gene homologous to the Adh (Alcohol dehydrogenase) gene Cbei_2181 of *C. beijerinckii* NCIMB 8052 is shown in FIG. 22A and predicted amino acid sequence (SEQ ID NO: 15) of Cbei_1722 is shown in FIG. 22B.

The DNA sequence of Cbei_3111 (SEQ ID NO: 16) homologous to SspA (Small acid-soluble spore protein) gene Cbei_3080 of *C. beijerinckii* NCIMB 8052 is shown in FIG. 23A and the protein sequence of Cbei_3111 (SEQ ID NO: 17) shown in FIG. 23B.

The DNA sequence of Cbei_3250 (SEQ ID NO: 18) homologous to SspA (Small acid-soluble spore protein) gene Cbei_3080 of *C. beijerinckii* NCIMB 8052 is shown in FIG. 24A and the protein sequence of Cbei_3250 (SEQ ID NO: 19) shown in FIG. 24B.

DETAILED DESCRIPTION OF THE INVENTION

The detailed description illustrates by way of example, not by way of limitation, the principles of the invention. It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims. Hence, the invention is not limited to the preferred embodiments described exemplarily herein. Moreover, this description will clearly enable one skilled in the art to make and use the invention, and describes several embodiments, adaptations, variations, alternatives and uses of the invention, including what is presently believed by applicant to be the best mode of carrying out the invention.

As used herein and in the appended claims, the singular forms "a," "an," and "the" include plural reference unless the context clearly indicates otherwise. For example, reference to "alcohol dehydrogenase" is a reference to one or more such proteins and includes variants and equivalents thereof known to those skilled in the art.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described. The publications discussed herein are provided solely for their disclosure prior to the filing date of the present application. Nothing herein is to be construed as an admission that the inventors are not entitled to antedate such disclosure by virtue of prior invention or for any other reason.

This invention utilizes routine techniques in the field of recombinant genetics. Basic texts disclosing the general methods of use in this invention include Sambrook et al., Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)). General texts which describe molecular biological techniques include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (2nd Ed.), Vol. 1-3, Cold Spring Harbor Laboratory, Cold Spring Harbor, N. Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel")).

Described herein are 1) organisms for use in the methods and compositions described herein; 2) methods of identifying organisms for use in the methods and compositions described herein, 3) methods of modifying organisms, 4) methods of preparing substrates, 5) methods of processing cellulose to sugars, 6) methods of generating solvents from sugars, and 7) methods of optimizing organisms for use in industrial applications.

Described herein are methods for identifying genetic signatures (increased or decreased expression of gene(s) or, variant gene sequences) associated with a mutated clostridia (*C. beijerinckii* BA101) that exhibits butanol production with increased efficiency relative to the wild type clostridia (*C. beijerinckii* NCIMB 8052)). Methods for modifying clostridia or other organisms to acquire such genetic signatures wherein acquisition of the genetic signatures results in increased efficiency of ethanol production are described herein.

Organisms for Use in the Methods and Compositions Described Herein

In the broadest sense, any prokaryotic or eukaryotic organism capable of adaptation for use in the methods and compositions described herein may be used in the methods and compositions described herein.

In some variations, bacteria, fungi, yeast or other organisms which are initially solventogenic are used in the methods and compositions described herein. As used herein, a solventogenic organism is an organism that is at least partially capable of producing a solvent such as butanol, ethanol, acetone, or isopropanol. Non-limiting examples of solventogenic microorganisms include *Clostridium* species, such as *C. beijerinckii, C. beijerinckii* 8052, *C. beijerinckii* BA101, *C. acetobutylicum, C. pasteurianum, C. butyricum, C. sporogenes, C. felsenium, C. saccharobutylicum, C. saccharoperbutylacetonicum, C. tetanomorphum. C. aurantibutyricum, C. cadaveris, C. puniceum* and *C. thermosaccharolyticum* (Durre, P., Formation of solvents in Clostridia in 'Handbook on Clostridia', P. Durre (ed.), CRC Press-Taylor & Francis Group, Boca Raton, Fla., USA, 2005), as well as *C. algidixylanolyticum* (D M Broda, et. al., *Clostridium algidixylanolyticum* sp. nov., a psychrotolerant, xylan-degrading, spore-forming bacterium. Int J Syst Evol Microbiol 50:623-631, 2000), *C. thermopapyrolyticum* (B S Mendez, et. al., *Clostridium thermopapyrolyticum* sp. nov., a cellulolytic thermophile. Int J Syst Bacteriol 41 (2):281-283, 1991) and *C. carboxydivorans* (J S Liou, et. al., *Clostridium carboxydivorans* sp. nov., a solvent-producing *clostridium* isolated from an agricultural settling lagoon, and reclassification of the acetogen *Clostridium scatologenes* strain SL1 as *Clostridium drakei* sp. nov. Int J Syst Evol Microbiol 55:2085-2091, 2005), and some non-*Clostridium* species such as *Anaerobacter polyendosporus* (V I Duda, et. al., A new anaerobic bacterium, forming up to five endospores per cell—*Anaerobacter polyendosporus* gen. et sp. nov. Arch Microbiol 148(2):121-127, 1987; A V Siunov, et. al., Phylogenetic status of *Anaerobacter polyendosporus*, an anaerobic, polysporogenic bacterium. Int J Syst Bacteriol 49:1119-1124, 1999), *Butyribacterium methylotrophicum* (J G Zeikus, et. al., Isolation and characterization of a new, methylotrophic, acidogenic anaerobe, the Marburg strain. Curr Microbiol 3(6):381-386, 1980; G-J Shen, et. al., Biochemical basis for carbon monoxide tolerance and butanol production by *Butyribacterium methylotrophicum*. Appl Microbiol Biotechnol 51:827-832, 1999), *Thermoanaero-*

*bacterium thermosaccharolyticum* and *Thermoanaerobacterium* strain Mel9 (M D Collins, et. al., The phylogeny of the genus *Clostridium*: proposal of five new genera and eleven new species combinations. Int J Syst Bacteriol 44:812-826, 1994; P G Stroot, et. al., Description of a new butanol-producing thermophile *Thermoanaerobacterium* strain Mel9. In Abstracts of the 99th Meeting of the American Society for Microbiology, 1999), and *Thermohydrogenium kirishiense* (E V Zacharova, et. al., *Thermohydrogenium kirishiense* gen. nov. and sp. nov., a new anaerobic thermophilic bacterium. Arch Microbiol 160:492-497, 1993).

Anaerobic spore-forming bacteria belonging to the genus *Clostridium* have been useful in industrial applications including enzyme and solvent production. Among saccharolytic butyric acid-producing clostridia, there are a number of species capable of producing significant amounts of neutral solvents during the later stages of a batch fermentation under appropriate conditions. The strain used most extensively for the production of acetone and butanol are generally classified as *C. acetobutylicum*. A number of different species of butanol-producing clostridia are recognized based on differences in the type and ratio of the solvents produced, *C. beijerinckii* (*C. butylicum*) produces solvents in approximately the same ratio as *C. acetobutylicum*, however isopropanol is produced in place of acetone. *C. aurantibutyricum* produces both acetone and isopropanol in addition to butanol. *C. tetanomorphum* produces almost equimolar amounts of butanol and ethanol but no other solvents. (Jones and Woods (1986) supra).

Advantages of using *C. beijerinckii* over *C. acetobutylicum* include broader substrate range and better pH range, ability to produce butanol during log-phase growth, stability with respect to strain degeneration, and ability to use a variety of substrates to produce butanol. Moreover, the solventogenic genes on *C. beijerinckii* are located on the chromosome, whereas the genes are located on a plasmid in *C. acetobutylicum*. Thus *C. beijerinckii* is more genetically stable.

In some variations, bacteria, fungi, yeast or other organisms which are not initially solventogenic are used in the methods and compositions described herein.

Non-limiting examples of the organisms described herein include *Clostridium* sp. In some variations the *Clostridium* is *C. phytofermentans, C. thermohydrosulfuricum, C. absonum, C. absonum, C. acidisoli, C. akagii, C. algidixylanolyticum, C. bowmanii, C. cellulolyticum, C. cylindrosporum, C. diolis, C. estertheticum, C. estertheticum, C. estertheticum, C. frigidicarnis, C. frigidicarnis, C. frigoris, C. glycolicum, C. papyrosolvens, C. perfringens, C. pseudotetanicum, C., C. psychrophilum, C. rubrum, C. sardiniense, C. sardiniense, C. thermocellum, C. celerecrescens, C. lentocellum, C. polysaccharolyticum, C. populeti, C. thermohydrosulfuricum, C. thermocellum, C. cellulovorans,* or *C. josui*.

In some variations, the organisms described herein include *Escherichia* sp., including *E. coli, Saccharomyces* sp., including *S. cerevisiae*, and various Cyanobacteria.

In some variations, the organisms described herein include *Aspergillus* sp., *Bacillus* sp., *Brevibacterium* sp., *Clostridium* sp., *Corynebacterium* sp., *Gluconobacter* sp., *Pseudomonas* sp., *Rhodococcus* sp., *Streptomyces* sp., *Xanthomonas* sp., *Candida* sp., and *Zymomonas* sp.

In some variations the organisms described herein include *Acidithiobacillus* sp., *Acinetobacter* sp., *Allochromatium* sp., *Azotobacter* sp., *Bacillus* sp., *Bdellovibrio* sp., *Cellulomonas* sp., *Desulfovibrio* sp., *Geobacillus* sp., *Gluconobacter* sp., *Kocuria* sp., *Lactobacillus* sp., *Leuconostoc* sp., *Myxococcus* sp., *Pediococcus* sp., *Propionibacterium* sp., *Pseudomonas* sp., *Raoultella* sp., *Rhizobium* sp., *Rhodospirillum* sp., *Sporosarcina* sp., *Streptomyces* sp., *Thermus* sp., *Thiobacillus* sp., *Variovorax* sp., *Vibrio* sp., *Wautersia* sp., and *Zymomonas* sp.

In some variations the organisms described herein include *Selenomonas* sp., *Methanobrevibacter* sp., *Ruminococcus* sp., *Fibrobacter* sp., *Prevotella* sp., *Treponema* sp., *Azospirillum* sp., *Cellulomonas* sp., and *Trichoderma* sp.

In some variations the organisms described herein include *Acremonium* sp., *Alternaria* sp., *Aureobasidium* sp., *Botrytis* sp., *Chaetomium* sp., *Dipodascus* sp., *Endomyces* sp., *Eremascus* sp., *Geotrichum* sp., *Humicola* sp., *Neurospora* sp., *Penicillium* sp., *Pichia* sp., *Schizosaccharomyces* sp., *Sordaria* sp., and *Sordaria* sp.

In some variations the organisms described herein are cellulolytic. In some variations the organisms described herein are non-cellulolytic.

Methods of Identifying Organisms

Described herein are methods of identifying organisms for use in the methods and compositions described herein. Unless the context clearly indicates otherwise, any organism described herein may be identified by the methods described herein.

In some variations, organisms are screened for their ability to produce a particular product or products from one or more starting materials. In some variations, a culture medium or organisms in a culture medium are screened for the presence, absence, or level of a particular product. In some variations, a culture medium or organisms in a culture medium are screened for the presence, absence or level of a particular solvent, including but not limited to butanol, ethanol, or acetone. By way of nonlimiting example, screening for products or solvents may be via HPLC, mass spectrometry, GC, immunoassay, activity assay, or other methods known by those of skill in the art.

In some variations, an organism is screened for the presence, absence, or amount of a particular gene or gene product.

In some variations, DNA is screened for the presence, or absence, or copy number of a particular gene. By way of nonlimiting example, screening of DNA may be via Southern blot hybridization, PCR, microarray, or other methods known by those of skill in the art. In some variations genomic or non-genomic DNA is screened via microarray for the presence or absence of a particular gene.

In some variations, an organism's mRNA is screened for the presence, absence, or amount of a particular mRNA species. By way of nonlimiting example, screening of mRNA may be via Northern blot hybridization, PCR, microarray, or other methods known by those of skill in the art. In some variations, an organism's mRNA is screened via microarray for the presence, absence, or amount of a particular mRNA. In some variations, an organism's mRNA is screened via the method described in Example 4 for the presence, absence or amount of a particular mRNA species.

In some variations, an organism's mRNA is screened for the presence of a particular mRNA species.

In some variations, an organism's mRNA is screened for an amount of a particular mRNA species. In some variations, a recombinant organism's mRNA is screened for an amount of a particular mRNA species, relative to the organism strain prior to its transformation.

In some variations, a recombinant organism is screened for a decreased level of a particular mRNA species, relative to the organism strain prior to its transformation. In some variations, a recombinant organism is screened for an amount of decrease in level of a particular mRNA species, relative to the organism strain prior to its transformation, wherein the decreased mRNA species is used by a pathway that limits the ability of the recombinant organism to produce a preferred solvent. In some variations the amount of decrease of the mRNA species is 5%, 10%, 15%, 20%, 25%, 30%, 35%, 40%, 45%, 50%, 55%, 60%, 65%, 70%, 75%, 80%, 90%, 95%, 100%, relative to the organism strain prior to its transformation.

In some variations, an organism's mRNA is screened for an increased level of a particular mRNA species. In some variations, a recombinant organism's mRNA is screened for an increased level of a particular mRNA species, relative to the organism strain prior to its transformation. In some variations, a recombinant organism's mRNA is screened for an increased level of a particular mRNA species relative to the organism strain prior to its transformation, wherein the level of the particular mRNA species is increased at least 1.5-fold, 2-fold, 4-fold, 10-fold, 25-fold, 50-fold, 100-fold relative to the organism strain prior to its transformation. In some variations, a recombinant organism's mRNA is screened for an increased level of a particular mRNA species relative to the organism strain prior to its transformation, wherein the level of the particular mRNA species is increased at least 2-fold. In some variations, a recombinant organism's mRNA is screened for an increased level of a particular mRNA species relative to the organism strain prior to its transformation, wherein the level of the particular mRNA species is increased at least 5-fold. In some variations, a recombinant organism's mRNA is screened for an increased level of a particular mRNA species relative to the organism strain prior to its transformation, wherein the level of the particular mRNA species is increased at least 10-fold. In some variations, a recombinant organism's mRNA is screened for an increased level of a particular mRNA species relative to the organism strain prior to its transformation, wherein the level of the particular mRNA species is increased at least 15-fold. In some variations, a recombinant organism's mRNA is screened for an increased level of a particular mRNA species relative to the organism strain prior to its transformation, wherein the level of the particular mRNA species is increased at least 20-fold.

In some variations, an organism's proteins are screened for the presence, absence, or amount of a particular protein, or activation state of a particular protein. By way of non-limiting example, screening of proteins may be via Western blot hybridization, immunoassay, activity assay, microarray, various fluorescence and flow cytometry methods including fluorescence-activated cell sorting, or other methods known by those of skill in the art.

In some variations, an organism's proteins are screened for an amount of a particular protein species. In some variations, a recombinant organism's proteins are screened for an amount of a particular protein species, relative to the organism strain prior to its transformation.

In some variations, a recombinant organism is screened for a decreased level of a particular protein species, relative to the organism strain prior to its transformation. In some variations, a recombinant organism is screened for a decrease in amount of a particular protein species, relative to the organism strain prior to its transformation, wherein the decreased protein species is used by a pathway that limits the ability of the recombinant organism to produce a preferred solvent. In some variations the amount of decrease of the protein species is 5%, 10%, 15%, 20%, 25%, 30%, 35%, 40%, 45%, 50%, 55%, 60%, 65%, 70%, 75%, 80%, 90%, 95%, 100%, relative to the organism strain prior to its transformation.

In some variations, an organism's proteins are screened for an increased level of a particular protein species. In some variations, a recombinant organism strain's proteins are screened for an increased level of a particular protein species, relative to the organism strain prior to its transformation. In some variations, a recombinant organism's proteins are screened for an increased level of a particular protein species relative to the organism strain prior to its transformation, wherein the level of the particular protein species is increased about 1.5-fold, 2-fold, 5-fold, 10-fold, 20-fold, 30-fold, 40-fold, 50-fold, 60-fold, 80-fold, or 100-fold relative to the organism strain prior to its transformation. In some variations, a recombinant organism's proteins are screened for an increased level of a particular protein species relative to the organism strain prior to its transformation, wherein the level of the particular protein species is increased at least 2-fold. In some variations, a recombinant organism's proteins are screened for an increased level of a particular protein species relative to the organism strain prior to its transformation, wherein the level of the particular protein species is increased at least 5-fold. In some variations, a recombinant organism's proteins are screened for an increased level of a particular protein species relative to the organism strain prior to its transformation, wherein the level of the particular protein species is increased at least 10-fold. In some variations, a recombinant organism's proteins are screened for an increased level of a particular protein species relative to the organism strain prior to its transformation, wherein the level of the particular protein species is increased at least 20-fold. In some variations, a recombinant organism's proteins are screened for an increased level of a particular protein species relative to the organism strain prior to its transformation, wherein the level of the particular protein species is increased up to about 80-fold.

In some variations, an organism's proteins are screened for a level of a particular activated protein species. In some variations a protein is activated by phosphorylation, dephosphorylation, cleavage, refolding, or association with another molecule, including but not limited to another protein.

In some variations, an organism's proteins are screened for a level of a particular activated protein species. In some variations, a recombinant organism's proteins are screened for a level of a particular activated protein species, relative to the organism strain prior to its transformation.

In some variations, a recombinant organism is screened for a decreased level of a particular activated protein species, relative to the organism strain prior to its transformation. In some variations, a recombinant organism is screened for a decrease in level of a particular activated protein species, relative to the organism strain prior to its transformation, wherein the decreased activated protein species is used by a pathway that limits the ability of the recombinant organism to produce a preferred solvent. In some variations the amount of decrease of the activated protein species is 5%, 10%, 15%, 20%, 25%, 30%, 35%, 40%, 45%, 50%, 55%, 60%, 65%, 70%, 75%, 80%, 90%, 95%, 100%, relative to the organism strain prior to its transformation.

In some variations, a recombinant organism's proteins are screened for an increased level of a particular activated protein species, relative to the organism strain prior to its transformation. In some variations, a recombinant organism's proteins are screened for an increased level of a particular activated protein species relative to the organism strain prior to its transformation, wherein the level of the particular activated protein species is increased at least 1.5-fold, 2-fold, 5-fold, 10-fold, 20-fold, 30-fold, 40-fold, 50-fold, 60-fold, 80-fold, or 100-fold relative to the organism strain prior to its transformation. In some variations, a recombinant organism's proteins are screened for an increased level of a particular activated protein species relative to the organism strain prior to its transformation, wherein the level of the particular activated protein species is increased at least 1.5-fold. In some variations, a recombinant organism's proteins are screened for an increased level of a particular activated protein species relative to the organism strain prior to its transformation, wherein the level of the particular activated protein species is increased at least 5-fold. In some variations, a recombinant organism's proteins are screened for an increased level of a particular activated protein species relative to the organism strain prior to its transformation, wherein the level of the particular activated protein species is increased at least 15-fold. In some variations, a recombinant organism's proteins are screened for an increased level of a particular activated protein species relative to the organism strain prior to its transformation, wherein the level of the particular activated protein species is increased at least 20-fold. In some variations, a recombinant organism's proteins are screened for an increased level of a particular activated protein species relative to the organism strain prior to its transformation, wherein the level of the particular activated protein species is increased up to about 80-fold.

In some variations, an organism is screened for a level of a particular solvent. In some variations, a recombinant organism is screened for a level of a particular solvent, relative to the organism strain prior to its transformation.

In some variations, a recombinant organism is screened for a decreased level of a particular solvent, relative to the organism strain prior to its transformation. In some variations, a recombinant organism is screened for a decrease in level of a particular solvent, relative to the organism strain prior to its transformation, wherein the decreased solvent is generated by a pathway that limits the ability of the recombinant organism to produce a preferred solvent. In some variations, the solvent which has been decreased is ethanol. In some variations, the solvent which has been decreased is acetone. In some variations, the solvent which has been decreased is butanol. In some variations the amount of decrease is 5%, 10%, 15%, 20%, 25%, 30%, 35%, 40%, 45%, 50%, 55%, 60%, 65%, 70%, 75%, 80%, 90%, 95%, 100%, relative to the organism strain prior to its transformation.

Increased efficiency of solvent production can be determined in any number of ways including but not limited to: concentration (weight/volume) of solvent in fermentation medium, yield (weight/weight) of solvent per amount of substrate, and rate of solvent formation (weight/volume/time).

In one aspect of the invention, a recombinant organism strain is screened for an increased level of a particular solvent, relative to the organism strain prior to its transformation.

In some variations, recombinant solventogenic organism strains are screened for producing an increased amount of a particular solvent relative to the organism strain prior to its transformation, wherein the amount of the particular solvent is increased at least 1.1, 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.5, 5.0, 5.5, 6.0, 6.5, 7.0, 7.5, 8.0, 8.5, 9.0, 9.5, 10, 15, 20, 40, 60, 80, or 100-fold over that in the organism strain prior to its transformation.

Where the concentration of the solvent in the organism strain prior to its transformation is 10 g/L, the recombinant solventogenic organism strains are screened for having concentrations of the solvent of about 11, 12, 13, 14, 15, 16, 17, 18, 19, 20, 22, 24, 26, 28, 30, 32, 34, 36, 38, 40, 45, 50, 55, 60, 65, 70, 75, 80, 85, 90, 95, or 100 g/L.

In some variations, recombinant solventogenic organism strains are screened for producing an increased yield of a particular solvent per amount of the substrate, relative to the organism strain prior to its transformation. Where the yield of solvent in the organism strain prior to its transformation is about 20 g/100 g of substrate, recombinant solventogenic organism strains of the present invention are screened for producing yields of: 22, 24, 26, 28, 30, 32, 34, 36, 38, 40, 44, 48, 50, 52, 56, 60, 64, 68, 72, 76, or 80 g solvent per g substrate.

In some variations, recombinant organism strains are screened for displaying an increased rate of formation of a particular solvent, relative to the organism strain prior to its transformation. Where the rate of formation of solvent in the organism strain prior to its transformation is about 0.2 g/L/hour of substrate recombinant solventogenic organism strains are screened for producing rates of solvent formation of: 0.24, 0.26, 0.28, 0.3, 0.32, 0.34, 0.36, 0.38, 0.4, 0.44, 0.48, 0.52, 0.56, 0.6, 0.64, 0.68, 0.72, 0.76, 0.8, 0.9, 1, 1.1, 1.2, 1.3, 1.4, 1.5, 1.6, 1.7, 1.8, 1.9, 2, 3, 4, 8, or 12 g/L/hr.

In some variations, a recombinant organism is screened for an increased level of a particular solvent relative to the organism strain prior to its transformation, wherein the level of the particular solvent is increased at least 0.05%, 0.1%, 0.15%, 0.2%, 0.25%, 0.3%, 0.35%, 0.4%, 0.45%. 0.5%, 0.55%, 0.6%, 0.65%, 0.7%, 0.75%, 0.8% 0.9%. 0.95%, 1%, 1.1%, 1.2%, 1.3%, 1.4%, 1.5%. 1.6%, 1.7%, 1.8%, 1.9%, 2%, 2.1%, 2.2%, 2.3%, 2.4%, 2.5%, 2.75%, 3%, 3.25%, 3.5%, 3.75%, 4%, 4.25%, 4.5%, or 5%. In some variations, a recombinant organism is screened for an increased level of a particular solvent relative to the organism strain prior to its transformation, wherein the level of the particular solvent is increased at least 5%, 10%, 15%, 20%, 25%, 30%, 35%, 40%, 45%, 50%, 55%, 60%, 65%, 70%, 75%, 80%, 90%, 95%, 100%, 125%, 150%, 175%, 200%, 225%, 250%, 275%, 300%, 325%, 350%, 375%, 400%, 425%, 450%, 475%, 500%, 600%, 700%, 800%, 900%, or 1000%. In some variations, a recombinant organism is screened for an increased level of a particular solvent relative to the organism strain prior to its transformation, wherein the level of the particular solvent is increased at least 25%. In some variations, a recombinant organism is screened for an increased level of a particular solvent relative to the organism strain prior to its transformation, wherein the level of the particular solvent is increased at least 50%. In some variations, a recombinant organism is screened for an increased level of a particular solvent relative to the organism strain prior to its transformation, wherein the level of the particular solvent is increased at least 75%. In some variations, a recombinant organism is screened for an increased level of a particular solvent relative to the organism strain prior to its transformation, wherein the level of the particular solvent is increased at least 100%. In some variations, a recombinant organism is screened for an increased level of a particular solvent relative to the organism strain prior to its transformation, wherein the level of the particular solvent is increased at least 200%. In some variations, a recombinant organism is screened for an increased level of a particular solvent relative to the organism strain prior to its transformation, wherein the level of the particular solvent is increased between 0.05-500%. In some variations, a recombinant organism is screened for an increased level of a particular solvent relative to the organism strain prior to its transformation, wherein the level of the particular solvent is increased between 0.05-300%. In some variations, a recombinant organism is screened for an increased level of a particular solvent relative to the organism strain prior to its transformation, wherein the level of the particular solvent is increased between 0.5-500%. In some variations, a recombinant organism is screened for an increased level of a particular solvent relative to the organism strain prior to its transformation, wherein the level of the particular solvent is increased between 5-500%, In some variations, a recombinant organism is screened for an increased level of a particular solvent relative to the organism strain prior to its transformation, wherein the level of the particular solvent is increased between 100-500%. In some variations, a recombinant organism is screened for an increased level of a particular solvent relative to the organism strain prior to its transformation, wherein the level of the particular solvent is increased between 10-100%. In some variations, a recombinant organism is screened for an increased level of a particular solvent relative to the organism strain prior to its transformation, wherein the level of the particular solvent is increased between 500-1000%. In some variations, the solvent is butanol.

In some variations the solventogenic potential of an organism is evaluated by screening for the presence, absence, or amount of a particular DNA sequence, mRNA sequence, protein, reaction product or solvent. By way of nonlimiting example, the presence, absence, or amount of a particular DNA sequence, mRNA sequence, protein, reaction product or solvent related to reactions or reaction pathways used in the generation of solvents may be evaluated. By way of nonlimiting example, the presence, absence, or amount of a particular DNA sequence, mRNA sequence, protein, reaction product or solvent related to reactions or reaction pathways used in the tolerance to solvents may be evaluated. In some variations, the presence, absence, or amount of a particular DNA sequence, mRNA sequence, protein, reaction product or solvent related to sugar transporters relevant to the production of solvents is evaluated. In some variations, the presence, absence, or amount of a particular DNA sequence, mRNA sequence, protein, reaction product or solvent related to sporulation activities may be evaluated. In some variations, the presence, absence, or amount of a particular DNA sequence, mRNA sequence, protein, reaction product or solvent related to chemotaxis may be evaluated.

In some variations the solventogenic potential of an organism is evaluated by screening for the presence, absence, or amount of a combination of particular DNA sequences, mRNA sequences, proteins, products or solvents.

In some variations, the solventogenic potential of an organism is evaluated by transiently or stably transforming the organism with one or more genes related to production of a solvent, and screening for a particular product or solvent. In some variations, the solventogenic potential of an organism is evaluated by transiently or stably transforming the organism with one or more of the genes described herein, including but not limited to the genes described in the methods of processing cellulose to sugars, methods of generating solvents from sugars, and methods of optimizing organisms for use in industrial applications sections.

Methods of Modifying Organisms

In some variations, the organisms for use in the compositions and methods described herein are modified in order to improve their ability to produce a solvent, including but not limited to butanol, ethanol, or acetone. In some variations, the organisms for use in the compositions and methods described herein are genetically-modified in order to improve their ability to produce a solvent. In some variations, genetic material is introduced into the organisms for use in the compositions and methods described herein in order to improve their ability to produce a solvent.

Described herein are recombinant solventogenic organisms. In some variations the recombinant solventogenic organisms described herein have increased or decreased expression of a gene product relative to the organism strain prior to its transformation. An "organism strain prior to its transformation," as used herein refers to the starting organism strain that was transformed, which transformation yielded the recombinant organism.

For the purposes of this invention, the term "transformation" is used broadly encompass all methods for introducing a particular nucleic acid sequence into an organism. Thus, the term "transformation" indicates the genetic alteration of a cell resulting from the uptake and expression of foreign genetic material (DNA). Methods for uptake of foreign DNA include transduction, a process in which bacterial DNA is moved from one bacterium to another by a bacteriophage and bacterial conjugation wherein a living bacterial cell transfers genetic material through cell-to-cell contact.

The term "transformation" also indicates the genetic alteration of a cell resulting from the uptake and expression of a specific genetic sequence (altered or heterologous nucleic acid sequence) without uptake of a foreign genetic material. The latter would include, but is not limited to, sequence alterations induced by site-directed mutagenesis or genetic recombination.

Information about site-directed mutagenesis is found in the following publications and references cited within: Ling et al., *Approaches to DNA mutagenesis: an overview*, Anal Biochem. 254(2): 157-178 (1997); Dale et al., *Oligonucleotide-directed random mutagenesis using the phosphorothioate method*, Methods Mol. Biol. 57:369-374 (1996); Smith, *In vitro mutagenesis*, Ann. Rev. Genet. 19:423-462 (1985); Botstein & Shortle, *Strategies and applications of in vitro mutagenesis*, Science 229:1193-1201 (1985); Kunkel et al., *Rapid and efficient site-specific mutagenesis without phenotypic selection*, Methods in Enzymol. 154, 367-382 (1987); Zoller & Smith, *Oligonucleotide-directed mutagenesis: a simple method using two oligonucleotide primers and a single-stranded DNA template*, Methods in Enzymol. 154:329-350 (1987).

A solventogenic organism, as used herein, is an organism capable of producing one or more solvents, including but not limited to butanol, ethanol, isopropanol or acetone.

A "recombinant organism," as used herein, is a non-naturally occurring organism with an introduced nucleic acid sequence. The introduced nucleic acid sequence may be integrated into the organism's chromosome, or separate from the organism's chromosome. As nonlimiting examples, the introduced nucleic acid may be a plasmid, a vector, a virus, a viral particle, a bacteriophage, an artificial chromosome, a mini-chromosome, or a linear strand of single stranded or double stranded nucleic acid. A nucleic acid sequence may also be introduced by site directed mutagenesis or genetic recombination.

In some variations the introduced nucleic acid is a heterologous nucleic acid. A "heterologous nucleic acid," as used herein, refers to a sequence of nucleic acids derived from an organism strain different from the organism strain into which the nucleic acid is introduced.

There are many known methods of transiently or stably introducing nucleic acid into organisms. There are well-established strategies for nucleic acid transformation of bacteria in the literature, including those described in Mercenier and Chassy, *Strategies for the development of bacterial transformation systems*, Biochimie 70, 503-517 (1988), Trevors et al., *Electrotransformation of Bacteria by Plasmid DNA*, in Guide to Electroporation and Electrofusion, Ed. Chang, Chassy, Saunders and Sowers, Academic Press (1992), and Dower et al., *Protocols for the Transformation of Bacteria by Electroporation*, Ed. Chang, Chassy, Saunders and Sowers, Academic Press (1992), each of which is incorporated herein by reference in its entirety for all purposes.

There are well-established transformation systems for *Clostridium* sp. in the literature, including Blaschek and White, *Genetic systems development in the clostridia*, FEMS Microbiology Reviews 17, 349-356 (1995); Chen et al., *Factors involved in the transformation of previously non-transformable Clostridium perfringens type B.*, FEMS Microbiol Lett. 140(2-3):185-91 (1996); Phillips-Jones, *Introduction of Recombinant DNA into Clostridium* spp., in Electroporation Protocols for Microorganisms, Ed. Jac Nickoloff, Humana Press (1995); Young et al., *Genetic Methods in Clostridia*, in Methods in Microbiology, Vol. 29, Ed Margaret Smith and R. Elizabeth Sockett, Academic Press (1999); and Rood, *Genetic Analysis in Clostridium perfringens*, in The Clostridia: Molecular Biology and Pathogenesis, Ed. Rood, McClane, Songer and Titball, Academic Press (1997), each of which is incorporated herein by reference in its entirety for all purposes.

Nucleic acid molecules may be introduced into the yeast cells by standard yeast transformation methods such as Lithium acetate/single-stranded carrier DNA/polyethylene glycol method; Frozen Yeast Protocol using frozen yeast cells that are competent for transformation after thawing; Gene Gun Transformation using gold or tungsten nanoparticles coated with DNA that can be shot into cells; and Protoplast Transformation. See e.g., Sambrook et al., *Molecular Cloning: A Laboratory Manual*, 3d Ed., Cold Spring Harbor Press, Plainsview, N.Y. (2000). The transforming DNA may or may not be integrated into the genome of the yeast cell. Upon the co-transformation of a linearized vector and a nucleic acid molecule into a yeast cell, the nucleic acid molecule is inserted into the insertion site via gap repair, an endogenous homologous recombination system in *S. cerevisiae.*

By way of nonlimiting example, to construct a solvent-producing clostridia, including but not limited to a *C. beijerinckii, C. beijerinckii* NCIMB 8052, or *C. beijerinckii* BA101 strain, one or more genes related to solvent production may be expressed or overexpressed. Such genes may be isolated from another organism, including but not limited to different clostridia or butanol-producing clostridia. Those of skill in the art are familiar with the tools for genetic manipulation of clostridia, including but not limited to appropriate source DNA, promoters, enhancers, terminators, integration vectors, autonomously replicating vectors, transformation systems, enhanced- or site-specific recombination systems, transposons, mobile intron systems and culture media.

In some variations, an organism described herein is transformed with one or more genes expressible in the organism.

In some variations, an organism described herein is transformed with a gene from a cellulolytic organism. In some variations, an organism described herein is transformed with a gene from a non-cellulolytic organism.

In some variations, an organism described herein is transformed with a gene from a *Clostridium* strain. In some variations, an organism described herein is transformed with a gene from *Clostridium beijerinckii.*

In some variations, an organism described herein is transformed with one or more genes which have been altered so as to be better expressed in the organism. In some variations, an organism described herein is transformed with one or more genes which have been codon optimized for use in the organism. In some variations, an organism described herein is transformed with one or more genes which have been altered via site-directed mutagenesis to improve production of a particular solvent in the organism.

In some variations, an organism described herein is modified by random mutagenesis to improve production of a particular solvent in the organism.

In some variations, an organism described herein is transformed with one or more genes under the control of an inducible promoter. In some variations, an organism described herein is transformed with one or more genes under the control of a constitutive promoter.

In some variations, one or more of genes of interest is amplified via PCR from a solventogenic organism such as a clostridium or, more specifically, *C. beijerinckii* or *C. beijerinckii* BA101. In some variations a promoter active in clostridia is used. In some variations a terminator active in clostridia is used. In some variations an integration vector which allows insertion of genes into clostridia is used. In some variations a self-replicating or suicide vector which allows expression of heterologous genes in clostridia is used. (Flavia Ramirez; MS Thesis; University of Illinois—Urbana Champaign). In some variations, potential transformants bearing the target gene will be identified via one or more selectable or detectable markers. In some variations, potential transformants are analyzed by Southern blot hybridization, PCR, and/or activity assay. The engineered *Clostridia* strain may further be evaluated for solvent production, including but not limited to butanol, ethanol or acetone production.

In some variations, a yeast strain is used in a process to produce one or more solvents. Described herein are yeast strains wherein metabolic engineering and/or functional genomics have been utilized to optimize the yeast strain's solventogenic potential. Compared to a native butanol-producing host, such as Clostridia, the yeast *Saccharomyces cerevisiae* has several advantages. For example, *S. cerevisiae* is robust, displays a different tolerance to concentrations of product and inhibitors present in lignocellulosic hydrolysates, and is viable at a somewhat different pH range. In addition, yeast has a short doubling time, its genetics and physiology is well-studied, and many genetic engineering tools are available.

There are well-established strategies for transformation of yeast in the literature, including those described in Becker and Guarente, *Protocol for High-Efficiency Yeast Transformation*, in Guide to Electroporation and Electrofusion, Ed. Chang, Chassy, Saunders and Sowers, Academic Press (1992), which is incorporated herein by reference in its entirety for all purposes.

By way of nonlimiting example, to construct a solvent-producing yeast, including but not limited to a *S. cerevisiae* strain, one or more genes related to solvent production may be expressed or overexpressed. Such genes may be isolated from another organism, including but not limited to the native butanol producer clostridia. Those of skill in the art are familiar with the tools for genetic manipulation of yeast, including but not limited to appropriate source DNA, promoters, enhancers, terminators, integration vectors, transformation systems, and culture media.

The present invention relates to methods of obtaining the disclosed nucleic acid molecules and proteins and of using the disclosed nucleic acid molecules, proteins, fragments of proteins for gene identification and analysis, preparation of constructs, transformation of cells.

The term "an isolated nucleic acid" refers to a nucleic acid that is no longer accompanied by some of materials with which it is associated in its natural state or to a nucleic acid the structure of which is not identical to that of any of naturally occurring nucleic acid. Examples of an isolated nucleic acid include: DNA which has the sequence of part of a naturally occurring genomic DNA molecules, but are not flanked by two coding sequences that flank that part of the molecule in the genome of the organism in which it naturally occurs; a nucleic acid incorporated into a vector or into the genomic DNA of a prokaryote or eukaryote in a manner such that the resulting molecule is not identical to any naturally occurring vector or genomic DNA; a separate molecule such as a DNA, a genomic fragment, a fragment produced by polymerase chain reaction (PCR), or a restriction fragment; recombinant DNAs; and synthetic DNAs. An isolated nucleic acid may also be comprised of one or more segments of DNA, genomic DNA or synthetic DNA.

In some variations, one or more of genes of interest is amplified via PCR from a solventogenic organism such as a *clostridium* or, more specifically, *C. beijerinckii* or *C. beijerinckii* BA101. In some variations a promoter active in yeast, such as PyK or PGK, is used. In some variations a terminator active in yeast, such as CYCI terminator, is used. In some variations a yeast delta integration vector which allows sequential insertion of multiple cloned genes into the yeast dispersed chromosomal sites is used. In some variations, potential transformants bearing the target gene will be identified via one or more selectable or detectable markers. In some variations, potential transformants are analyzed by Southern blot hybridization, PCR, and/or activity assay. The engineered yeast or *S. cerevisiae* strain may further be evaluated for solvent production, including but not limited to butanol, ethanol or acetone production. In some variations the engineered yeast or *S. cerevisiae* strain is evaluated for butanol production.

In some variations, an organism described herein is optimized to decrease production of one or more gene products which compete with or are otherwise detrimental to the production of solvents. In some variations an organism described herein is transformed with a nucleic acid to decrease or impair expression of one or more gene products which compete with or are otherwise detrimental to the production of solvents.

In some variations, siRNA, DNAzymes, antisense, promoter inactivation, repressors, or other methods known by those of skill in the art are used to decrease production of one or more gene products which compete with or are otherwise detrimental to the production of solvents.

In some variations, a recombinant organism described herein has an altered level of a particular solvent. In some variations, a recombinant organism has an altered level of a particular solvent, relative to the organism strain prior to its transformation.

In some variations, a recombinant organism comprises a decreased level of a particular solvent, relative to the organism strain prior to its transformation. In some variations, a recombinant organism comprises a decrease in level of a particular solvent, relative to the organism strain prior to its transformation, wherein the decrease in level of the particular solvent is used by a pathway that limits the ability of the recombinant organism to produce a preferred solvent. In some variations, the solvent which has been decreased is ethanol. In some variations, the solvent which has been decreased is acetone. In some variations, the solvent which has been decreased is butanol. In some variations the amount of decrease is 5%, 10%, 15%, 20%, 25%, 30%, 35%, 40%, 45%, 50%, 55%, 60%, 65%, 70%, 75%, 80%, 90%, 95%, 100%, relative to the organism strain prior to its transformation.

In some variations, an organism comprises an altered level of a particular mRNA species. In some variations, a recombinant organism comprises an altered level of a particular mRNA species, relative to the organism strain prior to its transformation.

In some variations, a recombinant organism comprises a decreased level of a particular mRNA species, relative to the organism strain prior to its transformation. In some variations, a recombinant organism comprises a decrease in level of a particular mRNA species, relative to the organism strain prior to its transformation, wherein the decreased mRNA species is used by a pathway that limits the ability of the recombinant organism to produce a preferred solvent. In some variations the amount of decrease of the mRNA species is 5%, 10%, 15%, 20%, 25%, 30%, 35%, 40%, 45%, 50%, 55%, 60%, 65%, 70%, 75%, 80%, 90%, 95%, 100%, relative to the organism strain prior to its transformation.

In some variations, an organism comprises an altered amount of a particular protein species. In some variations, a recombinant organism comprises an altered amount of a particular protein species, relative to the organism strain prior to its transformation.

In some variations, a recombinant organism comprises a decreased level of a particular protein species, relative to the organism strain prior to its transformation. In some variations, a recombinant organism comprises a decrease in level of a particular protein species, relative to the organism strain prior to its transformation, wherein the decreased protein species is used by a pathway that limits the ability of the recombinant organism to produce a preferred solvent. In some variations the amount of decrease of the protein species is 5%, 10%, 15%, 20%, 25%, 30%, 35%, 40%, 45%, 50%, 55%, 60%, 65%, 70%, 75%, 80%, 90%, 95%, 100%, relative to the organism strain prior to its transformation.

In some variations, an organism comprises an altered level of a particular activated protein species. In some variations, a recombinant organism comprises an altered level of a particular activated protein species, relative to the organism strain prior to its transformation.

In some variations, a recombinant organism comprises a decreased level of a particular activated protein species, relative to the organism strain prior to its transformation. In some variations, a recombinant organism comprises a decrease in level of a particular activated protein species, relative to the organism strain prior to its transformation, wherein the decreased activated protein species is used by a pathway that limits the ability of the recombinant organism to produce a preferred solvent. In some variations the amount of decrease of the activated protein species is 5%, 10%, 15%, 20%, 25%, 30%, 35%, 40%, 45%, 50%, 55%, 60%, 65%, 70%, 75%, 80%, 90%, 95%, 100%, relative to the organism strain prior to its transformation.

In one aspect of the invention, a recombinant organism species produces a particular solvent with increased efficiency. Increased efficiency of solvent production can be determined in any number of ways including but not limited to: concentration (weight/volume) of solvent in fermentation medium, yield (weight/weight) of solvent per amount of substrate, and rate of solvent formation (weight/volume/time).

In one aspect of the invention, a recombinant organism strain is screened for an increased level of a particular solvent, relative to the organism strain prior to its transformation. In some variations, a recombinant organism according to the present invention shows an increased amount of a particular solvent relative to the organism strain prior to its transformation, wherein the amount of the particular solvent is increased at least 1.1, 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.5, 5.0, 5.5, 6.0, 6.5, 7.0, 7.5, 8.0, 8.5, 9.0, 9.5, 10, 15, 20, 40, 60, 80, or 100-fold over that in the organism strain prior to its transformation. Where the concentration of the solvent in the organism strain prior to its transformation is 10 g/L, the concentration of the solvent in the recombinant solventogenic organism strain of the present invention is 11, 12, 13, 14, 15, 16, 17, 18, 19, 20, 22, 24, 26, 28, 30, 32, 34, 36, 38, 40, 45, 50, 55, 60, 65, 70, 75, 80, 85, 90, 95, or 100 g/L In some embodiments of the invention, the solvent concentration in a culture of the recombinant solventogenic organism strain is about 10, 20, 30, 40, 50, or 60 g/L.

In some variations, a recombinant organism strain according to the present invention produces an increased yield of a particular solvent per amount of the substrate, relative to the organism strain prior to its transformation. Where the yield of solvent in the organism strain prior to its transformation is about 20 g/100 g of substrate, a recombinant solventogenic organism strain of the present invention produces yields of: 22, 24, 26, 28, 30, 32, 34, 36, 38, 40, 44, 48, 50, 52, 56, 60, 64, 68, 72, 76, or 80 g solvent per 100 g substrate. In some embodiments of the invention, the yield from a culture of the recombinant solventogenic organism strain is about 24, 30, 40, 50, or 60 g/100 g of substrate.

In some variations, a recombinant organism strain according to the present invention displays an increased rate of formation of a particular solvent, relative to the organism strain prior to its transformation. Where the rate of formation of solvent in the organism strain prior to its transformation is about 0.2 g/L/hour of substrate a recombinant solventogenic organism strain of the present invention produces rates of solvent formation of: 0.24, 0.26, 0.28, 0.3, 0.32, 0.34, 0.36, 0.38, 0.4, 0.44, 0.48, 0.52, 0.56, 0.6, 0.64, 0.68, 0.72, 0.76, 0.8, 0.9, 1, 1.1, 1.2, 1.3, 1.4, 1.5, 1.6, 1.7, 1.8, 1.9, 2, 3, 4, 8, or 12 g/L/hr. In some embodiments of the invention, the rate of solvent formation from a culture of the recombinant solventogenic organism strain is about 0.24, 0.3, 0.4, 0.5, 0.6, 0.7, 0.8, 0.9, 1, 1.2, 1.4, 1.6, 1.8, 2.0, 2.2, 2.4, 2.6, 2.8, or 3.0 g/L/hour.

In some variations, a recombinant organism comprises an increased level of a particular solvent, relative to the organism strain prior to its transformation. In some variations, a recombinant organism comprises an increased level of a particular solvent relative to the organism strain prior to its transformation, wherein the level of the particular solvent is increased at least 0.05%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.9%, 0.95%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.75%, 3%, 3.25%, 3.5%, 3.75%, 4%, 4.25%, 4.5%, or 5%. In some variations, a recombinant organism comprises an increased level of a particular solvent relative to the organism strain prior to its transformation, wherein the level of the particular solvent is increased at least 5%, 10%, 15%, 20%, 25%, 30%, 35%, 40%, 45%, 50%, 55%, 60%, 65%, 70/%, 75%, 80%, 90%, 95%, 100%, 125%, 150%, 175%, 200%, 225%, 250%, 275%, 300%, 325%, 350%, 375%, 400%, 425%, 450%, 475%, 500%, 600%, 700%, 800%, 900%, or 1000%. In some variations, a recombinant organism comprises an increased level of a particular solvent relative to the organism strain prior to its transformation, wherein the level of the particular solvent is increased at least 25%. In some variations, a recombinant organism comprises an increased level of a particular solvent relative to the organism strain prior to its transformation, wherein the level of the particular solvent is increased at least 50%. In some variations, a recombinant organism comprises an increased level of a particular solvent relative to the organism strain prior to its transformation, wherein the level of the particular solvent is increased at least 75%. In some variations, a recombinant organism comprises an increased level of a particular solvent relative to the organism strain prior to its transformation, wherein the level of the particular solvent is increased at least 100%. In some variations, a recombinant organism comprises an increased level of a particular solvent relative to the organism strain prior to its transformation, wherein the level of the particular solvent is increased at least 200%. In some variations, a recombinant organism comprises an increased level of a particular solvent relative to the organism strain prior to its transformation, wherein the level of the particular solvent is increased between 0.05-500%. In some variations, a recombinant organism comprises an increased level of a particular solvent relative to the organism strain prior to its transformation, wherein the level of the particular solvent is increased between 0.05-300%. In some variations, a recombinant organism comprises an increased level of a particular solvent relative to the organism strain prior to its transformation, wherein the level of the particular solvent is increased between 0.5-500%. In some variations, a recombinant organism comprises an increased level of a particular solvent relative to the organism strain prior to its transformation, wherein the level of the particular solvent is increased between 5-500%. In some variations, a recombinant organism comprises an increased level of a particular solvent relative to the organism strain prior to its transformation, wherein the level of the particular solvent is increased between 100-500%. In some variations, a recombinant organism comprises an increased level of a particular solvent relative to the organism strain prior to its transformation, wherein the level of the particular solvent is increased between 10-100%. In some variations, a recombinant organism comprises an increased level of a particular solvent relative to the organism strain prior to its transformation, wherein the level of the particular solvent is increased between 500-1000%. In some variations, the solvent is butanol. In some variations, the solvent is ethanol. In some variations, the solvent is acetone.

In some variations, an organism comprises an increased level of a particular mRNA species. In some variations, a recombinant organism comprises an increased level of a particular mRNA species, relative to the organism strain prior to its transformation. In some variations, a recombinant organism comprises an increased level of a particular mRNA species relative to the organism strain prior to its transformation, wherein the level of the particular mRNA species is increased at least 1.5-fold, 2-fold, 4-fold, 10-fold, 25-fold, 50-fold, or 100-fold relative to the organism strain prior to its transformation. In some variations, a recombinant organism comprises an increased level of a particular mRNA species relative to the organism strain prior to its transformation, wherein the level of the particular mRNA species is increased at least 2-fold. In some variations, a recombinant organism comprises an increased level of a particular mRNA species relative to the organism strain prior to its transformation, wherein the level of the particular mRNA species is increased at least 5-fold. In some variations, a recombinant organism comprises an increased level of a particular mRNA species relative to the organism strain prior to its transformation, wherein the level of the particular mRNA species is increased at least 10-fold. In some variations, a recombinant comprises an increased level of a particular mRNA species relative to the organism strain prior to its transformation, wherein the level of the particular mRNA species is increased at least 15-fold. In some variations, a recombinant organism comprises an increased level of a particular mRNA species relative to the organism strain prior to its transformation, wherein the level of the particular mRNA species is increased at least 20-fold. In some variations, a recombinant organism comprises an increased level of a particular mRNA species relative to the organism strain prior to its transformation, wherein the level of the particular mRNA species is increased at least 40-fold. In some variations, a recombinant organism comprises an increased level of a particular mRNA species relative to the organism strain prior to its transformation, wherein the level of the particular mRNA species is increased at least 60-fold.

In some variations, an organism comprises an increased level of a particular protein species. In some variations, a recombinant organism comprises an increased level of a particular protein species, relative to the organism strain prior to its transformation. In some variations, a recombinant organism comprises an increased level of a particular protein species relative to the organism strain prior to its transformation, wherein the level of the particular protein species is increased at least 1.5-fold, 2-fold, 5-fold, 10-fold, 20-fold, 30-fold, 40-fold, 50-fold, 60-fold, 80-fold, or 100-fold relative to the organism strain prior to its transformation. In some variations, a recombinant organism comprises an increased level of a particular protein species relative to the organism strain prior to its transformation, wherein the level of the particular protein species is increased at least 1.5-fold. In some variations, a recombinant organism comprises an increased level of a particular protein species relative to the organism strain prior to its transformation, wherein the level of the particular protein species is increased at least 5-fold. In some variations, a recombinant organism comprises an increased level of a particular protein species relative to the organism strain prior to its transformation, wherein the level of the particular protein species is increased at least 10-fold. In some variations, a recombinant organism comprises an increased level of a particular protein species relative to the organism strain prior to its transformation, wherein the level of the particular protein species is increased at least 20-fold. In some variations, a recombinant organism comprises an increased level of a particular protein species relative to the organism strain prior to its transformation, wherein the level of the particular protein species is increased at least 40-fold. In some variations, a recombinant organism comprises an increased level of a particular protein species relative to the organism strain prior to its transformation, wherein the level of the particular protein species is increased at least 60-fold. In some variations, a recombinant organism comprises an increased level of a particular protein species relative to the organism strain prior to its transformation, wherein the level of the particular protein species is increased at least 80-fold. In some variations, a recombinant organism comprises an increased level of a particular protein species relative to the organism strain prior to its transformation, wherein the level of the particular protein species is increased at least 100-fold.

In some variations, the amount of a particular protein species in the organism strain prior to its transformation is 0.10 percent of the total protein in a cell. The amount of the particular protein species in the recombinant solventogenic organism strain is about 0.2, 0.5, 1.0, 2.0, 4.0, 6.0, 8.0, 10.0 percent of the total protein in the cell.

In some variations, an organism comprises an increased level of a particular activated protein species. In some variations, a recombinant organism comprises an increased level of a particular activated protein species, relative to the organism strain prior to its transformation. In some variations, a recombinant organism comprises an increased level of a particular activated protein species relative to the organism strain prior to its transformation, wherein the level of the particular activated protein species is increased at least 1.5-fold, 2-fold, 5-fold, 10-fold, 20-fold, 30-fold, 40-fold, 50-fold, 60-fold, 80-fold, or 100-fold relative to the organism strain prior to its transformation. In some variations, a recombinant organism comprises an increased level of a particular activated protein species relative to the organism strain prior to its transformation, wherein the level of the particular activated protein species is increased at least 1.5-fold. In some variations, a recombinant organism comprises an increased level of a particular activated protein species relative to the organism strain prior to its transformation, wherein the level of the particular activated protein species is increased at least 5-fold. In some variations, a recombinant organism comprises an increased level of a particular activated protein species relative to the organism strain prior to its transformation, wherein the level of the particular activated protein species is increased at least 10-fold. In some variations, a recombinant organism comprises an increased level of a particular activated protein species relative to the organism strain prior to its transformation, wherein the level of the particular activated protein species is increased at least 20-fold. In some variations, a recombinant organism comprises an increased level of a particular activated protein species relative to the organism strain prior to its transformation, wherein the level of the particular activated protein species is increased at least 40-fold. In some variations, a recombinant organism comprises an increased level of a particular activated protein species relative to the organism strain prior to its transformation, wherein the level of the particular activated protein species is increased at least 60-fold. In some variations, a recombinant organism comprises an increased level of a particular activated protein species relative to the organism strain prior to its transformation, wherein the level of the particular activated protein species is increased at least 80-fold. In some variations, a recombinant organism comprises an increased level of a particular activated protein species relative to the organism strain prior to its transformation, wherein the level of the particular activated protein species is increased at least 100-fold.

In some variations, the amount of a particular activated protein species in the organism strain prior to its transformation is 0.10 percent of the total protein in a cell. The amount of the particular activated protein species in the recombinant solventogenic organism strain is about 0.2, 0.5, 1.0, 2.0, 4.0, 6.0, 8.0, 10.0 percent of the total protein in the cell.

Modifying Clostridia for Increasing Efficiency of Butanol Production.

U.S. Pat. No. 6,358,717 discloses a method of producing high levels of butanol using a fermentation process that employs a mutant strain of *Clostridium beijerinckii*. *Clostridium beijerinckii* BA101 (ATCC No. PTA-1550) is a hyper-butanol producing strain formed by mutagenesis of the wild type *Clostridium beijerinckii* NCIMB 8052. (Annous, B. A., and H. P. Blaschek. 1991. Isolation and characterization of *Clostridium acetobutylicum* mutants with enhanced amylolytic activity. Appl. Environ. Microbiol. 57:2544-2548; Formanek, J., R. Mackie, and H. P. Blaschek. 1997. Enhanced butanol production by *Clostridium beijerinckii* BA101 grown in semidefined P2 medium containing 6 percent maltodextrin or glucose. Appl. Environ. Microbiol. 63:2306-2310.)

In one aspect of the invention, gene expression profiles of *C. beijerinckii* BA101 and the wild type *C. beijerinckii* NCIMB 8052 are compared. Profiles of expression of solventogenic genes are compared between the hyper-butanol producing *C. beijerinckii* BA101 and the wild type *C. beijerinckii* NCIMB 8052. Typically, gene expression profiles are compared using standard microarray techniques.

Microarrays comprising nucleic acid probes comprising the sequence of one or more genes of *C. beijerinckii* BA101 or the wild type *C. beijerinckii* NCIMB 8052 are arrayed on a surface of the microarray. The genome of the wild type *Clostridium beijerinckii* 8052 is about 6.0 Mbp and the sequence is available at GenBank accession number CP000721; thus probes corresponding to genes of the wild type *C. beijerinckii* NCIMB 8052 are readily obtained. Methods for fabricating and using microarrays is found in U.S. Pat. No. 5,807,522, which is herein incorporated by reference. Instructions for constructing microarray hardware (e.g., arrayers and scanners) using commercially available parts can be found in Cheung et al., 1999, Nat. Genet. Supplement 21:15-19, which are herein incorporated by reference, Additional discussions of microarray technology and protocols for preparing samples and performing microarray experiments are found in M. Schena (ed.), DNA Microarrays: A Practical Approach, Oxford University Press, Oxford, U K, 1999. Descriptions of how to use an arrayer and the associated software can be found on-line.

In a typical microarray experiment, a microarray is hybridized with differentially labeled RNA, DNA, or DNA populations derived from two different samples. Most commonly RNA is isolated from cells or tissues of interest and is reverse transcribed to yield DNA. Labeling is usually performed during reverse transcription by incorporating a labeled nucleotide in the reaction mixture. Although various labels can be used, most commonly the nucleotide is conjugated with the fluorescent dyes Cy3 or Cy5. For example, Cy5-dUTP and Cy3-dUTP can be used. DNA derived from one sample (representing, for example, a particular cell type or growth condition) is labeled with one fluorophore while DNA derived from a second sample (representing, for example, a different or mutant cell type, or growth condition) is labeled with the second fluorophore. Similar amounts of labeled material from the two samples are cohybridized to the microarray. In the case of a microarray experiment in which the samples are labeled with Cy5 (which fluoresces red) and Cy3 (which fluoresces green), the primary data (obtained by scanning the microarray using a detector capable of quantitatively detecting fluorescence intensity) are ratios of fluorescence intensity (red/green, R/G). These ratios represent the relative concentrations of DNA molecules that hybridized to the DNA probes represented on the microarray and thus reflect the relative expression levels of the mRNA corresponding to each DNA probe/gene represented on the microarray.

Differential expression of genes, especially solventogenic genes, are compared between *C. beijerinckii* BA101 and the wild type *C. beijerinckii* NCIMB 8052. In some embodiments, expression profiles are correlated with solvent production and butanol production phases, respectively of *C. beijerinckii* BA101, *C. beijerinckii* NCIMB 8052 or both. Sets of genes that are differentially expressed between the wild type and hyper-butanol mutant are identified. Genes in the hyper-butanol mutant *C. beijerinckii* BA101 show increased or decreased expression relative to genes of the wild type *C. beijerinckii* NCIMB 8052. In one aspect these genes are involved in one or more solvent production-related pathways such as solventogenesis, chemotaxis, motility, sporulation and sugar transport.

In one aspect of the invention, one or more of these genes are identified and their expression profiles corresponding to a hyper-butanol producing state is replicated in a *Clostridium*, preferably in a *Clostridium beijerinckii*. This can be accomplished in a number of ways including, but not limited to, transforming a microorganism such as clostridia with the gene under the control of a constitutive or inducible promoter. The promoter is designed to replicate the increased or decreased gene expression (relative to wild type) observed in the hyper-butanol producing mutant. In one aspect the organism transformed with a wild type gene from *Clostridium beijerinckii* NCIMB 8052, whose genetic (DNA) sequence is publicly available.

In one aspect of the invention, the sequences of *Clostridium beijerinckii* NCIMB 8052 and hyper-butanol producing *Clostridium beijerinckii* BA101 are compared. *Clostridium beijerinckii* BA101 is publicly available (ATCC No. PTA-1550) and may be sequenced using methods known to those of skill in the art. In some variations, a recombinant organism is transformed with one or more genes from *Clostridium beijerinckii* BA101 that has a sequence different from the corresponding gene in *Clostridium beijerinckii* NCIMB 8052. Where the expression of the gene is altered in BA101 relative to the wild-type, a suitable promoter is operably linked to the gene sequence prior to transformation. The promoter is able to be used to replicate the gene expression profile in BA101 in the recombinant organism.

In one aspect of the invention, the genes related to the solvent productions pathways identified by this analysis include homologous genes with at least 70, 75, 80, 83, 85, 90, 95, 97, 99 or 100% homology with the known sequence of a gene in wild type *C. beijerinckii* NCIMB 8052.

In another embodiment of the invention, homologous polynucleotides are identified by the ability to hybridize under moderate to high stringency conditions to a polynucleotide sequence provided herein, or a fragment thereof, or a complementary sequence thereof. Hybridization techniques are well known in the art of molecular biology. High stringency conditions are known in the art. See, for example, Maniatis et al., Molecular Cloning: A Laboratory Manual, 2d Edition, 1989, and Short Protocols in Molecular Biology, ed. Ausubel, et al. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for longer probes (e.g. greater than 50 nucleotides). In another embodiment, less stringent hybridization conditions are used. For example, moderate or low stringency conditions may be used, as are known in the art. (See Maniatis and Ausubel, supra, and Tijssen, supra). For purposes of illustration, suitable moderately stringent conditions for testing the hybridization of a polynucleotide of this invention with other polynucleotides include prewashing in a solution of 5×SSC ("saline sodium citrate"; 9 mM NaCl, 0.9 mM sodium citrate), 0.5% SDS, 1.0 mM EDTA (pH 8.0); hybridizing at 50-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C., or 65-70° C. Stringent conditions may also be achieved with the addition of destabilizing agents such as formamide.

Identification of homologous genes can also be performed by optimal alignment of sequences for comparison to analyze sequence identity (homology) known in the art. Homology in this context means sequence similarity or identity, with identity being preferred. This homology is determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection. One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters include a default gap weight of 3.00, a default gap length weight of 0.10, and weighted end gaps. Another example of a useful algorithm is the BLAST (Basic Local Alignment Search Tool) algorithm, described in Altschul et al., J. Mol. Biol. 215, 403-410, (1990) and Karlin et al., PNAS USA 90:5873-5787 (1993). A particularly useful BLAST program is the WU-BLAST-2 program which was obtained from Altschul et al., Methods in Enzymology, 266: 460-480 (1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A percent amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). Thus, "percent (%) nucleic acid sequence identity" is defined as the percentage of nucleotide residues in a candidate sequence that are identical with the nucleotide residues of a particular nucleic acid. A preferred method utilizes the BLASTN module of WU-BLAST-2 set to the default parameters, with overlap span and overlap fraction set to 1 and 0.125, respectively.

The nucleic acids of the present invention that are identified by altered expression or nucleotide sequence in the hyper-butanol producing clostridia can be used to isolate nucleic acids encoding homologous proteins from other strains of the same or other species and microorganisms, such as Clostridia, *Escherichia, Sachharomyces*, etc. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction). For example, genes encoding homologous proteins, either as DNA's or genomic DNA's, could be isolated directly by using all or a portion of the nucleic acids of the present invention as DNA hybridization probes to screen DNA or genomic libraries from any desired organism employing methodology well known to those skilled in the art. Methods for forming such libraries are well known in the art (Sambrook et al., Molecular Cloning: A Laboratory Manual; Cold Spring Harbor Laboratory Press, Cold Spring Harbor, 1989).

Nucleic acids of interest may also be synthesized, either completely or in part, especially where it is desirable to provide host-preferred sequences, by well-known techniques. See, e.g., Carruthers et al. (Cold Spring Harbor Symp. Quant. Biol. 47:411-418, 1982) and Adams et al. (J. Am. Chem. Soc. 105:661, 1983). Thus, all or a portion of the nucleic acids of the present invention may be synthesized using codons preferred by a selected host.

Genes and homologs and variants thereof that are identified as having a role in hyper-production of butanol can be used for transforming host species or organisms for the high efficiency production of butanol. In one aspect, the nucleic acids used for transformation comprise the sequence of the gene as well as an operably linked constitutive or inducible promoter that can be used to regulate expression of the gene. Specific examples of methods for modifying clostridia for increasing efficiency of butanol production are provided infra.

Methods of Preparing Substrates

In addition to conventional starch (maize, wheat, millet, rye, etc.) or sugar (molasses) substrates saccharolytic clostridia are able to utilize many different carbohydrates. (See Jones and Woods, 1986, supra.) Solvent production starting materials such as biomass, plant-based, cellulosic, lignocellulosic or hemicellulosic materials may be directly entered into the solvent production process. However, often such materials are pretreated to convert lignocellulosic biomass into a form which is more accessible to cellulolytic and fermentation processes. Pretreatment typically includes one or more of increasing the surface area to volume ratio by, for example comminution; steam treatment, acid hydrolysis, or enzymatic treatment. Those of skill in the art are familiar with these and other pretreatment methods.

Methods of Processing Cellulose to Sugars

Cellulosic and hemicellulosic materials may be converted to downstream products such as fermentable sugars by various methods. In some variations, biomass, lignocellulosic, or cellulosic materials are converted to downstream products such as fermentable sugars via a method which does not require living bacteria, yeast, or other organisms.

In some variations, biomass, lignocellulosic, or cellulosic materials are converted to downstream products such as fermentable sugars via a method which utilizes living bacteria, yeast, or other organisms.

In some variations, any organism capable of processing biomass, lignocellulosic, or cellulosic materials to one or more useful downstream products, including but not limited to fermentable sugars, is used in the methods described herein. In some variations, any organism capable of processing cellulose to one or more useful downstream products, including but not limited to fermentable sugars, is used in the methods described herein.

In some variations, a cellulolytic yeast, bacteria or other organism, including but not limited to Clostridia, *Saccharomyces*, or *Escherichia* strains, are naturally or through genetic manipulation made capable of processing biomass, lignocellulosic, or cellulosic materials to one or more useful downstream products, including but not limited to fermentable sugars.

In some variations, a solventogenic organism is transformed with one or more genes or regulatory sequences controlling expression of a gene relating to the conversion of biomass, lignocellulosic, or cellulosic materials to one or more useful downstream products, including but not limited to fermentable sugars.

In some variations, a solventogenic organism is transformed with one or more heterologous genes or heterologous regulatory sequences controlling a gene relating to the conversion of biomass, lignocellulosic, or cellulosic materials to one or more useful downstream products, including but not limited to fermentable sugars.

In some variations, a solventogenic organism is transformed with one or more genes relating to activation or inactivation of a gene product involved in the conversion of biomass, lignocellulosic, or cellulosic materials to one or more useful downstream products, including but not limited to fermentable sugars.

In some variations, a solventogenic organism is transformed with one or more cellulolytic genes. In some variations, a solventogenic organism is transformed with one or more genes involved in generating a functional cellulosome complex. In some variations, a solventogenic organism is transformed with all of the genes involved in a cellulosome complex.

In some variations, a solventogenic organism is transformed with one or more secretable cellulolytic genes. In some variations, a non-solventogenic organism is transformed with one or more secretable cellulolytic genes. In some variations, a solventogenic organism is transformed with one or more secretable cellulolytic genes. In some variations, a solventogenic organism is transformed with all of the secretable cellulolytic genes necessary to convert biomass, lignocellulosic, or cellulosic materials to one or more useful downstream products, including but not limited to fermentable sugars.

In some variations, a solventogenic organism is transformed with one or more cellulolytic genes. In some variations, a solventogenic organism is transformed with one or more genes involved in generating a functional cellulosome complex. In some variations, a solventogenic organism is transformed with all of the genes involved in a cellulosome complex.

In some variations, a solventogenic organism is transformed with one or more genes encoding one or more enzymes that cut at random at internal amorphous sites in a cellulose polysaccharide chain. In some variations, a solventogenic organism is transformed with one or more genes encoding one or more endoglucanases or 1,4-beta-D-glucan-4-glucanohydrolases.

In some variations, a solventogenic organism is transformed with one or more genes encoding one or more enzymes that process reducing or nonreducing ends of cellulose polysaccharide chains to hexoses such as glucose, or cellobiose. In some variations, a solventogenic organism is transformed with one or more genes encoding one or more exoglucanases. In some variations, a solventogenic organism is transformed with one or more genes encoding one or more 1,4-beta-D-glucan glucanohydrolases, cellodextrinases, 1,4-beta-D-glucan cellobiohydrolases, or cellobiohydrolases.

In some variations, a solventogenic organism is transformed with one or more genes encoding one or more beta-glucosidases or beta-glucoside glucohydrolases.

In some variations, a solventogenic organism is transformed with one or more genes encoding one or more scaffoldin-type proteins.

In some variations, a solventogenic organism is transformed with one or more genes or regulatory sequences which decrease or impair the activity of one or more pathways which decrease or impair the solventogenic potential of a solventogenic organism. In some variations, a solventogenic organism is transformed with one or more heterologous genes or heterologous regulatory sequences which decrease or impair the activity of one or more pathways which decrease or impair the solventogenic potential of a solventogenic organism. In some variations, a solventogenic organism is transformed with one or more genes or regulatory sequences which decrease or impair the activity of one or more pathways which decrease or impair the solventogenic potential of a *Clostridium* strain, including but not limited to *C. beijerinckii* or *C. beijerinckii* BA101.

Methods of Generating Solvents from Sugars

Cellulosic materials are typically converted into a mixture of hexose sugars, such as glucose and mannose, and pentose sugars, such as xylose and arabinose. These sugars may then be acted upon to generate one or more solvents.

In some variations, the organisms described herein are optimized to ferment one or more hexose or pentose sugars to solvents, for example butanol, ethanol, or acetone. In some variations, the organisms described herein are optimized to ferment all major hexose or pentose sugars to solvents. In some variations, the organisms described herein are optimized to ferment one or more of glucose, mannose, xylose or arabinose. In some variations, the organisms described herein are optimized to ferment glucose. In some variations, the organisms described herein are optimized to ferment mannose. In some variations, the organisms described herein are optimized to ferment xylose. In some variations, the organisms described herein are optimized to ferment arabinose.

In some variations the organism that converts one or more hexose or pentose sugars to a solvent, including but not limited to butanol, is also capable of converting cellulosic material to hexose or pentose sugars, with or without pretreatment.

In some variations the organism that converts one or more hexose or pentose sugars to a solvent, including but not limited to butanol, is not capable of converting cellulosic material to hexose or pentose sugars, with or without pretreatment.

In some variations the process utilizing an organism that converts one or more hexose or pentose sugars to a solvent, including but not limited to butanol, includes simultaneous or sequential use of a second organism or strain that is capable of converting cellulosic material to hexose or pentose sugars, with or without pretreatment.

In some variations, the organisms described herein are optimized to ferment one or more hexose or pentose sugars by increasing or facilitating the organism's use of favored pathways. In some variations, the organisms described herein are optimized to ferment one or more of glucose, mannose, xylose or arabinose by increasing or facilitating the organism's use of favored pathways.

In some variations, the organisms described herein are optimized to ferment one or more hexose or pentose sugars by decreasing or impairing use of pathways which decrease or impair production of a solvent of interest. In some variations, the organisms described herein are optimized to ferment one or more of glucose, mannose, xylose or arabinose by decreasing or impairing use of pathways which decrease or impair production of a solvent of interest.

In some variations, an organism described herein is transformed with one or more genes involved in the metabolic pathway of a particular hexose or pentose sugar. In some variations, an organism described herein is transformed with all genes involved in the metabolic pathway of a particular hexose or pentose sugar. In some variations, an organism described herein is transformed with one or more genes involved in the metabolic pathway of glucose. In some variations, an organism described herein is transformed with all genes involved in the metabolic pathway of glucose. In some variations, an organism described herein is transformed with one or more genes involved in the metabolic pathway of mannose. In some variations, an organism described herein is transformed with all genes involved in the metabolic pathway of mannose. In some variations, an organism described herein is transformed with one or more genes involved in the metabolic pathway of xylose. In some variations, an organism described herein is transformed with all genes involved in the metabolic pathway of xylose. In some variations, an organism described herein is transformed with one or more genes involved in the metabolic pathway of arabinose. In some variations, an organism described herein is transformed with all genes involved in the metabolic pathway of arabinose.

In some variations, an organism described herein is transformed with one or more genes involved in the metabolic pathway of a particular hexose or pentose sugar from a bacteria. In some variations, an organism described herein is transformed with one or more genes involved in the metabolic pathway of a particular hexose or pentose sugar from a *Neurospora* strain, including but not limited to *N. crassa*.

In some variations, the titer, yield and productivity of solvent production is increased by optimizing the various metabolic pathways involved in the biosynthesis of one or more solvents of interest, including but not limited to butanol, ethanol, and acetone. In some variations, the titer, yield and productivity of butanol production is increased by optimizing the various metabolic pathways involved in the biosynthesis of butanol. In some variations, metabolic flux analysis is used to identify the rate-limiting steps in solvent synthesis in an organism described herein, including but not limited to a *Clostridium* or *S. cerevisiae* strain.

By way of nonlimiting example, for a linear pathway, the level of final product is related to the overall flux through the pathway. An optimized solvent biosynthetic pathway should have increased overall flux through the pathway without significant accumulation of pathway intermediates. Various analytical instruments may be used to determine the concentrations of key metabolites in the metabolic pathways involved in the biosynthesis of the solvent at fermentation conditions and identify the rate-limiting enzymes. Non-limiting examples of analytical instruments include GC-MS. HPLC-MS, HPLC (stand alone), Piezorray robotic printer (non-contact microarray printing onto membranes, plates, and slides), UV/visible/fluorescence microplate reader, and chemiluminometer microplate reader. To trace the metabolites, C-14 based isotopic labeling methods in combination with either LC-MS or NMR may be used.

Once the rate-limiting enzymes are identified in an organism described herein, overexpression of the one or more genes limiting the overall flux may be used to determine its effect on the concentrations of pathway intermediates and the final solvent product. If the product concentration is increased, then the overexpressed gene or genes are indeed positively correlated with solvent production. Non-limiting examples of strategies to balance gene expression include manipulation of promoter strength, ribosomal binding site (RBS) strength, gene location in an operon, and mRNA stability.

The effect of various sporulation, motility, and sugar transport genes may be similarly evaluated. For example, increasing or decreasing the expression of one or more genes relating to sporulation, motility, and sugar transport may be used to determine their effect on the concentrations of pathway intermediates and the final solvent product. If the product concentration is increased, then the gene or genes with increased or decreased expression are correlated with solvent production. Non-limiting examples of strategies to balance gene expression include manipulation of promoter strength, ribosomal binding site (RBS) strength, gene location in an operon, and mRNA stability.

Solventogenic Genes

Acid concentration and reducing state are also known to influence the production of solvents and hence, impact the expression of solvent-related genes in *Clostridium*. Genes involved in solvent production and butanol production are identified in FIG. 9.

As demonstrated in FIG. 4, alcohol dehydrogenase (Adh), butyryl-CoA dehydrogenase (Bcd) and butyrate kinase (Buk) are expressed at altered (higher or lower) levels during the solventogenic stage in BA101 compared with the wild-type *C. beijerinckii* strain.

In some variations, an organism described herein is optimized to increase production of an enzyme in the solventogenic pathway. In some variations, an organism described herein is transformed with a gene encoding an enzyme in the solventogenic pathway. In some variations an organism described herein is transformed with a gene encoding an enzyme in the solventogenic pathway to overexpress the enzyme.

In some variations, an organism described herein is optimized to increase production of all of the enzymes described herein in the butanol solventogenic pathway. In some variations, an organism described herein is transformed with all of the enzymes described herein in the butanol solventogenic pathway. In some variations an organism described herein is transformed with a gene encoding all of the enzymes described herein in the butanol solventogenic pathway to overexpress the enzymes.

Alcohol dehydrogenase (Adh) encodes an important terminal enzyme required for alcohol production. Thus, increased Adh expression may directly contribute to elevated butanol synthesis in BA101. In some variations, an organism described herein is optimized to increase production of Adh. In some variations, an organism described herein is transformed with an Adh gene. In some variations an organism described herein is transformed with an Adh gene to overexpress Adh. In some variations, an organism described herein is transformed with an Adh gene from a microbial organism to overexpress Adh. In some variations, an organism described herein is transformed with an Adh gene from a *Clostridium* sp. to overexpress Adh. In some variations, an organism described herein is transformed with an Adh gene from *Clostridium beijerinckii* to overexpress Adh. In some variations, an organism described herein is transformed with a nucleic acid which results in an increase in expression of the Adh gene whose DNA sequence is shown in FIG. 10. In some variations, an organism described herein is transformed with an Adh gene whose DNA sequence is shown in FIG. 10 to overexpress Adh.

In some variations, an organism described herein is transformed with an Adh gene whose DNA sequence is at least 60-100% identical to the DNA sequence shown in FIG. 10 or complement thereof. In some variations, an organism described herein is transformed with an Adh gene whose DNA sequence is at least 80-100% identical to the DNA sequence shown in FIG. 10 or complement thereof. In some variations, an organism described herein is transformed with an Adh gene whose DNA sequence is at least 90-100% identical to the DNA sequence shown in FIG. 10 or complement thereof. In some variations, an organism described herein is transformed with an Adh gene whose DNA sequence is at least 60, at least 65, at least 70, at least 75, at least 80, at least 85, at least 90, at least 95, or 100% identical to the DNA sequence shown in FIG. 10 or complement thereof. In some variations, an organism described herein is transformed with an Adh gene whose DNA sequence is at least 80% identical to the DNA sequence shown in FIG. 10 or complement thereof. In some variations, an organism described herein is transformed with an Adh gene whose DNA sequence is at least 85% identical to the DNA sequence shown in FIG. 10 or complement thereof. In some variations, an organism described herein is transformed with an Adh gene whose DNA sequence is at least 90% identical to the DNA sequence shown in FIG. 10 (SEQ ID NO: 1) or complement thereof. The *Clostridium beijerinckii* NCIMB 8052 published genome identifies this adh gene as Cbei_2181.

The *C. beijerinckii* NCIMB 8052 published genome identifies the adh gene shown in FIG. 10 as Cbei_2181 (SEQ ID NO: 1). NCBI BLAST search against the *C. beijerinckii* NCIMB 8052 genome revealed another *C. beijerinckii* NCIMB 8052 gene that is a close homolog of Cbei_2181 at both the DNA sequence and the protein sequence levels. The DNA sequence (SEQ ID NO: 14) is shown in FIG. 22A and predicted amino acid sequence (SEQ ID NO: 15) of Cbei_1722 is shown in FIG. 22B.

At the DNA level the Cbei_1722 adh gene shows 90% identity to Cbei_2181 with 1% gaps in the alignment. At the protein level the Cbei_1722 adh protein shows 93% amino acid identity to Cbei_2181, with 97% similarity and zero gaps. The DNA and protein alignments both show an "Expect value" of zero, suggesting the two enzymes are either functionally equivalent, or nearly so. The Cbei_1722 adh gene is annotated at an "iron-containing alcohol dehydrogenase". Multiple isozymes of the class of adh enzymes are known to exist in solvent-forming *Clostridium* species and are known to be induced or de-repressed near the onset of solvent formation (Walter K A, Bennett G N, Papoutsakis E T; Molecular characterization of two *Clostridium acetobutylicum* ATCC 824 butanol dehydrogenase isozyme genes; J Bacteriol. 1992 November; 174(22):7149-58). It is postulated that Cbei_1722 could be used in the same manner as the Cbei_2181 adh gene.

Butyryl-CoA dehydrogenase (Bcd) catalyzes the formation of butyryl-CoA, an immediate precursor for butanol. Higher Bcd expression in BA101 may lead to increased butyryl-CoA production, which in turn may improve the formation of butanol. In some variations, an organism described herein is optimized to increase production of Bcd. In some variations, an organism described herein is transformed with a Bcd gene. some variations an organism described herein is transformed with a Bcd gene to overexpress Bcd. In some variations, an organism described herein is transformed with a Bcd gene from a microbial organism to overexpress Bcd. In some variations, an organism described herein is transformed with a Bcd gene from a *Clostridium* sp. to overexpress Bcd. In some variations, an organism described herein is transformed with a Bcd gene from *Clostridium beijerinckii* to overexpress Bcd. In some variations, an organism described herein is transformed with a nucleic acid which results in an increase in expression of the Bcd gene whose DNA sequence is shown in FIG. 11. In some variations, an organism described herein is transformed with a Bcd gene whose DNA sequence is shown in FIG. 11 (SEQ ID NO: 2) to overexpress Bcd. The *Clostridium beijerinckii* NCIMB 8052 published genome identifies this bed gene as Cbei_2035.

In some variations, an organism described herein is transformed with a Bcd gene whose DNA sequence is at least 60-100% identical to the DNA sequence shown in FIG. 11 or complement thereof. In some variations, an organism described herein is transformed with a Bcd gene whose DNA sequence is at least 80-100% identical to the DNA sequence shown in FIG. 11 or complement thereof. In some variations, an organism described herein is transformed with a Bcd gene whose DNA sequence is at least 90-100% identical to the DNA sequence shown in FIG. 11 or complement thereof. In some variations, an organism described herein is transformed with a Bcd gene whose DNA sequence is at least 60, at least 65, at least 70, at least 75, at least 80, at least 85, at least 90, at least 95, or 100% identical to the DNA sequence shown in FIG. 11 or complement thereof. In some variations, an organism described herein is transformed with a Bcd gene whose DNA sequence is at least 80% identical to the DNA sequence shown in FIG. 11 or complement thereof. In some variations, an organism described herein is transformed with a Bcd gene whose DNA sequence is at least 85% identical to the DNA sequence shown in FIG. 11 or complement thereof. In some variations, an organism described herein is transformed with a Bcd gene whose DNA sequence is at least 90% identical to the DNA sequence shown in FIG. 11 or complement thereof.

The *C. beijerinckii* NCIMB 8052 published genome identifies the bed gene shown in FIG. 11 as Cbei_2035 (SEQ ID NO:2). Other genes identified in the *C. beijerinckii* NCIMB 8052 published genome that are close homologs of the bcd gene Cbei_2035 (SEQ ID NO:2) include Cbei_0322. The DNA sequence of Cbei_0322 (SEQ ID NO: 12) shown in FIG. 21A and the protein sequence of Cbei_0322 (SEQ ID NO: 13) shown in FIG. 21B.

Cbei_0322 shows 98% identity to Cbei_2035 at the DNA level and 98% identity at the protein sequence level, with no gaps. The close homology suggests that gene Cbei_0322 could show Bcd activity. Cbei_0322 is annotated as a "acyl-CoA dehydrogenase domain protein" which is consistent with its being a bed gene. Cbei_2035 (SEQ ID NO:2) is also annotated as "acyl-CoA dehydrogenase domain protein" in the GenBank record. While it is possible that the native role of the Cbei_0322 protein may be in a pathway other than solvent production, such as for instance the metabolism of other fatty acids, its close homology to Cbei_2035 suggests that even if that were true, it could be used as a functional Bcd gene under the control of an appropriate promoter.

Butyrate kinase (Buk) is a key enzyme in butyrate synthesis. Increased Buk activity in BA101 may allow the generation of higher amounts of butyrate, which can then be converted into butyryl-CoA and further into butanol. In some variations, an organism described herein is optimized to increase production of Buk. In some variations, an organism described herein is transformed with a Buk gene. In some variations an organism described herein is transformed with a Buk gene to overexpress Buk. In some variations, an organism described herein is transformed with a Buk gene from a microbial organism to overexpress Buk. In some variations, an organism described herein is transformed with a Buk gene from a *Clostridium* sp. to overexpress Buk. In some variations, an organism described herein is transformed with a Buk gene from *Clostridium beijerinckii* to overexpress Buk. In some variations, an organism described herein is transformed with a nucleic acid which results in an increase in expression of the Buk gene whose DNA sequence is shown in FIG. 12. In some variations, an organism described herein is transformed with a Buk gene whose DNA sequence is shown in FIG. 12 to overexpress Buk.

In some variations, an organism described herein is transformed with a Buk gene whose DNA sequence is at least 60-100% identical to the DNA sequence shown in FIG. 12 or complement thereof. In some variations, an organism described herein is transformed with a Buk gene whose DNA sequence is at least 80-100% identical to the DNA sequence shown in FIG. 12 or complement thereof. In some variations, an organism described herein is transformed with a Buk gene whose DNA sequence is at least 90-100% identical to the DNA sequence shown in FIG. 12 or complement thereof. In some variations, an organism described herein is transformed with a Buk gene whose DNA sequence is at least 60, at least 65, at least 70, at least 75, at least 80, at least 85, at least 90, at least 95, or 100% identical to the DNA sequence shown in FIG. 12 or complement thereof. In some variations, an organism described herein is transformed with a Buk gene whose DNA sequence is at least 80% identical to the DNA sequence shown in FIG. 12 or complement thereof. In some variations, an organism described herein is transformed with a Buk gene whose DNA sequence is at least 85% identical to the DNA sequence shown in FIG. 12 or complement thereof. In some variations, an organism described herein is transformed with a Buk gene whose DNA sequence is at least 90% identical to the DNA sequence shown in FIG. 12 or complement thereof.

In some variations, an organism described herein is optimized to increase expression of any one or more of Adh, Bcd, or Buk. In some variations, an organism described herein is transformed with a genes encoding any one or more of Adh, Bcd, or Buk. In some variations an organism described herein is transformed with genes encoding each of Adh, Bcd, and Buk to overexpress Adh, Bcd, and Buk. In some variations an organism described herein is transformed with a nucleic acid which increases expression of any one or more of Adh, Bcd, or Buk.

Genes of Solvent Production Pathway

As demonstrated in FIG. 8, expression of aceto-acetyl CoA:acetate-butyrate CoA transferase subunit $\alpha/\beta$ (CtfA/B) and acetoacetate decarboxylase (Adc) was highly activated at the onset of solventogenic phase in BA101 and the wild-type strain. Changes in expression levels were much smaller for thiolase (Thl), 3-hydroxybutyryl-CoA dehydrogenase (Hcd) and crotonase (Crt) in BA101 and the wild-type strain.

Despite the somewhat comparable expression kinetics of CtfA/B, Adc, Thl, Hcd and Crt in the BA101 strain relative to the wild type parent, altering (increasing or decreasing) the expression of these genes may prove useful in increasing solvent production in the organisms described herein.

In some variations, an organism described herein is optimized to increase production of one or more solvents by changing the expression of any one or more of CtfA/B, Adc, Thl, Hcd and Crt. In some variations, an organism described herein is optimized to increase production of one or more solvents by increasing the expression of one or more of CtfA/B, Adc, Thl, Hcd and Crt. In some variations, an organism described herein is optimized to increase production of one or more solvents by decreasing the expression of one or more of CtfA/B, Adc, Thl, Hcd and Crt. In some variations, an organism described herein is transformed with genes encoding any one or more of CtfA/B, Adc, Thl, Hcd and Crt.

In some variations, an organism described herein is optimized to decrease production of one or more gene products which compete with or are otherwise detrimental to the production of solvents. In some variations an organism described herein is transformed with a nucleic acid to decrease or impair expression of one or more gene products which compete with or are otherwise detrimental to the production of solvents.

In some variations an organism described herein is transformed with a nucleic acid to decrease or impair expression of Adc. In some variations an organism described herein is transformed with a nucleic acid to increase expression of Adc. In some variations, an organism described herein is transformed with an Adc gene from a microbial organism to overexpress Adc. In some variations, an organism described herein is transformed with an Adc gene from a *Clostridium* sp. to overexpress Adc. In some variations, an organism described herein is transformed with an Adc gene from *Clostridium beijerinckii* to overexpress Adc.

In some variations, an organism described herein is transformed with an Adc gene whose DNA sequence is at least 60-100% identical to that of the *Clostridium beijerinckii* NCIMB 8052 gene. In some variations, an organism described herein is transformed with an Adc gene whose DNA sequence is at least 60-100% identical to that of the *Clostridium beijerinckii* BA101 gene. In some variations, an organism described herein is transformed with an Adc gene whose DNA sequence is at least 60, at least 65, at least 70, at least 75, at least 80, at least 85, at least 90, at least 95, or 100% identical to that of the *Clostridium beijerinckii* NCIMB 80 gene. In some variations, an organism described herein is transformed with an Adc gene whose DNA sequence is at least 60, at least 65, at least 70, at least 75, at least 80, at least 85, at least 90, at least 95, or 100% identical to that of the *Clostridium beijerinckii* BA101 gene.

In some variations an organism described herein is transformed with a nucleic acid to decrease or impair expression of CtfA/B. In some variations an organism described herein is transformed with a nucleic acid to increase expression of CtfA/B. In some variations, an organism described herein is transformed with a CtfA/B gene from a microbial organism to overexpress CtfA/B. In some variations, an organism described herein is transformed with a CtfA/B gene from a *Clostridium* sp. to overexpress CtfA/B. In some variations, an organism described herein is transformed with a CtfA/B gene from *Clostridium beijerinckii* to overexpress CtfA/B.

In some variations, an organism described herein is transformed with a CtfA/B gene whose DNA sequence is at least 60-100% identical to that of the *Clostridium beijerinckii* NCIMB 8052 gene. In some variations, an organism described herein is transformed with a CtfA/B gene whose DNA sequence is at least 60-100% identical to that of the *Clostridium beijerinckii* BA101 gene. In some variations, an organism described herein is transformed with a CtfA/B gene whose DNA sequence is at least 60, at least 65, at least 70, at least 75, at least 80, at least 85, at least 90, at least 95, or 100% identical to that of the *Clostridium beijerinckii* NCIMB 80 gene. In some variations, an organism described herein is transformed with a CtfA/B gene whose DNA sequence is at least 60, at least 65, at least 70, at least 75, at least 80, at least 85, at least 90, at least 95, or 100% identical to that of the *Clostridium beijerinckii* BA101 gene.

In some variations an organism described herein is transformed with a nucleic acid to decrease or impair expression of a gene product leading to production of a solvent other than butanol. In some variations an organism described herein is transformed with a nucleic acid to decrease or impair expression of a gene product leading to production of a solvent other than ethanol. In some variations an organism described herein is transformed with a nucleic acid to decrease or impair expression of a gene product leading to production of a solvent other than acetone.

Sugar Transport Genes

As demonstrated in FIG. 5, sugar transporters in the phosphoenolpyruvate-dependent phosphoryltransferase system (PTS) are down-regulated in BA101 relative to the wild-type strain. BA101 shows significantly lower expression of mannose-type PTS components ManIIAB and ManIIC, which mediate broad spectrum sugar uptake across the cell membrane.

In some variations, an organism described herein is optimized to decrease production of a gene product relating to one or more specific sugar transporters. In some variations, an organism described herein is transformed with a gene that decreases or knocks out the expression or activity of a gene product relating to one or more specific sugar transporters.

In some variations, an organism described herein is optimized to decrease production of all of the gene products described herein relating to one or more specific sugar transporters. In some variations, an organism described herein is transformed with a gene that decreases or knocks out the expression or activity of all of the gene products described herein relating to one or more specific sugar transporters.

In some variations, an organism described herein is optimized to decrease production of ManIIAB. In some variations, an organism described herein is transformed with a nucleic acid to decrease expression of a ManIIAB gene. In some variations an organism described herein is transformed with a nucleic acid to decrease expression of a ManIIAB gene via antisense, siRNA, or DNAzyme technology. In some variations, an organism described herein is transformed with a gene from a microbial organism to decrease expression of ManIIAB. In some variations, an organism described herein is transformed with a gene from a *Clostridium* sp. to decrease expression of ManIIAB. In some variations, an organism described herein is transformed with a gene from *Clostridium beijerinckii* to decrease expression of ManIIAB. In some variations, an organism described herein is transformed with a nucleic acid which results in a decrease in expression of the ManIIAB gene whose DNA sequence is shown in FIG. 16.

In some variations, an organism described herein is optimized to decrease production of ManIIC. In some variations, an organism described herein is transformed with a ManIIC gene. In some variations an organism described herein is transformed with a ManIIC gene to overexpress ManIIC.

In some variations, an organism described herein is optimized to decrease production of ManIIC. In some variations, an organism described herein is transformed with a nucleic acid to decrease expression of a ManIIC gene. In some variations an organism described herein is transformed with a nucleic acid to decrease expression of a ManIIC gene via antisense, siRNA, or DNAzyme technology. In some variations, an organism described herein is transformed with a gene from a microbial organism to decrease expression of ManIIC. In some variations, an organism described herein is transformed with a gene from a *Clostridium* sp. to decrease expression of ManIIC. In some variations, an organism described herein is transformed with a gene from *Clostridium beijerinckii* to decrease expression of ManIIC. In some variations, an organism described herein is transformed with a nucleic acid which results in a decrease in expression of the ManIIC gene whose DNA sequence is shown in FIG. 17.

Sporulation Genes

Sporulation genes are activated as cells reach stationary phase and enter solventogenic stage. Sporulation is generally believed to be necessary for solvent formation. As demonstrated in FIG. 6, among a cascade of sporulation events, BA101 is found defective in late stage sporulation. In contrast to large fold induction in the wild-type, activation is much weaker in BA101 for genes encoding sporulation proteins necessary for the completion of spore formation and spore stability. These proteins include spore coat assembly protein SpoIV, spore cortex synthesis protein SpoVB and spore DNA packaging protein SspA. Deficiency in sporulation possibly prolongs the clostridial form and thereby allows extended solventogenesis in BA101, which may give rise to enhanced butanol formation.

In some variations, an organism described herein is optimized to decrease production of a gene product relating to sporulation. In some variations, an organism described herein is transformed with a gene that decreases or knocks out the expression or activity of a gene product relating to sporulation.

In some variations, an organism described herein is optimized to decrease production of all of the gene products described herein relating to sporulation. In some variations, an organism described herein is transformed with a gene that decreases or knocks out the expression or activity of all of the gene products described herein relating to sporulation.

In some variations, an organism described herein is optimized to decrease production of SpoIVA. In some variations, an organism described herein is transformed with a gene that decreases or knocks out the expression or activity of SpoIVA. In some variations, an organism described herein is transformed with a nucleic acid to decrease expression of a SpoIVA gene. In some variations an organism described herein is transformed with a nucleic acid to decrease expression of a ManIIAB gene via antisense, siRNA, or DNAzyme technology. In some variations, an organism described herein is transformed with a nucleic acid sequence from a microbial organism to decrease expression of SpoIVA. In some variations, an organism described herein is transformed with a gene from a *Clostridium* sp. to decrease expression of SpoIVA. In some variations, an organism described herein is transformed with a gene from *Clostridium beijerinckii* to decrease expression of SpoIVA. In some variations, an organism described herein is transformed with a nucleic acid which results in a decrease in expression of the SpoIVA gene whose DNA sequence is shown in FIG. 18.

In some variations, an organism described herein is optimized to decrease production of SpoVB. In some variations, an organism described herein is transformed with a gene that decreases or knocks out the expression or activity of SpoVB. In some variations, an organism described herein is transformed with a nucleic acid to decrease expression of a SpoVB gene. In some variations an organism described herein is transformed with a nucleic acid to decrease expression of a ManIIAB gene via antisense, siRNA, or DNAzyme technology. In some variations, an organism described herein is transformed with a gene from a *Clostridium* sp. to decrease expression of SpoVB. In some variations, an organism described herein is transformed with a gene from *Clostridium beijerinckii* to decrease expression of SpoVB. In some variations, an organism described herein is transformed with a nucleic acid which results in a decrease in expression of the SpoVB gene whose DNA sequence is shown in FIG. 19.

In some variations, an organism described herein is optimized to decrease production of SspA. In some variations, an organism described herein is transformed with a gene that decreases or knocks out the expression or activity of SspA. In some variations, an organism described herein is transformed with a nucleic acid to decrease expression of an SspA gene. In some variations an organism described herein is transformed with a nucleic acid to decrease expression of an SspA gene via antisense, siRNA, or DNAzyme technology. In some variations an organism described herein is transformed with an antisense nucleic acid to decrease expression of an SspA gene. In some variations, an organism described herein is transformed with a nucleic acid sequence from a microbial organism to decrease expression of SspA. In some variations, an organism described herein is transformed with a gene from a *Clostridium* sp. to decrease expression of SspA. In some variations, an organism described herein is transformed with a gene from *Clostridium beijerinckii* to decrease expression of SspA. In some variations, an organism described herein is transformed with a nucleic acid which results in a decrease in expression of the SspA gene whose DNA sequence is shown in FIG. 20 (SEQ ID NO: 11). The *Clostridium beijerinckii* NCIMB 8052 published genome identifies this SspA gene as Cbei_3080.

In some variations, an organism described herein is transformed with a SspA gene whose DNA sequence is at least 60-100% identical to the DNA sequence shown in FIG. 20 or complement thereof. In some variations, an organism described herein is transformed with a SspA gene whose DNA sequence is at least 80-100% identical to the DNA sequence shown in FIG. 20 or complement thereof. In some variations, an organism described herein is transformed with a SspA gene whose DNA sequence is at least 90-100% identical to the DNA sequence shown in FIG. 20 or complement thereof. In some variations, an organism described herein is transformed with a SspA gene whose DNA sequence is at least 60, at least 65, at least 70, at least 75, at least 80, at least 85, at least 90, at least 95, or 100% identical to the DNA sequence shown in FIG. 20 or complement thereof. In some variations, an organism described herein is transformed with a SspA gene whose DNA sequence is at least 80% identical to the DNA sequence shown in FIG. 20 or complement thereof. In some variations, an organism described herein is transformed with a SspA gene whose DNA sequence is at least 85% identical to the DNA sequence shown in FIG. 20 or complement thereof. In some variations, an organism described herein is transformed with a SspA gene whose DNA sequence is at least 90% identical to the DNA sequence shown in FIG. 20 or complement thereof.

The *C. beijerinckii* NCIMB 8052 published genome identifies the SspA gene shown in FIG. 20 as Cbei_3080 (SEQ ID NO: 11). It is annotated in GenBank as a "small acid-soluble spore protein, alpha/beta type."

Other genes identified in the *C. beijerinckii* NCIMB 8052 published genome that are close homologs of the sspA gene Cbei_3080 (SEQ ID NO: 11) include Cbei_3111 and Cbei_3250. They belong to a family of highly conserved spore proteins that are present in this organism and are annotated with the same function—"small acid-soluble spore protein alpha/beta type"—as is Cbei_3080 (SEQ ID NO: 11) shown in FIG. 20. At the protein sequence level Cbei_3111 is 98% similar and 91% identical to Cbei_3080. Cbei_3250 is 94% similar and 91% identical.

The utility of Cbei_3111 and Cbei_3250 would be the same as that taught for Cbei_3080 in the patent, which is to reduce or eliminate their expression through a variety of methods.

The DNA sequence of Cbei_3111 (SEQ ID NO: 16) shown in FIG. 23A and the protein sequence of Cbei_3111 (SEQ ID NO: 17) shown in FIG. 23B.

The DNA sequence of Cbei_3250 (SEQ ID NO: 18) shown in FIG. 24A and the protein sequence of Cbei_3250 (SEQ ID NO: 19) shown in FIG. 24B.

Chemotaxis Genes

As demonstrated in FIG. 7, BA101 has higher expression of chemotaxis and motility genes than the wild-type strain. Genes in a chemotaxis operon CheA, CheC, CheD and CheW become repressed in the wild-type during the solventogenic phase, while their expression levels remain stable in BA101. As highly solventogenic clostridia are generally associated with high motility, BA101 appears to remain in a motile form which may be favorable to solvent production.

In some variations, an organism described herein is optimized to increase production of one or more chemotaxis or motility genes. In some variations, an organism described herein is transformed with a gene encoding one or more chemotaxis or motility genes. In some variations an organism described herein is transformed with a gene encoding one or more chemotaxis or motility genes to overexpress one or more of the chemotaxis or motility genes.

In some variations, an organism described herein is optimized to increase production of all of the chemotaxis or motility genes described herein. In some variations, an organism described herein is transformed with genes encoding all of the chemotaxis or motility genes described herein. In some variations an organism described herein is transformed with genes encoding all of the chemotaxis or motility genes described herein to overexpress all of the chemotaxis or motility genes described herein.

In some variations, an organism described herein is optimized to increase production of CheA. In some variations, an organism described herein is transformed with a CheA gene. In some variations an organism described herein is transformed with a CheA gene to overexpress CheA. In some variations, an organism described herein is optimized to increase production of CheA in the solventogenic phase. In some variations, an organism described herein is transformed with a CheA gene. In some variations an organism described herein is transformed with a CheA gene to overexpress CheA in the solventogenic phase. In some variations, an organism described herein is transformed with a CheA gene from a microbial organism to overexpress CheA. In some variations, an organism described herein is transformed with a CheA gene from a *Clostridium* sp. to overexpress CheA. In some variations, an organism described herein is transformed with a CheA gene from *Clostridium beijerinckii* to overexpress CheA. In some variations, an organism described herein is transformed with a nucleic acid which results in an increase in expression of the CheA gene whose DNA sequence is shown in FIG. 13. In some variations, an organism described herein is transformed with a CheA gene whose DNA sequence is shown in FIG. 13 to overexpress CheA.

In some variations, an organism described herein is transformed with a CheA gene whose DNA sequence is at least 60-100% identical to the DNA sequence shown in FIG. 13 or complement thereof. In some variations, an organism described herein is transformed with a CheA gene whose DNA sequence is at least 80-100% identical to the DNA sequence shown in FIG. 13 or complement thereof. In some variations, an organism described herein is transformed with a CheA gene whose DNA sequence is at least 90-100% identical to the DNA sequence shown in FIG. 13 or complement thereof. In some variations, an organism described herein is transformed with a CheA gene whose DNA sequence is at least 60, at least 65, at least 70, at least 75, at least 80, at least 85, at least 90, at least 95, or 100% identical to the DNA sequence shown in FIG. 13 or complement thereof. In some variations, an organism described herein is transformed with a CheA gene whose DNA sequence is at least 80% identical to the DNA sequence shown in FIG. 13. In some variations, an organism described herein is transformed with a CheA gene whose DNA sequence is at least 85% identical to the DNA sequence shown in FIG. 13 or complement thereof. In some variations, an organism described herein is transformed with a CheA gene whose DNA sequence is at least 90% identical to the DNA sequence shown in FIG. 13 or complement thereof.

In some variations, an organism described herein is optimized to increase production of CheC. In some variations, an organism described herein is transformed with a CheC gene. In some variations an organism described herein is transformed with a CheC gene to overexpress CheC. In some variations, an organism described herein is optimized to increase production of CheC in the solventogenic phase. In some variations, an organism described herein is transformed with a CheC gene. In some variations an organism described herein is transformed with a CheC gene to overexpress CheC in the solventogenic phase. In some variations, an organism described herein is transformed with a CheC gene from a microbial organism to overexpress CheC. In some variations, an organism described herein is transformed with a CheC gene from a *Clostridium* sp. to overexpress CheC. In some variations, an organism described herein is transformed with a CheC gene from *Clostridium beijerinckii* to overexpress CheC. In some variations, an organism described herein is transformed with a nucleic acid which results in an increase in expression of the CheC gene whose DNA sequence is shown in FIG. 14. In some variations, an organism described herein is transformed with a CheC gene whose DNA sequence is shown in FIG. 14 to overexpress CheC.

In some variations, an organism described herein is transformed with a CheC gene whose DNA sequence is at least 60-100% identical to the DNA sequence shown in FIG. 14 or complement thereof. In some variations, an organism described herein is transformed with a CheC gene whose DNA sequence is at least 80-100% identical to the DNA sequence shown in FIG. 14 or complement thereof. In some variations, an organism described herein is transformed with a CheC gene whose DNA sequence is at least 90-100% identical to the DNA sequence shown in FIG. 14 or complement thereof. In some variations, an organism described herein is transformed with a CheC gene whose DNA sequence is at least 60, at least 65, at least 70, at least 75, at least 80, at least 85, at least 90, at least 95, or 100% identical to the DNA sequence shown in FIG. 14 or complement thereof. In some variations, an organism described herein is transformed with a CheC gene whose DNA sequence is at least 80% identical to the DNA sequence shown in FIG. 14 or complement thereof. In some variations, an organism described herein is transformed with a CheC gene whose DNA sequence is at least 85% identical to the DNA sequence shown in FIG. 14 or complement thereof. In some variations, an organism described herein is transformed with a CheC gene whose DNA sequence is at least 90% identical to the DNA sequence shown in FIG. 14 or complement thereof.

In some variations, an organism described herein is optimized to increase production of CheD. In some variations, an organism described herein is transformed with a CheD gene. In some variations an organism described herein is transformed with a CheD gene to overexpress CheD. In some variations, an organism described herein is optimized to increase production of CheD in the solventogenic phase. In some variations, an organism described herein is transformed with a CheD gene. In some variations an organism described herein is transformed with a CheD gene to overexpress CheD in the solventogenic phase.

In some variations, an organism described herein is optimized to increase production of CheW. In some variations, an organism described herein is transformed with a CheW gene. In some variations an organism described herein is transformed with a CheW gene to overexpress CheW. In some variations, an organism described herein is optimized to increase production of CheW in the solventogenic phase. In some variations, an organism described herein is transformed with a CheW gene. In some variations an organism described herein is transformed with a CheW gene to overexpress CheW in the solventogenic phase. In some variations, an organism described herein is transformed with a CheW gene from a microbial organism to overexpress CheW. In some variations, an organism described herein is transformed with a CheW gene from a *Clostridium* sp. to overexpress CheW. In some variations, an organism described herein is transformed with a CheW gene from *Clostridium beijerinckii* to overexpress CheW. In some variations, an organism described herein is transformed with a nucleic acid which results in an increase in expression of the CheW gene whose DNA sequence is shown in FIG. 15. In some variations, an organism described herein is transformed with a CheW gene whose DNA sequence is shown in FIG. 15 to overexpress CheW.

In some variations, an organism described herein is transformed with a CheW gene whose DNA sequence is at least 60-100% identical to the DNA sequence shown in FIG. 15 or complement thereof. In some variations, an organism described herein is transformed with a CheW gene whose DNA sequence is at least 80-100% identical to the DNA sequence shown in FIG. 15 or complement thereof. In some variations, an organism described herein is transformed with a CheW gene whose DNA sequence is at least 90-100% identical to the DNA sequence shown in FIG. 15 or complement thereof. In some variations, an organism described herein is transformed with a CheW gene whose DNA sequence is at least 60, at least 65, at least 70, at least 75, at least 80, at least 85, at least 90, at least 95, or 100% identical to the DNA sequence shown in FIG. 15 or complement thereof. In some variations, an organism described herein is transformed with a CheW gene whose DNA sequence is at least 80% identical to the DNA sequence shown in FIG. 15 or complement thereof. In some variations, an organism described herein is transformed with a CheW gene whose DNA sequence is at least 85% identical to the DNA sequence shown in FIG. 15 or complement thereof. In some variations, an organism described herein is transformed with a CheW gene whose DNA sequence is at least 90% identical to the DNA sequence shown in FIG. 15 or complement thereof.

To develop an organism that can tolerate various inhibitors and products in the solvent production process, analysis of the mechanism of tolerance may be investigated. In some variations DNA microarray analysis is used to study the global or selected expression profiles of an organism described herein when exposed to various inhibitors or products in order to identify the organism's genetic responses. In addition, microarray analysis may be used to examine specific enzymes (glycolytic and non-glycolytic) that may be inhibited by these degradation compounds. Enzymes of particular interest include alcohol dehydrogenase, phosphofructokinase, glucokinase, galactokinase, aldehyde dehydrogenase, pyruvate dehydrogenase complex, butyryl-CoA dehydrogenase, butyrate kinase, etc.

In some variations, an organism described herein is optimized for alcohol dehydrogenase tolerance to inhibitors and products in the solvent production process. In some variations, an organism described herein is optimized for butyryl-CoA dehydrogenase tolerance to inhibitors and products in the solvent production process. In some variations, an organism described herein is optimized for butyrate kinase tolerance to inhibitors and products in the solvent production process.

In some variations, an organism described herein is optimized for phosphofructokinase tolerance to inhibitors and products in the solvent production process. In some variations, an organism described herein is optimized for glucokinase tolerance to inhibitors and products in the solvent production process. In some variations, an organism described herein is optimized for galactokinase tolerance to inhibitors and products in the solvent production process. In some variations, an organism described herein is optimized for aldehyde dehydrogenase tolerance to inhibitors and products in the solvent production process. In some variations, an organism described herein is optimized for pyruvate dehydrogenase complex tolerance to inhibitors and products in the solvent production process.

Methods of Optimizing Organisms for Use in Industrial Applications

In some variations, an organism described herein is optimized so as to be more tolerant of industrial conditions. In some variations, an organism described herein is subjected to a selection process under the industrial condition of interest, and the most adapted cells are identified. In some variations, an organism described herein is subjected to mutagenesis, subsequently subjected to a selection process under the industrial condition of interest, and the most adapted cells are identified. In some variations an organism described herein is transformed with one or more genes or regulatory sequences giving increased tolerance or resistance to an industrial condition of interest, and the most adapted cells are identified.

In some variations, an organism described herein is optimized to increase tolerance or resistance to one or more aspects or by-products of pretreatment. In some variations, an organism described herein is optimized to increase tolerance or resistance to one or more of salt, acetate, furfural, hydroxymethylfurfural, acetic acid, ferulic acid, glucuronic acid, rhoumaric acid, and phenolic compounds.

In some variations, an organism described herein is optimized to increase tolerance or resistance to rhoumaric acid. In some variations, an organism described herein is optimized to increase tolerance or resistance to ferulic acid.

In some variations, an organism described herein is optimized to increase tolerance or resistance to salt.

In some variations, an organism described herein is optimized to increase tolerance or resistance to one or more intermediates or products generated in the solventogenic process.

In some variations, an organism described herein is optimized to increase tolerance or resistance to one or more specific solvent recovery methods, including but not limited to gas stripping and adsorption or selective membranes.

In some variations, an organism described herein is optimized to increase tolerance or resistance to one or more temperatures utilized in the solventogenic process.

In some variations, an organism described herein is optimized to increase tolerance or resistance to one or more salts encountered in the solventogenic process.

In some variations, an organism described herein is optimized to increase tolerance or resistance to one or more pH conditions utilized in the solventogenic process.

In some variations, an organism described herein is optimized to increase tolerance or resistance to one or more continuous processing conditions utilized in the solventogenic process.

In some variations, an organism described herein is optimized to increase tolerance or resistance to one or more solvents generated in the solventogenic process.

In some variations, an organism described herein is optimized to increase tolerance or resistance to one or more feedstock materials in the solventogenic process.

EXAMPLES

Clostridial fermentation cultures were grown for both *C. beijerinckii* NCIMB 8052 and the hyper-butanol-producing mutant BA101 ATCC No. PTA-1550. Samples were collected at various time points over the course of fermentation. Total RNA was isolated from each time point sample. Dye-labeled DNA was generated by reverse transcription from total RNA and used as a sample probe in microarray hybridization. An RNA pool was constructed by mixing samples obtained from different stages of cell growth. Dye-labeled DNA probe derived from this RNA pool was used as a reference probe in microarray hybridization.

The DNA microarray included ~500 predicted protein-coding genes based on the draft sequence of *C. beijerinckii* NCIMB 8052 provided by the Joint Genome Institute, available at at GenBank as accession number CP000721. The array represented 10 functional classes covering ~10% of the genome.

Example 1

Bacterial Strains and Fermentation Protocols

Bacterial Strains and Growth Conditions. *C. beijerinckii* NCIMB 8052 is the wild-type strain. BA101 is the hyper butanol-producing mutant strain. Stocks of the wild-type and BA101 spores were stored in sterile nanopure $H_2O$ at 4° C.

Fermentation Protocols. 1 ml *C. beijerinckii* spore suspensions were heat shocked at 80° C. for 10 min, and inoculated into 100 ml tryptone-glucose-yeast extract (TGY) media containing 3% tryptone, 2% glucose, 1% yeast extract and 0.1% L-cysteine-HCl. The TGY culture was grown at 35° C. for 12 hrs in an anaerobic chamber (Coy Laboratory Products) maintained under a gas mixture of 85% N2, 10% CO2 and 5% H2. The culture was diluted $10^6$-$10^7$ fold into 0.45% liquefied TGY-agar and the mixture was allowed to solidify in plates in the anaerobic chamber. Plates were incubated at 35° C. for 2-3 days. Individual colonies developed on the plates were inoculated into 30 ml cooked meat medium (CMM, Oxoid #CM0081) plus added 1% glucose. The CMM culture was grown at 35° C. for 9 hrs in the anaerobic chamber. Subsequently, 10 ml CMM culture was inoculated into fresh 100 ml TGY media and grown at 35° C. for 3 hrs in the anaerobic chamber. An aliquot of 20 ml TGY pre-culture was inoculated into 1.7 liter P2 media containing P2 solutions supplemented with 6% glucose and 0.1% yeast extract in a fermentation reactor (New Brunswick Scientific). The P2 culture was grown at 35° C. under nitrogen flow. Fermentation samples were taken at various time points for analysis.

Example 2

Fermentation Sample Analysis

Aliquots of 1 ml fermentation culture grown in P2 media were collected at various time points for both *C. beijerinckii* NCIMB 8052 and BA101.

Cell growth was monitored by measuring the absorbance at 600 nm with a spectrophotometer (Beckman Coulter). Results are depicted in FIG. 1A. The growth curve for the two strains was very similar under these conditions.

Changes in pH were monitored by sampling the liquid culture using a pH meter. Results are depicted in FIG. 1B. The pH of the liquid culture was similar under these conditions, though the *C. beijerinckii* NCIMB 8052 liquid culture had a higher pH at the later timepoints.

Culture supernatants were analyzed for solvent and acid contents using gas chromatography (Agilent Technologies). Results are shown in FIG. 2A, FIG. 2B, and FIG. 2C. Total solvents were similar in the two strains until about 20 hours, after which point the level of solvents was consistently higher in the BA101 strain.

Example 3

RNA Sampling and Isolation

Aliquots of 10 ml fermentation culture in P2 media were obtained at various time points for both *C. beijerinckii* NCIMB 8052 and BA101. Cells were pelleted by centrifuging at 4000 g for 10 min. Total RNA was extracted from the cell pellets using a RNeasy mini kit (Qiagen) according to the manufacturer's protocol. RNA quality was determined with nanochip on an Agilent 2100 Bioanalyzer (Agilent Technologies). RNA concentration was quantified by measuring A260 using a UV/vis spectrophotometer (Biotek Instruments). Purified samples were stored in aliquots at −80° C.

To make a reference for comparing gene expression in the time course samples, a RNA pool was prepared and used to generate an oppositely labeled probe in microarray hybridization. To do so, a group of 500 ml static flask cultures were grown in P2 media for *C. beijerinckii* NCIMB 8052. The cultures were harvested at different stages of cell growth over the course of fermentation and total RNA was extracted from each cell pellet. An RNA pool was generated by mixing equal quantities of purified RNA from each growth phase, and this mixture was used to create a reference probe for microarray hybridization.

Example 4

Microarray Construction

DNA microarray was constructed by spotting long oligonucleotide probes onto a glass slide (UIUC Functional Genomics Keck Center). A 70-mer probe was selected for a single predicted open reading frame (ORF) in the sequenced *C. beijerinckii* genome (Illumina). Each probe was printed in duplicate on the array slide, Each array includes 485 predicted ORFs representing 10 functional classes and approximately 1/10th of the genome based on the draft sequence assembly of *C. beijerinckii* NCIMB 8052 (Joint Genome Institute). The *C. beijerinckii* NCIMB 8052 genes included in the microarray analysis are shown in Table 1, below.

Each gene is associated with a unique gene ID according to the JGI annotation available at the time when the list was compiled for microarray construction.

TABLE 1

| Gene name | Gene ID |
|---|---|
| Transcriptional regulator AbrB | 1 |
| Probable glucose kinase | 11 |
| Spo0A protein (CheY-like receiver domain and HTH-type DNA binding domain) | 54 |
| SpoIVB | 55 |
| Exonuclease VII small subunit | 62 |
| Exonuclease VII large subunit | 63 |
| Critical stage III sporulation protein AH | 67 |

TABLE 1-continued

| Gene name | Gene ID |
|---|---|
| Stage III sporulation protein AG, SpoIIIAG | 68 |
| Stage III sporulation protein AF, SpoIIIAF, putative | 69 |
| Stage III sporulation protein AE, SpoIIIAE | 70 |
| Stage III sporulation protein AD, SpoIIIAD | 71 |
| Stage III sporulation protein AC, SpoIIIAC | 72 |
| Stage III sporulation protein AB, SpoIIIAB | 73 |
| Stage III sporulation protein AA, SpoIIIAA | 74 |
| CDP-diglyceride synthetase | 90 |
| Pseudouridine synthase | 102 |
| Riboflavin kinase/FAD synthase | 103 |
| Ribosomal Protein S15 | 104 |
| Periplasmic serine protease, YMFB *B. subtilis* ortholog | 109 |
| Sporulation protein SpoIIIE, DNA segregation ATPase | 110 |
| Predicted Fe—S oxidoreductase | 111 |
| Catabolic acetolactate synthase | 139 |
| Aspartyl/asparaginyl-tRNA synthetase | 168 |
| Ribose 5-phosphate isomerase A | 175 |
| Putative alternative nitrogenase molybdenum-iron protein, NifD- or NifE-like | 193 |
| Putative alternative FeMo-cofactor synthesis protein, NifB-like | 196 |
| Putative alternative nitrogenase iron protein, NifH-like | 201 |
| Putative alternative nitrogenase molybdenum-iron protein, NifD- or NifE-like | 204 |
| Stage V sporulation protein | 217 |
| Asparagine synthase, N-terminal domain | 218 |
| ABC-type multi-drug/protein/lipid transport system, membrane ATPase component | 225 |
| $NH_3$-dependent NAD synthase fused to amidohydrolase domain | 228 |
| DSBH domain-containing protein | 229 |
| RecG helicase | 235 |
| Phosphopantetheine adenylyltransferase | 237 |
| Phosphotransacetylase | 241 |
| Acetate kinase | 242 |
| Acyl carrier protein ACP | 246 |
| ADP-glucose pyrophosphorylase | 253 |
| ADP-glucose pyrophosphorylase | 254 |
| Glycogen phosphorylase | 256 |
| Glycogen synthase, GlgA | 257 |
| L-lactate dehydrogenase | 290 |
| Acyl-coA dehydrogenase: butyryl-CoA dehydrogenase | 292 |
| Formate acetyltransferase | 293 |
| Pyruvate-formate lyase | 295 |
| 6-Phosphofructokinase | 306 |
| RecA recomdinase, ATPase | 310 |
| Stage V sporulation protein S, SpoVS | 312 |
| Beta-galactosidase | 324 |
| Beta-galactosidase | 328 |
| DNA-dependent RNA polymerase sigma subunit | 345 |
| Specialized DNA-dependent RNA polymerase sigma subunit | 346 |
| Response regulator (CheY-like receiver domain and HTH-type DNA-binding domain) | 350 |
| Permease component of ATP-dependent phosphate uptake system | 354 |
| Fe—S oxidoreductase, related to NifB/MoaA family with PDZ N-terminal domain | 358 |
| Glycerol 3-phosphate dehydrogenase | 360 |
| Coat morphogenesis sporulation protein SpoIVA | 361 |
| Uncharacterized stress-induced protein, TicC family | 364 |
| RNA polymerase-associated protein RpoZ, omega subunit, TLOH *B. subtilis* ortholog | 367 |
| Flavoprotein involved in penthothenate metabolism, YLOI *B. subtilis* ortholog | 368 |
| Primosomal protein N', superfamily II helicase | 369 |
| Ribulose-phosphate 3-epimerase | 378 |
| Ribosomal protein L28 | 380 |
| Ribosomal protein L2 | 410 |
| Adenylate kinase | 428 |
| DNA-dependent RNA polymerase alpha subunit | 436 |
| ABC-type transporter, ATPase component, cobalt transporters subfamily | 439 |
| Probable spore cortex lytic enzyme | 455 |
| Phosphotransbutyrylase, Ptb | 459 |
| Butyrate kinase, Buk | 460 |
| Flagellar motor switch protein, FliG | 471 |
| Ethanolamine utilization protein, EutE | 499 |
| Ribose 5-phosphate isomerase A | 537 |
| Alpha-L-arabinofuranosidase | 544 |
| Putative pyruvate kinase | 555 |
| Critical small acid-soluble spore protein, alpha/beta type | 559 |
| ATPases with chaperone activity ClpC, two ATP-binding domains | 587 |
| RNA methyltransferase Trmlt family, group 3 | 597 |
| Acyl-coA dehydrogenase: butyryl-CoA dehydrogenase | 617 |
| Critical probable spore coat protein | 650 |
| Putative spore coat protein | 651 |
| Spore coat protein S | 652 |

TABLE 1-continued

| Gene name | Gene ID |
|---|---|
| Mannosyl transferase | 653 |
| Probable spore coat protein | 654 |
| Stage II sporulation protein | 662 |
| DNA gyrase (topoisomerase II) subunit A | 671 |
| DNA gyrase (topoisomerase II) subunit B | 672 |
| RecF, ABC family ATPase | 674 |
| DNA polymerase III beta subunit | 676 |
| DNA replication initiator protein, ATPase | 677 |
| Stage III sporulation protein J, SpoIII J | 681 |
| SpoIII J-associated protein | 682 |
| Stage O sporulation protein J, SpoOJ | 686 |
| Spo0A activation inhibitor | 687 |
| Stage O sporulation protein J, SpoOJ | 688 |
| Single strand DNA-binding protein Ssb | 697 |
| Uncharacterized conserved protein, CotF *B. subtilis* ortholog | 718 |
| VWA domain-containing CoxE-like protein family | 731 |
| Membrane permease, predicted cation efflux pumps | 741 |
| Predicted Co/Zn/Cd cation transporter | 759 |
| Regulatory protein TenI | 775 |
| Uncharacterized protein containing two CBS domains | 779 |
| Transcriptional regulator, LysR family | 793 |
| Phosphoglycerate mutase family protein | 826 |
| 3-Oxoacyl-(acyl carrier protein) reductase | 834 |
| Alcohol dehydrogenase | 873 |
| Possible phosphoglycerate mutase | 875 |
| Uncharacterized oxidoreductase, Fe-dependent alcohol dehydrogenase family | 902 |
| Fructose-bisphosphate aldolase | 930 |
| Probable tagatose-6-phosphate kinase, AgaZ | 972 |
| Probable tagatose-6-phosphate kinase | 973 |
| Small acid-soluble spore protein beta | 1029 |
| Small acid-soluble spore protein | 1030 |
| Fructose-1,6-bisphosphatase, YYDE *B. subtils* ortholog | 1033 |
| Cytosine deaminase | 1074 |
| Cyclepropane fatty acid synthase | 1079 |
| ABC-type probable sulfate transporter, periplasmic binding protein | 1097 |
| Bifunctional enzyme phosphoribosyl-formyl-glycinamidine (FGAM) synthase | 1223 |
| 3-Oxoacyl-[acyl-carrier-protein] synthase III | 1238 |
| Dioxygenase | 1239 |
| Malonyl CoA-acyl carrier protein transacylase | 1240 |
| 3-Oxoacyl-[acyl-carrier-protein] reductase | 1241 |
| 3-Oxoacyl-[acyl-carrier-protein] synthase II | 1242 |
| Acetyl-CoA carboxylase | 1243 |
| FabZ | 1244 |
| Acetyl-CoA carboxylase: biotin carboxylase | 1245 |
| Acetyl-CoA carboxylase subunit beta | 1246 |
| Acetyl-CoA carboxylase carboxyl transferase subunit alpha | 1247 |
| Predicted endonuclease involved in recombination | 1274 |
| Ferric uptake regulation protein | 1276 |
| DNA-dependent RNA polymerase sigma subunit | 1283 |
| Cell division GTPase FtsZ | 1286 |
| Recombination protein RecR | 1313 |
| DNA-directed DNA polymerase III chain, DnaX | 1315 |
| Pyruvate carboxylase | 1324 |
| Xylan 1,4-beta-xylosidase | 1336 |
| Sigma factor SigK processing regulatory protein, BofA *B. subtilis* ortholog | 1359 |
| Phosphoenolpyruvate synthase | 1376 |
| Pyruvate water dikinase | 1379 |
| Spore coat protein CotJC | 1382 |
| Histidine kinase | 1385 |
| Long-chain fatty acid-CoA ligase | 1407 |
| 4-Hydroxybutyryl-CoA dehydratase | 1411 |
| Arsenate reductase, ArsC, tyrosine-phosphatase family enzyme | 1422 |
| Spore coat peptide assembly protein CotJB | 1434 |
| Transketolase | 1450 |
| Bifunctional D-arabino 3-hexulose-6-phosphate formaldehyde lyase/phosphohexuloisomerase | 1453 |
| Beta-glucosidase | 1475 |
| ABC transporter, ATP-binding component | 1477 |
| Xylose isomerase | 1504 |
| xylulose kinase | 1505 |
| Transaldolase, putative | 1507 |
| 3-Oxoacyl-[acyl-carrier-protein] reductase | 1519 |
| Activator of 2-hydroxyglutaryl-CoA dehydratase | 1526 |
| NADH-dependent butanol dehydrogenase BDH II | 1542 |
| MDR-type permease | 1577 |
| Response regulator (CheY-like receiver domain and DNA-binding HTH domain) | 1599 |
| Regulator of stationary/sporulation gene expression AbrB-like gene | 1615 |
| Phosphoglycerate mutase | 1662 |

TABLE 1-continued

| Gene name | Gene ID |
|---|---|
| Critical small acid-soluble spore protein, alpha/beta type | 1685 |
| Small acid-soluble spore protein SspA | 1699 |
| SleC | 1704 |
| Stage V sporulation protein T, transcriptional regulator AbrB homolog | 1745 |
| Ribose 5-phosphate isomerase B | 1773 |
| Thiolase, acetyl-CoA acetyltransferase | 1777 |
| Stage III sporulation protein D, spore protease Gpr-related protein | 1788 |
| Hypothetical protein | 1790 |
| Spore protease Gpr-related protein, YYAC *B. subtilis* ortholog | 1792 |
| Predicted iron-binding protein, hemerythrin | 1829 |
| Critical small acid-soluble spore protein | 1840 |
| Pyruvate kinase | 1851 |
| Alcohol dehydrogenase, zinc-dependent | 1873 |
| Transketolase, N-terminal section | 1874 |
| Transketolase, C-terminal section | 1875 |
| Ribulose-phosphate 3-epimerase | 1876 |
| Ribose 5-phosphate isomerase B | 1877 |
| ABC-type transport system, ATPase component | 1887 |
| Long-chain fatty acid-CoA ligase | 1903 |
| Malonyl CoA-acyl carrier protein transacylase | 1906 |
| Small acid-soluble spore protein beta | 1927 |
| Histidinol-phosphate aminotransferase | 1941 |
| 1-Phosphofructokinase | 1972 |
| Pyruvate ferredoxin oxidoreductase | 1982 |
| Predicted oxidoreductase, GSP39 *B. subtilis* ortholog | 1988 |
| Uncharacterized protein, TPUB *B. subtilis* ortholog | 2004 |
| Putative 4-cys ferredoxin | 2009 |
| SpoU | 2018 |
| Predicted S-adenosylmethionine-dependent methyltransferase | 2022 |
| Stage V sporulation protein D, SpoVD, FtsI/pbp family | 2024 |
| Stage V sporulation protein D, SpoVD, FtsI/pbp family | 2025 |
| Stage V sporulation protein E, SpoVE | 2029 |
| Chemotaxis motility protein B, MotB | 2038 |
| Chemotaxis motility protein A, MotA | 2039 |
| Butyryl-CoA dehydrogenase | 2135 |
| Homocitrate synthase subunit alpha, NifV | 2156 |
| Putative NirJ1 protein | 2161 |
| Putative [2Fe—2S] ferredoxin, FdxA | 2162 |
| FeMo-cofactor synthesis protein, NifN | 2163 |
| FeMo cofactor synthesis protein, NifE | 2164 |
| Nitrogenase molybdenum-iron protein beta subunit, NifK | 2165 |
| Nitrogenase molybdenum-iron protein alpha subunit, NifD | 2166 |
| GlnB-like protein-1 | 2168 |
| Nitrogenase iron protein, NifH | 2169 |
| Sporulation factor SpoIIM | 2206 |
| 3-Oxoacyl-(acyl carrier protein) reductase | 2207 |
| Aldehyde dehydrogenase; alcohol dehydrogenase | 2247 |
| FAD/FMN-containing dehydrogenase | 2254 |
| Pyruvate formate-lyase | 2257 |
| Pyruvate formate-lyase activating enzyme | 2258 |
| 8-Oxoguanine-DNA glycosylases | 2268 |
| Co-chaperonin GroES, Hsp10 family | 2270 |
| Chaperonin GroEL, Hsp60 family | 2271 |
| Glucose-6-phosphate isomerase | 2283 |
| 3-Oxoacyl-[acyl-carrier protein] reductase | 2303 |
| Streptogramin B lactonase | 2386 |
| Hypothetical cytosolic protein | 2399 |
| Acetyl-CoA acetyltransferase, thiolase | 2402 |
| MDR-type permease, probably tetracycline-resistance protein | 2412 |
| Malic enzyme | 2425 |
| Predicted aldo/keto reductase, YTBE/YVGN *B. subtilis* ortholog | 2496 |
| Phosphoenolpyruvate synthase | 2500 |
| Glucose kinase | 2501 |
| Membrane-associated methyl-accepting chemotaxis protein with HAMP domain | 2547 |
| Chemotaxis protein CheW | 2548 |
| Chemotaxis protein methyltransferase, CheR | 2553 |
| Chemotaxis protein CheA | 2555 |
| Flagellar motor protein MotB | 2556 |
| Flagellar motor component MotA | 2557 |
| Beta-glucosidase | 2559 |
| Pyruvate kinase | 2577 |
| Enolase | 2578 |
| 2,3-Biphosphoglycerate-independent phosphoglycerate mutase gene | 2579 |
| Transketolase, C-terminal section | 2596 |
| Transketolase, N-terminal section | 2597 |
| tRNA-processing ribonuclease | 2605 |
| Protein containing Zn-finger domain | 2624 |
| SOS regulatory protein LexA | 2626 |

TABLE 1-continued

| Gene name | Gene ID |
|---|---|
| DNA mismatch repair enzyme, MutL | 2630 |
| Mismatch repair protein MutS, ATPase | 2634 |
| Ketopantoate hydroxymethyltransferase | 2674 |
| Alpha-galactosidases/6-phospho-beta-glucosidase, family 4 glycosyl hydrolase | 2726 |
| Stage II sporulation protein | 2738 |
| Stage V sporulation protein B | 2745 |
| Stage V sporulation protein T, SpoVT | 2746 |
| Stage V sporulation protein | 2754 |
| HD-GYP hydrolase domain-containing protein | 2760 |
| Spore maturation protein | 2782 |
| Pyruvate carboxylase PYKA | 2785 |
| Pyruvate formate lyase-activating enzyme | 2795 |
| HD-GYP hydrolase domain-containing protein | 2801 |
| Short-chain dehydrogenase: 3-oxoacyl-[acyl-carrier protein] reductase | 2805 |
| Transcriptional regulator TetR/AcrR family | 2813 |
| Phosphatidylserine decarboxylase | 2814 |
| Mannose/fructose-specific phosphotransferase system component IIC | 2839 |
| Mannose-specific phosphotransferase system component IIAB | 2840 |
| Pyruvate formate-lyase | 2846 |
| Pyruvate formate-lyase activating enzyme | 2850 |
| Acyl-acyl carrier protein thioesterase | 2861 |
| Putative acyl-CoA ligase | 2868 |
| Aldehyde dehydrogenase, NAD-dependent dehydrogenase family | 2878 |
| Zinc-containing alcohol dehydrogenase, long-chain | 2891 |
| Putative transcription activator, Stc-like | 2892 |
| Cation transport P-type ATPase | 2906 |
| Septum site-determining protein, MinD | 2941 |
| Stage V sporulation protein E | 2943 |
| Putative stage IV sporulation protein FB | 2945 |
| Biotin carboxylase: acetyl-CoA carboxylase, putative | 2948 |
| Protein of unknown function LDUF464 superfamily | 2955 |
| Putative kinase | 2970 |
| Ribulose-phosphate 3-epimerase | 2973 |
| Alcohol dehydrogenase, zinc-dependent | 2988 |
| Transketolase, N-terminal section | 2989 |
| Transketolase, C-terminal section | 2990 |
| Ribulose-phosphate 3-epimerase | 2991 |
| Ribose 5-phosphate isomerase B | 2992 |
| Ribulose-phosphate 3-epimerase family protein | 2995 |
| Similar to ribulose 5-phosphate 3-epimerase | 2996 |
| Stage V sporulation protein R, SpoVR | 3012 |
| 6-Phosphofructokinase | 3028 |
| VanW-like protein family | 3037 |
| Glyceraldehyde 3-phosphate dehydrogenase | 3041 |
| Phosphoglycerate kinase | 3042 |
| Triosephosphate isomerase | 3043 |
| 2,3-Bisphosphoglycerate-independent phosphoglycerate mutase | 3044 |
| phosphopyruvate hydratase | 3046 |
| ABC-type sulfate transporter, ATPase component | 3054 |
| Putative alternative nitrogenase molybdenum-iron protein, NifD- or NifE-like | 3056 |
| ABC-type probable sulfate transporter, permease protein | 3059 |
| Pyruvate formate lyase-activating enzyme | 3069 |
| Pyruvate formate lyase-activating enzyme | 3070 |
| Ferredoxin | 3075 |
| Critical peptidase S16, ATP-dependent protease | 3077 |
| HD-GYP hydrolase domain-containing protein | 3100 |
| Muconate cycloisomerase-related protein, YKGB *B. subtilis* ortholog | 3102 |
| Glutamyl-tRNA reductase | 3107 |
| Hydroxymethylbilane syntase (porphobilinogen deaminase) | 3109 |
| Uroporphyrinogen III syntase | 3110 |
| Delta-aminoleevulinic acid dehydratase (porphobilinogen synthase) | 3111 |
| Glutamate-1-semialdehyde aminotransferase | 3112 |
| Possible cysteine desulphurase from NifS family | 3135 |
| FKBP-type peptidyl-prolyl cis-transisomerase (trigger factor) | 3149 |
| Critical ClpX, ATPase regulatory subunit | 3151 |
| ATP-dependent Lon protease | 3153 |
| Spore cortex protein | 3209 |
| Sporulation protein B | 3210 |
| Membrane-associated sensory transduction histidine kinase (with HAMP domain) | 3255 |
| Response regulator (CheY-like receiver domain and HTH DNA-binding domain) | 3256 |
| Hydrogenase expression/formation protein HypE | 3277 |
| Fructose-biphosphate aldolase class I | 3310 |
| Beta-xylosidase | 3318 |
| Small acid-soluble spore protein SspA | 3349 |
| Small acid-soluble spore protein, alpha/beta type | 3380 |
| Stage O sporulation protein J, putative | 3416 |
| Putative transcription activator Stc | 3418 |
| Alcohol dehydrogenase | 3419 |

TABLE 1-continued

| Gene name | Gene ID |
|---|---|
| Putative electron-transfer protein HydG | 3420 |
| Alcohol dehydrogenase, iron-containing | 3432 |
| Critical small acid-soluble spore protein, alpha/beta type | 3461 |
| Probable enoyl-CoA hydratase | 3466 |
| Probable enoyl-CoA hydratase | 3467 |
| Alcohol dehydrogenase, zinc-containing | 3477 |
| Possible stage V sporulation protein, SpoVT | 3499 |
| Acyl-CoA dehydrogenase, short-chain specific: butyryl-CoA dehydrogenase | 3508 |
| Transaldolase | 3637 |
| Acetyl-CoA carboxylase (biotin carboxylase subunit) | 3649 |
| Acetyl-CoA carboxylase biotin carboxyl carrier protein | 3650 |
| L-lactate dehydrogenase | 3682 |
| Phosphoglycerate mutase | 3691 |
| Uncharacterized conserved protein YHAD family | 3755 |
| L-lactate dehydrogenase | 3774 |
| L-serine dehydratase, iron-sulfur-dependent, beta subunit | 3775 |
| Beta-glucosidase | 3801 |
| Transcriptional regulator of NagC/XylR (ROK) family, sugar kinase | 3813 |
| Fructose bisphosphatase | 3818 |
| Propionate-CoA transferase | 3820 |
| Crotonase | 3821 |
| Fructose-1,6-bisphosphate aldolase | 3828 |
| Phosphoglucomutase | 3831 |
| Accessory regulator protein B | 3855 |
| Histidine kinase-like ATPase | 3856 |
| Accessory regulator protein A | 3857 |
| Flagellar biosynthesis related protein | 3885 |
| Spore coat protein, putative | 3889 |
| Critical spore coat protein, CotF-related | 3890 |
| Spore coat protein, putative | 3891 |
| Critical spore coat protein, CotF-related | 3892 |
| (R)-2-hydroxyglutaryl-CoA dehydratase activator-related protein | 3926 |
| Glucose kinase | 3978 |
| 3-Hydroxybutyryl-CoA dehydrogenase | 3988 |
| ABC transporter, ATP-binding protein | 3993 |
| Ald CoA-acylating aldehyde dehydrogenase | 3999 |
| Butyrate-acetoacetate CoA-transferase subunit A | 4000 |
| Butyrate-acetoacetate CoA-transferase subunit B | 4001 |
| Acetoacetate decarboxylase | 4002 |
| ABC type transport system, ATPase component | 4022 |
| Phosphoenolpyruvate synthase/pyruvate phosphate dikinase | 4025 |
| Pyruvate water dikinase | 4028 |
| Zinc-binding dehydrogenase: alcohol dehydrogenase | 4030 |
| Histidine kinase-like ATPase | 4032 |
| Response regulator (CheY-like receiver domain and HTH DNA-binding domain) | 4033 |
| Short-chain dehydrogenase: 3-oxoacyl-[acyl-carrier protein] reductase | 4069 |
| Nitroreductase family protein | 4070 |
| Phosphoglycerate mutase | 4085 |
| Chemotaxis protein CheW | 4116 |
| Alpha-glucosidase | 4142 |
| Thioredoxin reductase | 4148 |
| Malic enzyme | 4150 |
| Anaerobic sulfite reductase subunit B | 4154 |
| Anti-anti SigF | 4182 |
| Anti-simga factor F, Stage II sporulation protein AB | 4183 |
| Sporulation-specific sigma factor F | 4184 |
| Critical SpoVA protein | 4185 |
| IMP dehydrogenase/GMP reductase: Stage V sporulation protein AD | 4186 |
| Stage V sporulation protein AE, SpoVAE | 4187 |
| Spore protease Gpr | 4192 |
| Stage II sporulation protein P, SpoIIP | 4193 |
| Transcriptional regulator of heat shock genes, HrcA | 4198 |
| Molecular chaperone DnaK, Hsp70 family | 4200 |
| Molecular chaperones DnaJ, Hsp40 family | 4201 |
| Ferredoxin-nitrite reductase | 4202 |
| Stage IV sporulation protein | 4211 |
| Spore coat protein S | 4220 |
| Predicted dehydrogenase of short-chain alcohol dehydrogenase family | 4238 |
| TPR repeats-containing protein | 4350 |
| Alpha-galactosidase | 4383 |
| Alpha-galactosidase | 4384 |
| Thiamine biosynthesis enzyme ThiH | 4386 |
| Spore photoproduct lyase SplB | 4463 |
| Melibiase (alpha-galactosidase) | 4465 |
| Cysteine synthase/cystathionine-beta snythase, CysK | 4468 |
| DNA gyrase subunit B | 4500 |
| DNA gyrase subunit A | 4501 |
| SsDNA exonuclease RecJ | 4503 |

TABLE 1-continued

| Gene name | Gene ID |
|---|---|
| Pyruvate: ferredoxin oxidoreductase | 4506 |
| Chemotaxis protein CheW | 4513 |
| Chemotaxis protein CheD | 4514 |
| Chemotaxis protein CheB, containing CheY-like receiver domain and HTH DNA-binding domain | 4515 |
| Chemotaxis protein methyltransferase CheR | 4516 |
| Chemotaxis histidine kinase CheA, containing CheW-like adaptor domain | 4517 |
| Chemotaxis protein CheC | 4518 |
| Chemotaxis signal transduction protein CheW | 4520 |
| Flagellar switch protein FliM | 4521 |
| Flagellar switch protein FliY, containing CheC-like domain | 4522 |
| Flagellar hook-associated protein FlgK | 4526 |
| Flagellar hook-associated protein 3 | 4527 |
| Carbon storage regulator | 4529 |
| Flagellar protein FliS | 4532 |
| Flagellar cap protein FliD, putative | 4533 |
| Possible hook-associated protein, flagellin family | 4535 |
| Spore coat polysaccharide biosynthesis protein | 4543 |
| FlaG | 4544 |
| Chemotaxis mortality protein A, MotA | 4551 |
| Chemotaxis mortality protein A, MotB | 4552 |
| Flagellar basal body rod protein FlgB | 4553 |
| Flagellar basal body rod protein FlgC | 4554 |
| Flagellar assembly protein FliH, putative | 4558 |
| Flagellar-type ATPase | 4559 |
| Flagellar export protein FliJ | 4560 |
| Flagellar hook assembly protein FlgD, putative | 4562 |
| Flagellar hook protein flgE | 4564 |
| Flagellar protein FlbD | 4565 |
| Flagellar basal body-associated protein FliL | 4566 |
| Flagellar biosynthesis protein FliP | 4568 |
| Flagellar biosynthesis protein FliQ | 4569 |
| Flagellar biosynthesis protein FlhA | 4571 |
| Flagellar GTP-binding protein FlhF | 4572 |
| Sigma factor of SigD/WhiG family | 4575 |
| Flagellar basal body rod protein | 4578 |
| General secretion pathway protein, pilin family | 4608 |
| Ferredoxin | 4635 |
| Sulfate adenylate transferase, CysD subfamily | 4636 |
| GTPase, sulfate adenylate transferase subunit | 4637 |
| HD-GYP domain-containing protein | 4638 |
| Chemotaxis protein CheW | 4639 |
| Chemotaxis protein methyltransferase CheR | 4642 |
| Chemotaxis protein/glutamate methylesterase | 4643 |
| CheY-like receiver domains, putative | 4649 |
| ABC transporter, ATP-binding protein | 4656 |
| Hsp 90 | 4663 |
| Uncharacterized conserved protein | 4670 |
| ATP-dependent Clp proteinase | 4671 |
| Deoxyribose-phosphate aldolase | 4679 |
| HD-GYP hydrolase domain-containing protein | 4683 |
| Beta-xylosidase, family 43 glycosyl hydrolase | 4696 |
| Hsp 18 | 4699 |
| Glycerol dehydrogenase | 4730 |
| L-lactate dehydrogenase | 4749 |
| Pyruvate formate-lyase | 4760 |
| Glycerol dehydratase activator | 4761 |
| Critical IMP dehydrogenase/GMP reductase | 4775 |
| Alcohol dehydrogenase/acetaldehyde dehydrogenase | 4776 |
| 2-Oxoacid: ferredoxin oxidoreductase, alpha subunit | 4779 |
| 3-oxoacyl-[acyl-carrier-protein] synthase III | 4789 |
| Activator of 2-hydroxyglutaryl-CoA dehydratase | 4794 |
| Predicted permease | 4797 |
| Chemotaxis protein CheY homolog | 4801 |
| Chemotaxis protein cheA | 4802 |
| Chemotaxis protein Chew | 4803 |
| Transcriptional regulator, Lrp family | 4811 |
| Critical endopeptidase Clp | 4819 |
| 3-Oxoacyl-[acyl-carrier-protein] synthase | 4831 |
| Lactate dehydrogenase | 4866 |
| Small acid-soluble spore protein SspC2 | 4927 |
| L-lactate dehydrogenase | 4951 |
| Phosphoglycerate mutase | 4961 |
| Alpha-xylosidase | 4968 |
| Aldehyde dehydrogenase (NAD+) | 4974 |
| Critical bacterial regulatory protein MarR | 4976 |
| Topoisomerase I | 4983 |
| Acetyl-CoA: acetoacetyl-CoA transferase alpha subunit | 4992 |

TABLE 1-continued

| Gene name | Gene ID |
|---|---|
| Pyruvate kinase, barrel domain | 5003 |
| Critical heat shock protein DnaJ, N-terminal domain | 5005 |
| Butyryl-CoA dehydrogenase, putative | 5011 |
| Oligopeptide transport permease protein | 5044 |

Microarray DNA Probe Labeling and Hybridization. Two-color microarray hybridization was performed using the aminoallyl labeling procedure adapted from a TIGR protocol (UIUC Functional Genomics Keck Center). Briefly, 3 μg of purified total RNA were primed with random hexamers (Pharmacia) and used as templates for DNA synthesis using aminoallyl dNTPs (Ambion) and Superscript III reverse transcriptase (Invitrogen) in each labeling reaction. The aminoallyl-labeled DNAs were coupled to Cy3 or Cy5 dye esters (Molecular Probes), and oppositely dye-labeled probes were hybridized on an array simultaneously. To compare gene expression in the time course of fermentation, one of the dye-labeled probes was generated from samples collected at individual time points, whereas the other dye-labeled control probe was derived from the RNA pool as described above.

Microarray hybridization was performed using one array for each sample collected in the fermentation time course. Briefly, the slides were rehydrated, UV cross-linked, and pre-hybridized in 5×SSC, 0.1% (w/v) SDS and 1% (w/v) BSA at 42° C. for 45 min. The slides were then hybridized with a mixture of oppositely labeled DNA probes in hybridization buffer (Ambion) at 42° C. for 16-48 hrs. After hybridization, the slides were washed with 1×SSC and 0.2% (w/v) SDS at 42° C. for 5 min, followed by a second wash in 0.1×SSC and 0.2% (w/v) SDS at room temperature for 5 min, and a last wash in 0.1×SSC for 5 min. The slides were dried and immediately scanned on an Axon 4000B scanner (UIUC Functional Genomics Keck Center). Features in each array were extracted using GenePix Pro 6.0.

Results are depicted in FIG. 3A and FIG. 3B for *C. beijerinckii* NCIMB 8052 and BA101, respectively. Expression level is indicated by intensity of the color bar (green to red) based on $log_2$ transformation of the normalized expression ratio determined for each gene at individual time point. Temporal expression patterns are visualized with hierarchical clustering for the transition of fermentation cultures from acidogenesis to solventogenesis Microarray Data Analysis. Data generated from microarray experiments were processed and visualized using the TM4 suite (TIGR). Briefly, the expression ratio (Cy5/Cy3) for a gene in each sample was determined based on quantification of the fluorescence intensity for each spot on the array using GENEPIX® Pro 6.0 Microarroay Acquisition & Analysis Software. The expression ratios obtained from all the genes on each array were normalized using Midas (TIGR). LOWESS intensity-based normalization was applied in most cases. Normalized expression ratios for a gene obtained at the analyzed time points were used to construct the temporal profiles of gene expression over the course of fermentation for *C. beijerinckii* NCIMB 8052 and BA101, respectively. Global expression patterns were analyzed by average linkage hierarchical clustering with Euclidean distance matrices and visualized colorimetrically using TMEV (TIGR).

Results for mRNA accumulation levels of various enzymes in the Clostridial solventogenic pathway were quantitatively depicted in FIG. 4. Differential mRNA accumulation of solventogenic genes was compared in *C. beijerinckii* NCIMB 8052 (♦) versus BA101 (o). Increased expression in BA101 during the solventogenic stage was observed for alcohol dehydrogenase (Adh), butyryl-CoA dehydrogenase (Bcd) and butyrate kinase (Buk).

Results for mRNA accumulation levels of various sugar transporters were quantitatively depicted in FIG. 5. Differential mRNA accumulation of sugar transporters was compared in *C. beijerinckii* NCIMB 8052 (♦) and BA101 (o). Components of mannose-family phosphoenolpyruvate (PEP)-dependent phosphotransferase system IIA, IIB (ManIIAB) and IIC (ManIIC) were significantly down-regulated in BA101.

Results for mRNA accumulation levels of various sporulation genes were quantitatively depicted in FIG. 6. Differential expression of sporulation genes was compared in *C. beijerinckii* NCIMB 8052 (♦) and BA101 (o). Induction of late stage sporulation factors was much weaker in BA101 than in the wild-type strain. Lowered activation in BA101 through the solventogenic phase was observed for coat morphosis sporulation protein (SpoIVA), Stage V sporulation protein B (SpoVB) and small acid-soluble spore protein (SspA).

Results for mRNA accumulation levels of various chemotaxis genes were quantitatively depicted in FIG. 7. Differential expression of chemotaxis genes was compared in *C. beijerinckii* NCIMB 8052 (♦) and BA101 (o). Higher expression levels of CheA, CheC, CheD and CheW in a chemotaxis gene cluster were observed for BA101 during the solventogenic stage.

Results for mRNA accumulation levels of various solventogenic genes were quantitatively depicted in FIG. 8. Solventogenic genes with comparable expression kinetics were compared in *C. beijerinckii* NCIMB 8052 (♦) and BA101 (o). Expression of aceto-acetyl CoA:acetate-butyrate CoA transferase subunit α/β (CtfA/B) and acetoacetate decarboxylase (Adc) was highly activated at the onset of solventogenic phase in BA101 and the wild-type strain. Changes in expression levels were much smaller for thiolase (Thl), 3-hydroxybutyryl-CoA dehydrogenase (Hcd) and crotonase (Crt) in BA101 and the wild-type strain.

Tables 2A and 2B show subsets of genes that were found to be differentially expressed between *C. beijerinckii* NCIMB 8052 and BA101.

TABLE 2 (A)

Genes with increased expression in BA101 compared with the wild-type strain.

| Functional class | Gene Name | Gene product activity |
|---|---|---|
| Solventogenesis | Alcohol dehydrogenase | Catalyzing the reduction of aldehyde to alcohol |
| | Butyryl-CoA dehydrogenase | Catalyzing the reduction of crotonyl-CoA to butyryl-CoA |
| | Butyrate kinase | Catalyzing the generation of butyrate from butyrylphosphate with concurrent ATP synthesis |
| Chemotaxis | CheA | Chemotaxis sensory transducer, histidine kinase |
| | CheC | Chemotaxis protein |
| | CheD | Chemotaxis methylation system protein |
| | CheW | Chemotaxis protein, histidine kinase |

TABLE 2 (B)

Genes with reduced expression in BA101 relative to the wild-type strain.

| Functional class | Gene name | Gene product activity |
|---|---|---|
| Sporulation | Coat morphosis sporulation protein SpoIVA | Spore coat assembly |
| | Stage V sporulation protein B SpoVB | Spore cortex biosynthesis |
| | Small acid-soluble spore protein SspA | Packaging and protection of spore DNA |
| Sugar transporters | Mannose-specific phosphoenolpyruvate-dependent phosphotransferase system component IIAB | Mediating phosphoryl relay for the modification of incoming sugar |
| | Mannose/fructose-specific phosphoenolpyruvate-dependent phosphotransferase system component IIC | Mediating sugar transport across the membrane through permease |

Example 5

General Methods Used in the Examples

PCR primers are designed using the PrimerSelect features of the DNASTAR suite of molecular biology programs from DNAStar, Inc. (Madison, Wis.). Techniques of primer design are known in the art (PCR Primer Design, 2007, Anton Yuryev editor, Humana Press).

PCR products are amplified using Takara EX TAQ™ DNA Polymerase from Takara Bio USA (Madison, Wis.), and a GENE AMP® PCR system 9700 thermocycler from Applied Biosystems (Foster City, Calif.). Other DNA polymerase products for PCR provide suitable alternatives. Cycling parameters can vary according to the specific primers and DNA sequences being amplified. In general the methods and parameters are known in the art. (PCR Protocols, 2nd edition, 2003, John M. S. Bartlett and David Stirling editors, Humana Press; PCR: The Basics, 2nd edition, 2006, M. J. McPherson and S. G. Moller, Taylor & Francis publisher).

For colony PCR, fresh colonies are picked from Petri plates and suspended in a 50-100 μL of ultrapure water or 10 mM Tris, pH 7.5. 1-5 μL of the cell suspension is substituted for the purified DNA in a normal PCR reaction mixture. The initial PCR heat cycle of the process may be extended in some cases, for example 10 min at 94° C., to aid in cell lysis.

The isolation and purification of plasmid DNA, chromosomal DNA, DNA fragments from preparative agarose gels and PCR products is accomplished using commercial kits that are available from various suppliers. Examples of two such suppliers are Qiagen Inc. (Valencia, Calif.) and MO BIO Laboratories (Carlsbad, Calif.). Examples of Qiagen kits for some applications are "QIAPREP®" for plasmid DNA, "QIAQUICK®" for purifying DNA fragments from agarose gels, and "QIAQUICK®" or "MINELUTE®" for purifying PCR products. Chromosomal DNA preparations (genomic DNA) are prepared using the "UltraClean Soil DNA Isolation" kit from MO BIO Laboratories.

For introduction of DNA into *Clostridium* hosts by electroporation (transformation), a culture of the *Clostridium* strain is grown to an $OD_{600}$ of 0.8, then washed for two cycles with 15% polyethylene glycol (PEG). Electroporation is done in the presence of 10 μg of plasmid DNA using a cuvette with a 2 mm path in a Bio-Rad Gene Pulser™ exponential decay generator set (BioRad, Richmond, Calif.) for 2.0 kV (10 kV/cm), 200 ohms and 4.5 ms. Electroporation parameters may vary from strain to strain. Those skilled in the art will be capable of adjusting parameters as needed (Molecular Cloning: A laboratory manual, 3rd edition, 2001, Joseph Sambrook and David W. Russell, Cold Spring Harbor Laboratory Press; Handbook on Clostridia, 2005, Peter Durre editor, Taylor & Francis publisher).

General cloning methods such as use of restriction endonucleases, DNA ligase and other nucleic acid modification techniques, separative techniques such as agarose or polyacrylamide gel electrophoresis, and the like are known in the art and comprehensive guides are available (Methods for General and Molecular Microbiology, 3rd edition, 2007, C. A. Reddy editor in chief, ASM Press; Molecular Genetics of Bacteria, 2nd edition, 2003, Larry Snyder and Wendy Champness, ASM Press; Molecular Cloning: A laboratory manual, 3rd edition, 2001, Joseph Sambrook and David W. Russell, Cold Spring Harbor Laboratory Press).

Example 6

Construction of Strains of Solventogenic Clostridia Wherein spoIVA Gene Expression is Deficient A mutant derivative of *Clostridium beijerinckii* strain NCIMB 8052 is constructed wherein the function of the spoIVA gene encoded by SEQ ID NO: 9 (locus_tag Cbei_1136 of GenBank CP000721) is destroyed by insertion of a plasmid bearing a cloned fragment of the spoIVA gene DNA into the chromosome, so as to disrupt the coding sequence of the gene. Insertion of the plasmid into the chromosome takes place by single-cross-over homologous recombination between the chromosomal spoIVA gene and the cloned spoIVA fragment.

A spore suspension of *Clostridium beijerinckii* strain NCIMB 8052 is heat shocked for 10 minutes at 80° C., placed on ice briefly, moved into a Coy® anerobic chamber (Coy Laboratory Products, Grass Lake, Mich.) containing an atmosphere of 85% $N_2$, 10% $CO_2$ and 5% $H_2$, and then used to inoculate 10 mL of TGY medium in an 18 mm diameter test tube. The culture is grown at 35° C. to an $OD_{600}$ of about 0.6 to 0.8. A 1.0 mL portion of this culture is used to inoculate another 10 mL of TGY, which is grown to about 0.6 $OD_{600}$, or to a density that yields good chromosomal DNA preparations. The culture is then harvested and processed to prepare purified chromosomal DNA using the "UltraClean™ Soil DNA Isolation" kit and protocols from MO BIO Laboratories.

PCR primers incorporating terminal XmaI restriction endonuclease sites are designed using the PRIMERSELECT™ software package of DNASTAR Inc. (Madison, Wis.) so as to amplify an internal fragment of the spoIVA gene of preferably 250-600 bp in length, ideally in the central part of the coding region of the gene; for example, the 3' one-third of the gene preferably is avoided to prevent partially functioning spoIVA gene product in the resulting mutants.

The chosen internal fragment of the spoIVA gene is amplified by the PCR reaction using the purified chromosomal DNA preparation and the chosen PCR primers. The amplified spoIVA internal fragment with the terminal XmaI sites is purified from the finished PCR mixture using Qiagen MINELUTE® spin columns or a similar product. Alternatively the fragment could be separated using a preparative agarose gel and purified from a gel slice using Qiagen QIAQUICK® kits. The purified spoIVA fragment is restriction digested with XmaI to generate cohesive ends, and reisolated from an agarose gel.

Plasmid pAK102 (AY Kim and HP Blaschek, 1993, J Bacteriol. 175:3838-43) was constructed by ligation of HindIII-linearized plasmid pUC19 and a 2.3-kb HindIII erythromycin resistance gene fragment from plasmid pVA677 (F L Macrina et. al., 1980, J. Bacteriol. 143:1425-1435). pAK102 encodes resistance to ampicillin and erythromycin, and replicates autonomously in *E. coli* but not in *Clostridium* species; thus in *Clostridium*, pAK102 is a "suicide vector." Plasmids of equivalent function could be prepared from common *E. coli* vectors and common sources of the erythromycin resistance gene functional in *Clostridium* (Methods for General and Molecular Microbiology, 3rd edition, 2007, C. A. Reddy editor in chief, ASM Press; Clostridia, 1989, Nigel P. Minton and David J. Clarke editors, Plenum Press). Plasmid pAK102 DNA is purified from a transformed *E. coli* DH5alpha host that is routinely grown under 50 μg/mL of ampicillin selection, using a Qiagen QIAPREP® kit. The pAK102 DNA is linearized by digestion with XmaI and the purified internal fragment of the spoIVA gene is cloned into the vector using DNA ligase.

The ligation mixture is electroporated into *E. coli* DH5alpha and transformants are recovered by growth on LB agar petri plates as colonies that are resistant to 50-100 μg/mL of ampicillin. The transformants are screened to determine the size of the *Clostridium* fragment inserted into the plasmid. To do this, colony PCR is performed using the same primers that were used above, and PCR reaction products are separated by electrophoresis on 1% to 1.5% agarose gels. Transformants that show only the expected fragment size, and not multiples of that size, are selected for the next step and are labeled "pAK102/spoIVA".

Plasmid pAK102/spoIVA DNA is purified from the chosen *E. coli* transformant, using a Qiagen QIAPREP® kit. The plasmid DNA is used to transform strain *C. beijerinckii* NCIMB 8052 by electroporation. Transformants are initially allowed to recover by growth in TGY medium without antibiotic selection for 3 hours at 35° C., then spread on TGY-1.5% agar plate medium containing 25 μg/mL of erythromycin. Alternatively, erythromycin concentrations as low as 10 μg/mL might be considered for the initial selective plates. Following their initial recovery, erythromycin resistant strains are propagated in the presence of 10-40 μg/L of erythromycin. Because the pAK102 vector is incapable of independent replication in *Clostridium* species, transformants are expected to retain antibiotic resistance by virtue of having integrated the pAK102/spoIVA construct into the chromosome, at a site bounded by the endpoints of the cloned spoIVA fragment. The proper insertion of the plasmid, and its position within the spoIVA gene is verified by DNA sequencing of spoIVA gene target region.

The resulting strains, which are mutants of *C. beijerinckii* NCIMB 8052 having disrupted or impaired spoIVA function, are tested in fermentations for solvent formation in P2 medium as in Example 1, except that 10-25 μg/L of erythromycin is added to the fermentation medium for every 24 hours of elapsed culture time. The preservation and routine propagation of the spoIVA mutant strains in the lab, as well as other strains that may be defective in the formation of normal spores, may require the making and use of frozen cultures of vegetative cells in medium containing 15% glycerol, or 0.1% DMSO, or other cryoprotectives. Such methods are known to those who are skilled in the art (Methods for General and Molecular Microbiology, 3rd edition, 2007, C. A. Reddy (editor in chief), ASM Press) and could be used if necessary to prevent the emergence of degenerated strains by excessive serial propagation over time.

In the general manner of this example, derivatives of NCIMB 8052, or BA101 or other solventogenic *Clostridium* species and strains, are constructed having mutations in other genes that are targeted for various degrees of disrupted function; for instance mutants bearing defective spoVB, sspA, manIIAB or manIIC genes or their close homologs, or where expression of the normal gene is driven by reduced-strength promoters. In the case of *Clostridium* species having active restriction-modification systems, such as for example *C. acetobutylicum* ATCC 824 and other strains, steps to overcome the transformation barrier imposed by the restriction systems are added to the above protocol. Typically these involve prior methylation of the transforming DNA by various in vitro DNA methylation reactions, or by propagation of the DNA/vector in hosts that methylate the DNA but do not restrict it. Procedures for such modification are common in the research literature of solventogenic clostridia (Handbook on Clostridia, 2005, Peter Durre (editor), Taylor & Francis publisher).

Example 7

Construction of Solventogenic Clostridia Engineered for Constitutive Expression of the Adh Gene at High Levels from a Heterologous Promoter A derivative of *Clostridium beijerinckii* strain NCIMB 8052 or BA101 is constructed whereby the NCIMB 8052 adh gene (SEQ ID NO: 1, Cbei_2181 of GenBank CP000721) is constitutively expressed at increased levels by a combination of transcription from the promoter of the ferredoxin gene of *Clostridium pasteurianum* ATCC 6013, and by gene amplification on a replicative multicopy plasmid.

Plasmid pMTL500E is a multicopy *E. coli/Clostridium* shuttle vector that encodes erythromycin resistance and which is stably maintained in *Clostridium* strains including *C. beijerinckii* 8052 (AM López-Contreras, et. al., 2001, *Clostridium beijerinckii* cells expressing *Neocallimastix patriciarum* glycoside hydrolases show enhanced lichenan utilization and solvent production, Appl Environ Microbiol. 67:5127-33; A Y Kim, et. al., Heterologous expression of endo-beta-1,4-D-glucanase from *Clostridium cellulovorans* in *Clostridium acetobutylicum* ATCC 824 following transformation of the engB gene, 1994, Appl Environ Microbiol. 60:337-40; Handbook on Clostridia, 2005, Peter Durre editor, Taylor & Francis publisher).

The promoter and ribosome binding site (RBS) from the ferredoxin gene (fd) from *Clostridium pasteurianum* ATCC 6013 (GenBank accession number M11214) has been shown to be capable of driving the constitutive expression of heterologous genes to very high levels in multiple *Clostridium* species, including *C. beijerinckii* strain NCIMB 8052; (M C Graves and J C Rabinowitz, 1986, In vive and in vitro transcription of the *Clostridium pasteurianum* ferredoxin gene. Evidence for "extended" promoter elements in gram-positive organisms, J Biol Chem. 1986 261:11409-15; Minton N P, et. al., 1995, Chemotherapeutic tumour targeting using clostridial spores, FEMS Microbiol Rev. 17:357-64; U.S. Pat. No. 6,652,849 (2003)).

To begin, plasmid pMTL500E DNA is linearized with restriction endonuclease XmaI. Alternatively, another restriction site within the multiple cloning site (MCS) of the vector could also be used, provided XmaI in the remainder of the example is also replaced by that restriction enzyme.

A DNA fragment carrying the fd promoter and RBS sequences is prepared by oligonucleotide synthesis using the published DNA sequence for the fd promoter and RBS binding region (GenBank accession number M11214), starting at the 5' end from the first base of the source sequence (-168 relative to the fd gene start codon) but incorporating an XmaI site upstream of that, and replacing the sequence "TTCATG" with "CATATG" (an NdeI site) where "ATG" is the ferredoxin gene start codon, and terminating at the 3' end with any string of non-homologous bases. Alternatively an fd promoter/RBS fragment featuring the same subterminal restriction sites could be prepared by PCR amplification from *Clostridium pasteurianum* ATCC 6013 chromosomal DNA template. The complete adh gene from *C. beijerinckii* strain NCIMB 8052 chromosomal DNA template is amplified by PCR using a forward primer that includes a subterminal NdeI site, wherein the "ATG" of the NdeI site is also the ATG start codon for the adh gene, and where the reverse primer includes a subterminal XmaI site. It should be noted that in this example, and in Example 8 and other examples incorporating this promoter replacement tactic, that there are alternative restriction recognition sites incorporating ATC sequences that could be chosen for the promoter-RBS-gene fusion, for example restriction endonucleases Nb.BsrDI or BsrDI.

The synthesized fd promoter/RBS fragment and the PCR-ed adh gene fragment are purified, then digested with NdeI and ligated together, creating a "fd promoter/RBS/adh gene" fragment having subterminal XmaI sites. This is digested with XmaI and ligated into the linearized pMTL500E plasmid. The reaction products are used to transform *E. coli* DH5alpha. Ampicillin resistant colonies are selected and the transformant colonies are screened by DNA sequencing to confirm the presence of the correct "fd promoter-RBS-adh gene" insert. The new plasmid is purified from the *E. coli* transformant and is used to electroporate *C. beijerinckii* strain NCIMB 8052 or BA101. Erythromycin resistant transformant colonies are recovered as in Example 6.

Alternatively, the plasmid pMTL500F, which already has the fd promoter sequence positioned upstream of an MCS (page 141, Chapter 6, in The Clostridia and Biotechnology, 1993, D. R. Woods editor, Butterworth-Heinemann), could be adapted as the cloning vector for the adh gene provided that the details of the method preserve a functioning RBS for expression of the cloned adh gene.

The resulting strains express adh constitutively due to the use of the heterologous fd promoter, and due to gene amplification on the multicopy vector. The expression of adh in the new strains is confirmed to be constitutive, and is quantitated by enzyme assay. The new strains are tested in fermentations for solvent formation as in Example 1, including the addition of erythromycin to the fermentation medium for every 24 hours of elapsed culture time.

Other promoters for constitutive gene expression are known in the art and would be suitable for use in this example; for instance, the ptb (phophobutyl transferase) gene promoter from *C. acetobutylicum* has been used to drive constitutive expression of the LacI in several *Clostridium* species—sufficient to suppress the fd promoter when under control of the LacZ operator (J T Heap, et. al., 2007, The ClosTron: a universal gene knock-out system for the genus *Clostridium*, J Microbiol Methods 70:452-64). Consequently, if tuning of the level of expression of the adh gene or other cloned genes is required to achieve the best result, other promoters can be tried as a means of achieving that end.

If further tuning of the expression level of the cloned adh is found to be required, the method of cloning the gene is repeated with minor modifications to the DNA sequence of the RBS site, so as to alter the efficiency of ribosome binding and the level of functional gene product in the cell. (See page 167, The Clostridia and Biotechnology, 1993, D. R. Woods editor, Butterworth-Heinemann).

The following shows the DNA sequence in the RBS region of the native fd and adh genes, where the upper-case letters are the start codons of the genes and the Shine-Dalgarno sequences of the RBS region are underlined. Tuning of the expression level of the cloned genes is accomplished by altering either the sequence in the underlined regions, and the spacing between those regions and the ATG start codon.

```
adh
                                    (SEQ ID NO: 20)
ttttaggaggaa atattt ATG

fd
                                    (SEQ ID NO: 21)
tttaaggaggtgtatttttcATG

fd-adh (new)
                                     SEQ ID NO: 22)
tttaaggaggtgtatttcatATG
```

In the general manner of this example, derivatives of *C. beijerinckii* strain NCIMB 8052, or BA101 or other solventogenic *Clostridium* species and strains, are constructed having an increased level of expression, or constitutive expression of other genes and their homologs, for instance the bed, buk, cheA, cheC and cheD genes. In the case of *Clostridium* species having active restriction-modification systems, such as for example *C. acetobutylicum* ATCC 824 and other strains, steps to overcome the transformation barrier imposed by the restriction systems are added to the above protocol as in example 6.

Example 8

Construction of Solventogenic Clostridia Engineered for Constitutive Expression of the Adh Gene in Single Copy Number from a Heterologous Promoter The methods of Example 6 and Example 7 can be combined and modified to achieve constitutive expression of the adh gene, at a level that is lower than expression from a multicopy plasmid. This is achieved by integrating the fd promoter-RBS-adh gene construct into the chromosome of the *Clostridium* host. The expression level of the adh gene may be higher than the untransformed parent strain, or it may be lower than the untransformed parent strain, depending upon the native level of expression of the adh gene in the untransformed strain, and upon modifications to the fd promoter and RBS sequences of the engineered strain.

DNA of plasmid pAK102 DNA is prepared and linearized by digestion with XmaI as in Example 6.

A DNA fragment carrying the fd promoter and RBS sequences, engineered at the ATG start codon to contain an NdeI site, is constructed as in Example 7.

A fragment of the adh gene from *C. beijerinckii* strain NCIMB 8032 (SEQ ID NO:1, Cbei_2181 of GenBank CP000721), consisting of the 5' one-third to one-half of the gene, is generated by PCR amplification from chromosomal DNA, incorporating the 5' NdeI site and 3' XmaI site as in Example 7.

The fd-RBS fragment is ligated to the adh fragment at their NdeI sites, and then the fd-RBS-adh fragment is inserted by ligation into the XmaI site of plasmid pAK102. The new plasmid construct is recovered and verified, and then electroporated into *Clostridium beijerinckii* NCIMB 8052 or BA101 hosts and selected by erythromycin resistance as in Example 6. The resulting erythromycin resistant transformants are single-cross-over products between the cloned adh 5' fragment on the plasmid, and the adh gene on the chromosome. The structure of the expected construct, in order from 5' to 3' of the top strand of the genome sequence, would be as shown below.

5'-partial adh gene-pAK102 vector-fd promoter-RBS-complete adh gene-3'

The erythromycin resistant transformants are checked by DNA sequencing to verify the expected structure.

The isolated new strains are maintained under erythromycin selection to prevent reversion by homologous crossing-out of the plasmid. The strains are assayed for constitutive expression of adh enzyme, and for levels of solvent and acid formation in batch fermentation experiments. Due to its presence in single copy number, the level of expression of adh would be expected to be less than the strains of Example 7. As in example 7, further tuning of cellular levels of the Adh enzyme could be accomplished by varying the constitutive promoter that is used (for example, ptb) or by changing the sequence of the RBS region of the construct.

In the general manner of this example, derivatives of *Clostridium beijerinckii* NCIMB 8052, or BA101 or other solventogenic *Clostridium* species and strains, are constructed having various levels of constitutive expression of other genes and their homologs, for instance the bcd, buk, cheA, cheC and cheD genes. In the case of *Clostridium* species having active restriction-modification systems, such as for example *C. acetobutylicum* ATCC 824 and other strains, steps to overcome the transformation barrier imposed by the restriction systems are added to the above protocol as in example 6.

Example 9

Construction of Solventogenic Clostridia Engineered for Reduced Expression of the sspA Gene Relative to the Untransformed Strain Constitutive expression from the heterologous fd promoter, driving the expression of a single copy of a gene as taught in Example 8, can be modified to adjust the level of expression of the engineered gene. Such modification also could be in the direction of lowered expression relative to the untransformed host. This is advantageous in the instance where reduced gene expression is beneficial to solvent formation, but where complete elimination of gene expression produces undesirable effects.

By introducing changes to the DNA sequence of the fd promoter, the level of transcription of the gene is reduced leading to a reduction in mRNA levels for the gene in the cell and lower levels of functional gene product. By altering the DNA sequence corresponding to the RBS and the spacing between the RBS and the ATG start codon of the gene, the level of translation of the mRNA can be reduced, also leading to accumulation of less functional gene product in the cell. A combination of the mRNA reduction and translation reduction could lead any degree of reduction of gene expression without producing a full "knockout" affect.

DNA of plasmid pAK102 DNA is prepared and linearized by digestion with XmaI as in Example 6.

The 5' one-half of the sspA gene from strain *Clostridium beijerinckii* NCIMB 8052 (SEQ ID NO: 11, Cbei_3080 of GenBank CP000721), is PCR-amplified from chromosomal DNA template, using a primer design that incorporates a 5' NdeI site and a 3' XmaI site as in Example 7. Being that sspA is a short gene (210 bases), if suitable primers cannot be found, then a ClaI restriction site that exists near the middle of the gene is used to cleave the PCR amplification product and the 5' half of the sspA gene is purified from an agarose gel.

A DNA fragment carrying the fd promoter and RBS sequences, engineered at the ATG start codon to contain an NdeI site, is synthesized as in Example 7, including the creation of the 5' XmaI and 3' NdeI sites, except that instead of a single DNA sequence, a collection of oligonucleotide species is produced having various nucleotide base changes in the fd promoter and RBS sites.

The fd promoter of *C. pasteurianum* ATCC 6013 (GenBank M1214) has been characterized. It displays "minus-10" and "minus-35" sequences that are not unlike those described for normal promoters of other gram-positive bacteria (M C Graves and J C Rabinowitz, 1986, J Biol Chem. 1986 261:11409-15; page 287, The Clostridia and Biotechnology, 1993, D. R. Woods editor, Butterworth-Heinemann). In particular, base changes introduced in the regions of minus-75 to minus-67, and minus-57 to minus-46 relative to the ATG start codon of the fd gene could impact promoter strength. Changes made to the RBS site at bases minus-17 to minus-11 alter the efficiency of translation of mRNA to protein. These bases are underlined in the DNA sequence below, which shows the fd promoter and RBS region of the oligonucleotide to be synthesized (the "atg" start codon is shown in lower-case). By introducing one or several different changes in the underlined regions in the sequence of each fd-RBS DNA oligo that is synthesized, a mixture of oligonucleotides bearing different mutations in the region is produced.

```
                                        (SEQ ID NO: 23)
5'_TTTAAAAAGTTTAAAAACATGATACAATAAGTTATGGTAAAC
TTATGATTAAAATTTTAAGGAGGTGTATTTCATatg_3'
```

The mixture of synthesized fd-RBS fragments bearing the different mutations is ligated to the sspA fragment at their NdeI sites, and then the fd-RBS-sspA fragment is ligated into the XmaI site of plasmid pAK102. In the case of using ClaI to generate the sspA fragment, a blunt end ligation is done to close the plasmid. The new plasmid construct is recovered and verified, and then electroporated into *Clostridium beijerinckii* NCIMB 8052 or BA101 hosts and selected by erythromycin resistance as in Example 6. The resulting erythromycin resistant transformants are single-cross-over products between the cloned sspA 5' fragment on the plasmid, and the sspA gene on the chromosome. The isolated new strains are maintained under erythromycin selection to prevent reversion by homologous crossing-out of the plasmid. As alluded to in Example 6, maintenance of the culture using techniques other than spore propagation, such as frozen glycerol stocks of vegetative cells, might be necessary for some isolates.

The total collection of erythromycin-resistant isolates would comprise a collection of strains showing varying levels of expression of the sspA gene. The isolates are screened in fermentations for their ability to produce more solvent or produce solvent more efficiently, or faster, as in Example 6. Candidates that show improved solvent forming properties or other desirable phenotypes are further characterized to determine the location of the inserted DNA in the chromosome, and the extent of expression of the sspA gene at both the transcriptional level (abundance of mRNA) and translational level (abundance of SspA protein), and to characterize the sporulation and morphological properties of the new strains.

In the general manner of this example, derivatives of *Clostridium beijerinckii* NCIMB 8052, or BA101 or other solventogenic *Clostridium* species and strains, are constructed having a reduced level of expression of genes that are targeted for various degrees of reduction; for instance mutants showing reduced expression of spoIVA, spoVB, manIIAB or manIIC genes or their homologs. In the case of *Clostridium* species having active restriction-modification systems, such as for example *C. acetobutylicum* ATCC 824 and other strains, steps to overcome the transformation barrier imposed by the restriction systems are added to the above protocol as in example 6.

Example 10

Construction of Solventogenic Clostridia Engineered for Inducible Expression of the Bed Gene Plasmid pMTL5401F is a *Clostridium/E. coli* shuttle vector designed for inducible expression of cloned genes (JT Heap, et. al., 2007, The ClosTron: a universal gene knock-out system for the genus *Clostridium*, J Microbiol Methods.: 452-64). For the purpose of this example its essential elements are the ferredoxin gene fd promoter fused to the operator of the lacZ operon (the promoter/operator combination is called "fac"), the lacI repressor gene under the control of the *C. acetobutylicum* ptb gene promoter, plasmid replication functions for *E. coli* and *Clostridium* hosts, and ampicillin and erythromycin resistance genes for selection in *E. coli* and *Clostridium* hosts. In this system the LacI gene product represses transcription initiation at the fd promoter due to the close proximity of the lac operator to the fd promoter. In the presence of the lactose analog IPTG (isopropyl-beta-D-thiogalactopyranoside), the Lad repressor fails to bind its operator and the fd promoter can then function. In this system, genes cloned downstream of the plasmid fac promoter/operator are repressed until IPTG is added to the system, at which time the promoter is induced and the gene is expressed.

Plasmid pMTL5401F can be used for the inducible expression of the bed gene (SEQ ID NO:2, Cbei_2035 from GenBank CP000721). To do this a DNA fragment bearing the full-length bcd gene and including about 25 bases upstream of the bcd gene (to include the gene's RBS site, but no more), and having terminating restriction sites to control the length of DNA upstream and downstream of the gene, is prepared by PCR amplification from *C. beijerinckii* strain NCIMB 8052 or strain BA101 chromosomal DNA template. This fragment is then inserted into the linearized pMTL5401F vector so as to bring the bed gene and its RBS under the control of the fac promoter. Plasmid clones having the proper structure are then recovered and confirmed as in Example 7, and are labeled plasmid "pfac-bed."

*C. beijerinckii* strain NCIMB 8052 or BA101 is then transformed with pfac-bcd by electroporation and erythromycin resistant colonies are selected as in the other examples, and are maintained under erythromycin selection. Transformants are verified by DNA sequencing and then tested for levels of bed enzyme expression, and for solvent production in batch fermentations at various timepoints before and after induction of bcd gene expression by addition of IPTG to the culture, IPTG could be tried in the concentration range of 0.5 mM to 2 mM, but higher concentrations could be tried if required.

As an alternative to the LacI/lacZ operator system, other inducible promoter/operator systems for use in *Clostridium* species have also been described and shown to function, for instance the adaptation of the xylose-inducible system from *Staphylococcus xylosus* for use in *C. acetobutylicum* (*L. Girbal*, et. al., 2003, Development of a sensitive gene expression reporter system and an inducible promoter-repressor system for *Clostridium acetobutylicum*, Appl Environ Microbiol.:4985-8). To use this system the xylA promoter-operator sequence is PCR amplified from chromosomal DNA of *S. xylosus* strains DSM 20267. This could be cloned into an appropriate vector, such as pMTL500E, or low-copy number derivatives of the same replicon such as pMTL502E (page 45, Handbook on Clostridia, 2005, Peter Durre editor, Taylor & Francis publisher) and used for xylose-inducible expression of cloned genes for solvent production.

Alternatively, gene expression microarrays could be used to search entire *Clostridium* genomes for promoters matching certain desired expression characteristics, including constitutive promoters, promoters of various strength for low-level, intermediate-level or high-level expression of genes, promoters responding to specific external factors such as chemical compounds that are added or that are present in fermentation substrates, or promoters that follow certain desirable temporal patterns of transcription initiation in the specific fermentation process that is being developed. To accomplish this, high-density microarrays representing entire genomes at high resolution would be prepared; for example arrays supplied by Roche NimbleGen, Inc. could be used. Messenger RNA to be amplified for final interrogation of the arrays would be isolated from cultures of *Clostridium beijerinckii* NCIMB 8052 or BA101, or other *Clostridium* strains, under under multiple different conditions, the exact conditions depending on the promoter-control objectives of the work. A time-course of the culture could be used to discover promoters that show a temporal pattern of activity. Promoters that respond to specific added inducers, for example xylose or arabinose, or furfual or HMF, etc., could be discovered by comparing samples prepared before and after addition of those substances. Constitutive promoters would be those that show relatively little change in activity in time-course experiments or in response to other challenges. The specific promoters of interest would be discovered by the pattern of expression of the genes downstream of the promoters; in other words, one would analyze the microarray data to find specific genes which expression reflects the desired patterns, then clone regions upstream of those genes, or operons in the case of apparent co-transcription of contiguous genes, to discover the exact promoter that displays the wanted characteristics.

In the general manner of this example, derivatives of *C. beijerinckii* strain NCIMB 8052, or BA101 or other solventogenic *Clostridium* species and strains, are constructed having inducible expression of other genes and their homologs, for instance the adh, buk, cheA, cheC and cheD genes. In the case of *Clostridium* species having active restriction-modification systems, such as for example *C. acetobutylicum* ATCC 824 and other strains, steps to overcome the transformation barrier imposed by the restriction systems are added to the above protocol as in example 6.

Example 11

Construction of *E. coli* Strains Engineered to Express the Adh Gene from a Solventogenic *Clostridium*

Strains of *E. coli* are constructed that constitutively express the adh gene of *C. beijerinckii* strain NCIMB 8052 from a strong constitutive promoter. The strains are constructed by insertion of an *E. coli* promoter-*Clostridium* adh gene construct into the lacZ gene in the chromosome of *E. coli*, from a linear DNA fragment, by double crossover recombination into lacZ.

The Ptac and Ptrc promoters are constitutive synthetic promoters that are often used for engineered expression of genes in *E. coli* (Herman A. De Boer, et al., The tac promoter: a functional hybrid derived from the trp and lac promoters. Proc. Natl. Acad. Sci. 1983).

The adh gene (SEQ ID NO: 1, Cbei_2181 of GenBank CP000721) is amplified by PCR using chromosomal DNA from *C. beijerinckii* NCIMB 8052 as template. The forward PCR primer is designed so as to incorporate the Ptac promoter or the Ptrc promoter sequence and the lacZ ribosome binding site, properly positioned in relation to the ATG start codon of the *Clostridium* adh gene to support expression of adh in *E. coli*. The reverse primer is designed with a terminal HindIII restriction site to facilitating its subsequent ligation to a tetracycline resistance gene fragment ($Tet^R$) from pBR322 or a related vector.

A DNA fragment bearing the HindIII site and $Tet^R$ gene and its native promoter is prepared by PCR amplification from a suitable vector, such as pBR322 for example.

The Ptac-adh and $Tet^R$ fragments are ligated together at their HindIII sites, yielding a linear DNA fragment carrying the $Tet^R$ gene and the adh gene, with the genes oriented for divergent transcription. The $Tet^R$-Ptac-adh or $Tet^R$-Ptrc-adh fragment is ligated into a pGEM-T vector (Promega Corporation), disrupting the lacZ sequence of that vector.

Using a Ptac promoter construct as an example, the pGEM-T lacZ::Ptac-adh-$Tet^R$ plasmid is then linearized and electroporated into an *E. coli* recB recC sbcB host, which supports transformation and recombination with linear DNA molecules (Winans, S. C., Elledge, S. J., Krueger, J. H. & Walker, G. C., 1985, *J. Bacteriol.* 161: 1219-1221). A double crossover recombination event between the linearized plasmid and the lacZ gene of the *E. coli* chromosome results in insertional inactivation of the host lacZ gene, and a $Tet^R$ lacZ phenotype for transformants. Stable transformants are selected with tetracycyline, and tested for the lacZ phenotype, and for insertion of the expected structure into the chromosome by DNA sequencing.

In the general manner of this example, other solvent pathway genes from various *Clostridium* species and strains, for instance the bcd, buk, cheA, cheC and cheD genes, could be cloned and expressed in *E. coli* hosts.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A recombinant solventogenic microorganism, wherein the microorganism is transformed with:

(a) a nucleic acid molecule comprising at least one *Clostridium beijerinckii* Adh (alcohol dehydrogenase) polynucleotide comprising a nucleotide sequence having at least 95% sequence identity to the sequence of SEQ ID NO: 14, wherein the polynucleotide encodes a polypeptide having alcohol dehydrogenase activity;

(b) a nucleic acid molecule comprising at least one *Clostridium beijerinckii* Bcd (butyryl-CoA dehydrogenase) polynucleotide comprising a nucleotide sequence having at least 95% sequence identity to the sequence of SEQ ID NO: 2, wherein the polynucleotide encodes a polypeptide having butyryl-CoA dehydrogenase activity; and (c) a nucleic acid molecule comprising at least one *Clostridium beijerinckii* Buk (butyrate kinase) polynucleotide comprising a nucleotide sequence having at least 95% sequence identity to the sequence of SEQ ID NO: 3, wherein the polynucleotide encodes a polypeptide having butyrate kinase activity;

wherein the recombinant solventogenic microorganism is capable of (i) more efficient butanol production, (ii) faster butanol production, and/or (iii) increased butanol production relative to the same recombinant solventogenic microorganism that is not transformed with the nucleic acid molecules of (a), (b), and (c).

2. The recombinant solventogenic microorganism of claim 1, wherein the microorganism is further transformed with a polynucleotide comprising a nucleotide sequence having at least 95% sequence identity to the sequence of SEQ ID NO: 4, 5, 6 or combinations thereof, and wherein the polynucleotide encodes a polypeptide having chemotaxis protein activity.

3. The recombinant solventogenic microorganism of claim 1, wherein expression of the *Clostridium beijerinckii* Adh polynucleotide is controlled by an inducible or a constitutive promoter.

4. The recombinant solventogenic microorganism of claim 1, which is a yeast, bacterium, or fungi.

5. The recombinant solventogenic microorganism of claim 4, wherein the bacterium is an *Escherichia* or a *Clostridium.*

6. The recombinant solventogenic microorganism of claim 4, wherein the bacterium is a *Clostridium beijerinckii* or *Clostridium acetobutylicum.*

7. The recombinant solventogenic microorganism of claim 4, wherein the bacterium is a recombinant *Clostridium beijerinckii* 8052.

8. The recombinant solventogenic microorganism of claim 1, which is cellulolytic.

9. The recombinant solventogenic microorganism of claim 1, wherein the *Clostridium beijernickii* Adh polynucleotide is a heterologous Adh polynucleotide from *Clostridium beijernickii* NCIMB 8052.

10. A method of producing butanol comprising culturing the recombinant solventogenic microorganism of claim 1, such that butanol is produced.

11. A method for making the recombinant solventogenic microorganism of claim 1, comprising transforming a solventogenic microorganism with:

(a) a nucleic acid molecule comprising at least one *Clostridium beijerinckii* Adh polynucleotide comprising a nucleotide sequence having at least 95% sequence identity to the sequence of SEQ ID NO: 14, wherein the polynucleotide encodes a polypeptide having alcohol dehydrogenase activity, (b) a nucleic acid molecule comprising at least one *Clostridium beijerinckii* Bcd polynucleotide comprising a nucleotide sequence having at least 95% sequence identity to the sequence of SEQ ID NO: 2, wherein the polynucleotide encodes a polypeptide having butyryl-CoA dehydrogenase activity, and (c) a nucleic acid molecule comprising at least one *Clostridium beijerinckii* Buk polynucleotide comprising a nucleotide sequence having at least 95% sequence identity to the sequence of SEQ ID NO: 3, wherein the polynucleotide encodes a polypeptide having butyrate kinase activity;

wherein the recombinant solventogenic microorganism is capable of (i) more efficient butanol production, (ii) faster butanol production, and/or (iii) increased butanol production relative to the microorganism prior to the transformation with the nucleic acid molecules of (a), (b), and (c).

12. The method claim 11, wherein, the recombinant solventogenic microorganism is *Clostridium* sp., *Escherichia* sp., *Clostridium beijerinckii, Clostridium beijerinckii* 8052, *Clostridium beijernickii* BA101, or *Clostridium acetobutylicum.*

13. The method of claim 11, wherein the *Clostridium beijerinckii* Adh polynucleotide is operably linked to a promoter.

14. The recombinant solventogenic microorganism of claim 1, wherein the nucleic acid molecule comprising at least one *Clostridium beijerinckii* Adh polynucleotide encodes an alcohol dehydrogenase protein comprising the amino acid sequence of SEQ ID NO: 15.

15. The method of claim 11, wherein the nucleic acid molecule comprising at least one *Clostridium beijerinckii* Adh polynucleotide encodes an alcohol dehydrogenase protein comprising the amino acid sequence of SEQ ID NO: 15.

16. The recombinant solventogenic microorganism of claim 1, which is non-cellulolytic.

* * * * *

SEQUENCE LISTING

```
<160> NUMBER OF SEQ ID NOS: 23

<210> SEQ ID NO 1
<211> LENGTH: 1167
<212> TYPE: DNA
<213> ORGANISM: Clostridium beijerinckii

<400> SEQUENCE: 1

atggcacgtt ttactttacc aagagacatt tatcatggag aaggagcact tgaggcactt     60
```

-continued

```
aaaactttaa aaggtaagaa agctttctta gtagttggtg gcggatcaat gaaaagattt    120
ggatttctta aacaagttga agattattta aaagaagcag gaatggaagt agaattattt    180
gaaggtgttg aaccagatcc atcagtggaa acagtaatga aaggcgcaga agctatgaga    240
aactttgagc ctgattggat agttgcaatg ggtggaggat caccaattga tgctgcaaag    300
gctatgtgga tattctacga atacccagat tttacttttg aacaagcagt tgttccattt    360
ggattaccag accttagaca aaaagctaag tttgtagcta ttccatcaac aagcggtaca    420
gctacagaag ttacagcatt ctcagttatc acaaattatt cagaaaaaat taaatatcct    480
ttagctgatt ttaacataac tccagatata gcaatagttg atccagcact tgctcaaact    540
atgccaaaaa ctttaacagc tcatactgga atggatgcat taactcacgc tatagaagca    600
tacactgcat cacttcaatc aaatttctca gatccattag caattaaagc tgtagaaatg    660
gttcaagaaa atttaatcaa atcatttgaa ggagataaag aagctagaaa tctaatgcat    720
gaagctcaat gtttagctgg aatggcattt tctaatgcat tacttggaat agttcactca    780
atggctcata aggttggtgc tgtattccat attcctcatg gatgtgcaaa tgctatattt    840
ttaccatatg taattgagta taacagaaca aaatgcgaaa atagatatgg agatattgcg    900
agagccttaa aattaaaagg aaacaatgat gccgagttaa ctgattcatt aattgaatta    960
attaatggat taaatgataa gttagagatt cctcactcaa tgaaagagta tggagttact   1020
gaagaagatt ttaaagctaa tctttcattt atcgctcata acgcagtatt agatgcatgc   1080
acaggatcaa atcctagaga aatagatgat gctacaatgg aaaaattatt tgaatgcaca   1140
tactatggaa ctaaagttaa tttgtaa                                       1167
```

<210> SEQ ID NO 2
<211> LENGTH: 1140
<212> TYPE: DNA
<213> ORGANISM: Clostridium beijerinckii

<400> SEQUENCE: 2

```
atgaatttta agttaactag agaacaacaa ttagtacaac aaatggttag agaattcgca     60
gtaaatgaag ttaagccaat agctgccgaa atcgacgaaa cagaaagatt ccctatggaa    120
aacgttgaaa aaatggctaa gcttaaaatg atggggatcc catttttttaa agaatttggt    180
ggagcaggcg gagatgttct ttcatatata attgctgtgg aagaattatc aaaagtttgt    240
ggtactacag gagttattct ttcagcgcat acatcattat gtgcatcagt aattaatgaa    300
aatggaacta acgaacaaag agcaaaatat ttacctgatc tttgcagcgg taaaaagatc    360
ggtgctttcg gattaacaga accaggtgct ggtacagatg ctgcaggaca acaaacaact    420
gctgtattag aaggggacca ttatgtatta aatggttcaa aaatcttcat aacaaatggt    480
ggagttgctg aaactttcat aatatttgct atgacagata agagtcaagg aacaaaagga    540
atttctgcat tcatagtaga aaagttattc ccaggattct caataggaaa attagaaaac    600
aagatgggaa tcagagcatc ttcaactact gagttagtta tggaaaactg catagtacca    660
aaagaaaacc tacttagcaa agaaggtaag ggatttggta tagcaatgaa aactcttgat    720
ggaggaagaa ttggtatagc tgctcaagct ttaggtattg cagaaggagc ttttgaagaa    780
gctgttaact atatgaaaga aagaaaacaa tttggtaaac cattatcagc attccaagga    840
ttacaatggt atatagctga aatggatgtt aaaatccaag ctgctaaata cttagtatac    900
ctagctgcaa caaagaagca agctggtgag ccttactcag tggatgctgc aagagctaaa    960
ttatttgctg cagatgttgc aatggaagtt acaactaagg cagttcaaat ctttggtgga   1020
```

| | |
|---|---|
| tatggttaca ctaaagaata cccagtagaa agaatgatga gagatgctaa aatatgcgaa | 1080 |
| atctacgaag gaacttcaga agttcaaaag atggttatcg caggaagcat tttaagatag | 1140 |

<210> SEQ ID NO 3
<211> LENGTH: 1068
<212> TYPE: DNA
<213> ORGANISM: Clostridium beijerinckii

<400> SEQUENCE: 3

```
atgtcatata agctattaat aatcaatcca ggttcaacat caacaaagat tggtgtttac     60
gaaggagaaa aggaactatt tgaagaaact ttgagacaca caaatgaaga aataaagaga    120
tatgatacaa tatatgatca atttgaattt agaaaagaag ttatattaaa tgttcttaaa    180
gaaaagaatt ttgatataaa gactctaagt gctattgttg gtagaggtgg aatgcttaga    240
ccagttgaag gtggaacata tgcagtaaat gatgcaatgg ttgaagattt aaaagttgga    300
gttcaaggac ctcatgcttc taaccttggc ggaataattg ccaagtcaat tggagatgaa    360
ttaaatattc catcatttat agtagatcca gttgttacag atgagttagc agatgtagca    420
agactatctg gagtaccaga actaccaaga aaaagtaaat tccatgcttt aaatcaaaaa    480
gcggtagcta aaagatatgg aaaagaaagt ggacaaggat atgaaaacct aaatcttgta    540
gttgtacata tgggtggagg cgtttcagtt ggtgctcaca atcatgggaa agttgtcgat    600
gtaaataatg cattagatgg agatggccca ttctcaccag aaagagctgg atcagttcca    660
attggtgatt tagttaaaat gtgttttagt ggaaaatata gtgaagcaga agtatatggc    720
aaggctgtag gaaaaggtgg atttgttggt tatctaaaca caaatgatgt aaaaggtgtt    780
attgataaga tggaagaagg agataaagaa tgtgaatcaa tatacaaagc atttgtttat    840
caaatttcaa aagcaatcgg agaaatgtca gttgtattag aaggtaaagt tgatcaaatt    900
atttttaccg gaggaattgc atactcacca acacttgttc cagaccttaa agcaaaagtt    960
gaatggatag ccccagttac agtttatcct ggagaagatg aattacttgc tctagctcaa   1020
ggtgctataa gagtacttga tggagaagaa caagctaagg tttactag                1068
```

<210> SEQ ID NO 4
<211> LENGTH: 2121
<212> TYPE: DNA
<213> ORGANISM: Clostridium beijerinckii

<400> SEQUENCE: 4

```
atggatttga aaaagcatca acctttattt ataaaaagat atagaggagg agtaaggatg     60
gatacatctc aatatatgtc aatgttttta gaggagtcat tggaaaattt acaaacattg    120
aacgaatcat tattagattt agagcaaaat ccagatgata cagataaggt taatgaaata    180
tttagagttg cccacacaat taaggggatg gcagcgacta tgggatttac tgatttagca    240
gaacttaccc ataagatgga agatgtatta gctgaattta gagaaggaaa actaaaagta    300
actcaggatg tagtaacagt attatttgat tgccttgata cattagaaaa gatggttgat    360
aacgttcaag aaggttctga ggaaaaaata gatatagatg gaataatgaa agccttagct    420
gatataaaag aaaatggaaa caatagtaac acacaagaag aaacacaaga tagtgaaatc    480
aagtcagaag aaggaagaaa aatgatatca ggtgatgaat ttgatttaga tttaaatcaa    540
tatgacacgt ctgttattag acaagctaga gaaaaaggtt ttaactctat tgaattaaaa    600
gtaacattaa gtgaaaatac tttgttaaaa tcagcaagag cctttttaat agttaaagat    660
```

-continued

```
cttgaagatc acggagaaat actaaaatca gacccatcaa ctcaagaaat tgaaaatgaa    720

gagtttgatt ttgagttgaa atttgtatta gtaactaaaa atactgtaga tgaaatatta    780

actgttgtaa atggaatttc agaagttgca aaagttgaag cttctttaat agaattagaa    840

agcccagata tagctccaaa agaagcagaa gtaaaagaag tgccacaggt accagctata    900

gaaaaagctt caggagaaaa gccggctgaa gcaaaagttg agacaaagca accagttgct    960

aaaaagccta ctcaaaagaa agaagttaag aaggcacatc aatcagtaag agttgattta   1020

gagagaatag ataatttaat gaatatggtt tctgagcttg taatttatag aactcgatta   1080

gaacaaatcg taaatgttca taaatctcaa gagttaaatg aaacattgga acaagtagga   1140

aggacaacat ctgatcttca agatttagtc atgaagatta gaatgcttcc gctagataca   1200

gtattcaata gattcccaag aatgataagg gatatatcag tagagttaaa taaggaaatt   1260

aactttgtta tagaaggtgc tgatactgaa cttgatagaa ctgttattga tgaaataggt   1320

gaaccattaa tacatttatt aagaaatgca gcggatcatg ggatagaatc tgctgaaaag   1380

agaattgcac aaggcaagcc tccagttgga actgtgaagc ttattgcata ccaagaagga   1440

acaaaaagcat taataaaagt atcagatgat ggagcaggaa taaatcttga aagagtaaaa   1500

gctaaggcag agcaaaaagg aataaacaca gaaggattgt cagatagtga tattaagaat   1560

ttgatttttg ctcaaggatt tagcactaat gaagttgtaa cagatatctc aggaagagga   1620

gttggaatgg atgttgttaa gacaaaaatt gcagcactcg gtggtactgt agatctacta   1680

agtgaagaag gcaaaggctc aacttttgta attaagcttc cacttacatt acaaataata   1740

caagctttac ttgtaaaagt aggagaggaa acattagcaa tatcattagg atttattgat   1800

agagtaattg actataaaga ggaaaatata aagaagagta atggaaaaga agttattatt   1860

tatagagaaa atgtaattcc attagtaaga ttaaatgaaa ctttagatat agaggctagt   1920

aatactgata agaaatttgt tataatagtt aatgtaggtg ataaaactat aggtttatta   1980

gtcgattcat tacttggaca acaagaaata gttataaagc cactcggaaa aacattaaag   2040

aatttagatc agtatattgg tgcgactata cttggtaatg gtttagtaac gctgatacta   2100

gatgtagggg cattattata a                                              2121
```

<210> SEQ ID NO 5
<211> LENGTH: 603
<212> TYPE: DNA
<213> ORGANISM: Clostridium beijerinckii

<400> SEQUENCE: 5

```
gtggagtatt ctaatttaag cactttgcaa ttagatgcac ttaaagaagt ttctaacata     60

ggtgcaggta atgcagcaac tgctctttct atgatgatgg gaaaaaaagt agatatgaca    120

gtaccagcag taaatgtagt aaaactagaa gaagtatttc aagaaagtgg agaatgtgct    180

gtagctggaa cagttgtaag agtgctgggc gatatttcag gaaatatgct tttagtattc    240

gaacaggaaa cagctgaaaa tgtaataaaa aaattagttg gaagcaagca gtctccagaa    300

agtgaaatgg gaagttctgt attatgcgag atagcaaata taatatcagc atcatatatg    360

aatgctattg cacagttaac taatcttgtt atggcaccat cagtgcctgc aacttcattt    420

gatatgttag gtgcaatact cacaactaca tttattgagt ccaatcaata tgatgaatat    480

atactagata ttgaaactgt attcttagac agtgatacag aagagaatat aggaggacat    540

ttttattata tccctatgcc gggttcgtta gagaaaatat tgaaatctat aggaataaat    600

taa                                                                  603
```

<210> SEQ ID NO 6
<211> LENGTH: 489
<212> TYPE: DNA
<213> ORGANISM: Clostridium beijerinckii

<400> SEQUENCE: 6

```
atgataagtg cagaagtaaa agtagggata gctgatctaa atttagtgct agatccagga     60
ataataatga caataggact agggtcatgt ataggaattg ccttatatga taagataagt    120
aaggtggcag ggttagcaca cataatgctt cctgatagta cacaatttaa aagtagtgca    180
aaccccatga aatttgcaga tttagctatt ccaatattaa ttgataaaat ggaaaagcaa    240
gggtgtaaaa agagaaatct cgtggctaaa atagctggag gagcttcgat gtttaatttt    300
tctgataaga gcataataag tgatattgga aaaaggaata gtgatgcagt gaagaaaagg    360
ttaaaagaag agtcaattcc tataattgct gaagagatag gtggaaataa aggtagaact    420
atgatccttt acgctagcga tggaaaagta atacttaaag ttgtagggca tggaattgta    480
gaattgtag                                                             489
```

<210> SEQ ID NO 7
<211> LENGTH: 978
<212> TYPE: DNA
<213> ORGANISM: Clostridium beijerinckii

<400> SEQUENCE: 7

```
atggtaggaa ttattcttgc tagtcacgga gaatttgcta aaggcatcat gcaatctggt     60
gcgatgattt tcggagaaca agaaaacgta aaagctgtta cgttgatgcc tagcgaagga    120
cctgatgatc ttagagcaaa aatgaaagat gcaatcgcat cctttgacaa ccaagatgag    180
gttttattct tagttgatct ttggggtggt acaccattca accaagcgaa tatgctattt    240
gaagaacata aagataaatg ggcaatcgta gctggtttga atttaccaat gctgattgaa    300
acttatggtg cacgtctttc aatggaatct gctcatgaaa ttgcagctta tatcttaaat    360
gcaggtaaag aaggagttaa agttaaaccc gaggagttag aaccagcaga tactggtaat    420
gcttcaggag cgggagcagg gcaatctaat gcaggtgcac ctggatcgtt tgaatacgtt    480
ttagctcgta tcgactctcg tttacttcat ggtcaagtag caactgcttg gacaaaaact    540
gtaaatccta cacgaattat tgtcgtgtca gatgatgtag ctagagatac tcttcgtaag    600
aatttgatta cgcaagcttc tcctccgggg gttaaggctc atgttgttcc agttgatcat    660
atgattaaac ttgcaaaaga tgataagcat tttggaggcc aacgtgcaat gcttcttttt    720
gaaaatccaa aagatgtgct tagagctgta gaagggggaa taccgctaaa gataatcaat    780
gttggttcaa tggctcattc tccaggtaag gttcaaccaa gcaaagtttt agctttcaat    840
caagaagata ttgatatatt caataagctt aaacaagctg gacttacttt tgatgtgcgt    900
aaagtaccaa atgattcaaa agcaaatatg gacgaaatac ttaaaaaagc acaagaagaa    960
ttaaaaaaat taaaataa                                                   978
```

<210> SEQ ID NO 8
<211> LENGTH: 807
<212> TYPE: DNA
<213> ORGANISM: Clostridium beijerinckii

<400> SEQUENCE: 8

```
atgactttaa atatagttca aattatatta gtcattttaa tagcattttt agctggtgta     60
```

```
gaaggtatct tagatgaatt ccaatttcac caaccgataa ttgcttgtac attaattggc    120

ttggttacag gtaatttact accatgctta atcttaggtg gtactcttca aatgatagcc    180

ttaggttggg caaatattgg tgctgctgta gcacctgatg cagcattagc cgctgttgca    240

tctgcaatta ttttagttct tggaggtcaa ggtgaagcag gagttgcttc agcaatcgct    300

attgctgttc ctttagcagt tgcaggatta ttattaacaa ttatttgtcg tacacttgct    360

acagcgttcg tacattttat ggatgctgct gctaaagaag gaaatcttag agctattgat    420

atgtggcaaa tcgctgctat ttgtctacaa ggtatacgta ttgcgattcc agcagcacta    480

gtattagcaa tcggtgcagg tcctattagt tcattacttg ctgctatgcc tacttggtta    540

actggtggtt tagcaattgg tggtggaatg gttgtagctg ttggttatgc aatggtaatc    600

aacatgatgg ctacaaaaga agtatggcca ttcttcgcaa ttggttttgt attagcaact    660

gtttcacaaa ttacacttat cggacttggt gcaataggtg tagctttagc acttctttac    720

ttagcactta gcaaacaagg tggctcaggt aatggtggaa attcaaatac tggtgatcct    780

ttaggggatc taatagatag atactaa                                        807
```

<210> SEQ ID NO 9
<211> LENGTH: 1494
<212> TYPE: DNA
<213> ORGANISM: Clostridium beijerinckii

<400> SEQUENCE: 9

```
atgggaggga aaaatgtgga caattttaac atatacaaag atatagccga tagaacccaa     60

ggggacatat atgtaggagt cgtaggacca gttaggacag ggaaatctac atttattaaa    120

aagttcatgg atcttatggt aatacctaaa attgataata cttataaaaa ggaaagagca    180

aaagatgagt taccacagag tggctcagga aaaaatattc acacaacaga acctaaattt    240

gtacctaatg aagcagtaga aataaattta ggggatgaaa taaaatttaa agtaaggatg    300

gttgactgcg taggatatat tgtaaaagga gcattaggat atctagatgg tgaggaaact    360

aaaatggttc atacaccatg gtatgattac gaaatacctt ttgaggatgc agcagaaatt    420

gggacaagaa aagttataaa agaccattca acaataggat tagtaattac aactgatgga    480

agtataactg gaatagatag aaatgactat gtagaaccag aagaaagagt aatatatgaa    540

ttacagtcac taaataaacc atttattgta gttcttaata ctaataagcc taattctcaa    600

gaaactaagg cattgaaaaa agaattagaa gataaatata atgtaactgt tcaagttatg    660

gatgtttata atatggaaga acaagatatt gaggatttat ttaaacacgt acttaaggaa    720

ttccctgtaa aagaaataaa tattgatatg cctgaatggt tagaaaaatt ggaatgtaac    780

cattggctaa aaaaagattt tttcaacata attatgaaca tgagtcaaga tgtctctaag    840

gtaagagaca taaaatactg cttaaatgat tttgaaaatg aagactttat gggaaaggca    900

accataaatg aagttgattt gggtagtgga acagcaaaaa tatctatgaa acctaaggat    960

ggaattttct ataaggttct tagtgagata tgtaatttag aagttggttc agaaagtgac   1020

ttgctcagca taataaatga cctaagtcat gcaaaatgtg aatatgataa ggttaaagat   1080

gcattggaag atgtaagaga gagcggctat ggattggttg caccacaact ttcggaaatg   1140

aagtttgagg agcctgaaat agttaaacaa ggtaataaat atggagttaa attaaaggca   1200

agtgctccaa gcttacatct tataaagtgt gatattaaaa ctgagataag ccctataatg   1260

ggatcagaaa aggaatcgga agaactagta aaaggccttc tagaacaatt tgaaacagat   1320

ccagcccttc tttggcaaag taatatgttt ggaaaatctt tagaagtgtt agtaaaagaa   1380
```

ggattacaaa acaagctata taaaatgcca gaagatgttc aagttaagat tcaaaagact 1440
ttgcagaaaa ttattaatga aggtaatggt ggattaatct gtataatact ttaa 1494

<210> SEQ ID NO 10
<211> LENGTH: 1536
<212> TYPE: DNA
<213> ORGANISM: Clostridium beijerinckii

<400> SEQUENCE: 10
atgaaaaaac aatccctaat aagagggagc ataattcttg gagttgcagg aatattaaca 60
agatttttag gtctattctt tagatggcca ctaataatgt taattggaga tgagggaatt 120
ggatattatc aaatgtcata cccgctatat atgtttttta tagctatggc ttctggagtt 180
ccagttgcaa tttctaagat gatatcagaa aagaatgcaa caaatgatat atatggaagc 240
tttgaagtaa tgaaagaatc tgctatttta atgacaataa tagggacagg cacaacttta 300
gcattattct tttttgcaaa accaatagta ttatttttga agtgggatcc aaaagcgtat 360
tattcattaa tcggaatatc atttgcacca attgtaatat catttgtaac tatatttaga 420
ggattctttc aagggttaca aaatatgact ccgtcagcta tatcacagat aatagagcag 480
attggtagag tcatattcgg tgttggactt gctgtatttt tactacctag aggcatagag 540
tactcagcag gtggtgcagc atttggagca actgcgggag ctgttcttgg aggagcttat 600
ttatactcga attataaaag agtaaagaaa cgttatgcca ttaaaaaaat aaaaagcaat 660
ccagaaatat taaatactat attaaagatt gcaataccaa tatcattagg tactacagta 720
tcaagtatta tgaatttaat agattccatt ttagtaccac aaaaactatt agatgcggga 780
ttcacaaatg tacaatcaac tgtattatat gcgcaattaa caggtaaagc gtctgtaatt 840
gtaaatattc cattaactct ttctatggct atttgtacat ctctaattcc tatcatagct 900
gagaatttca tacttaagaa acagaaagag ctaaaaagta aaatagatgc atctatgaaa 960
atggcatcag taattgctat tccgtgcact tttgggttat tctttttagc tgaaccagta 1020
atgaagttta tatttccagg caggtttgaa ggaatagaga tattaaaata tttatcatta 1080
acaattcctt ttataataat tactcaaaca acaacagcaa tactacaagg aacagggcat 1140
tatataaaac ctgttattaa cctcttgatt gggtgtttga ttaaaattgt attaacgtgg 1200
gtattagttc ctatgcaaat gtttaacata tatggtgctg ttttggcgag ctttggagct 1260
tatttaacag taagtatttt aaatatagtg atgatgaaat ttacactaag agtaagactt 1320
aatttatacg aaatattaat aaaaccttgc tatgcatcca gtattatgat gttaattgta 1380
ttaataagtt ataatatttt atataagaat acaattagta atggaatatc ttgcttgaca 1440
tctatatttt tgggtatgat agtatatatt ataatgataa ttgtattcaa ggtatttaat 1500
gttgaagaaa taagagatag atttaaaaga aagtaa 1536

<210> SEQ ID NO 11
<211> LENGTH: 219
<212> TYPE: DNA
<213> ORGANISM: Clostridium beijerinckii

<400> SEQUENCE: 11
ttgatgtata tgtcatcaaa taacagtgga agaaatagaa cattagtacc agaagcaaag 60
gcaggattaa acagattaaa aactgaggtt gcttcagaag ttggattaag tgattatgaa 120
aacatcgata aaggaagcct ttcttcaaga caaaatggat atgttggcgg ttatatggta 180

-continued

```
aaacatatga ttcaagatta cgaacaaggt cttaagtaa                          219


<210> SEQ ID NO 12
<211> LENGTH: 1140
<212> TYPE: DNA
<213> ORGANISM: Clostridium beijerinckii

<400> SEQUENCE: 12

atgaatttcc aattaactag agaacaacaa ttagtacaac aaatggttag agaattcgca     60

gtaaatgaag ttaagccaat agctgctgaa atcgacgaat cagaaagatt ccctatggaa    120

aacgttgaaa aaatggctaa gcttaaaatg atgggtatcc cattttctaa agaatttggt    180

ggagcaggcg gagatgttct ttcatatata atatctgtgg aagaattatc aaaagtttgt    240

ggtactacag gagttattct ttcagcgcat acatcattat gtgcatcagt aattaatgaa    300

aatggaacta acgaacaaag agcaaaatat ttgccagatc tttgtagtgg taagaaaatc    360

ggtgctttcg gattaacaga accaggcgct ggtacagatg ctgcaggaca acaaacaact    420

gctgtattag aaggagacca ttatgtatta aatggttcaa aaatcttcat aacaaatggt    480

ggagttgctg aaactttcat aatatttgct atgacagata agagtcaagg aacaaaagga    540

atttctgcat tcatagtaga aaagtcattc ccaggattct caataggaaa attagaaaac    600

aagatgggga tcagagcatc ttcaactact gagttagtta tggaaaactg tatagtacca    660

aaagaaaacc tacttagcaa agaaggtaag ggatttggta tagcaatgaa aactcttgat    720

ggaggaagaa ttggtatagc tgctcaagct ttaggtattg cagaaggagc ttttgaagaa    780

gctgttaact atatgaaaga aagaaaacaa tttggtaaac cattatcagc attccaagga    840

ttacaatggt atatagctga aatggatgtt aaaatccaag ctgctaaata cttagtatac    900

ctagctgcaa caaagaagca agctggtgag ccttactcag tggatgctgc aagagctaaa    960

ttatttgcgg cagatgttgc aatggaagtt acaactaaag cagttcaaat ctttggtgga   1020

tatggttaca ctaaggaata cccagtagaa agaatgatga gagatgctaa aatatgcgaa   1080

atctacgaag gaacttcaga agttcaaaag atggttatcg caggaagcat tttaagatag   1140


<210> SEQ ID NO 13
<211> LENGTH: 388
<212> TYPE: PRT
<213> ORGANISM: Clostridium beijerinckii

<400> SEQUENCE: 13

Met Ala Arg Phe Thr Leu Pro Arg Asp Leu Tyr His Gly Glu Gly Ala
 1               5                  10                  15

Leu Glu Val Leu Lys Thr Leu Lys Gly Lys Lys Ala Phe Val Val Val
            20                  25                  30

Gly Gly Gly Ser Met Lys Arg Phe Gly Phe Leu Lys Gln Val Glu Asp
        35                  40                  45

Tyr Leu Thr Glu Ala Gly Met Glu Val Glu Leu Phe Glu Gly Val Glu
    50                  55                  60

Pro Asp Pro Ser Val Glu Thr Val Met Lys Gly Ala Glu Ala Met Arg
 65                  70                  75                  80

Asn Phe Glu Pro Asp Trp Ile Val Ala Met Gly Gly Gly Ser Pro Ile
                85                  90                  95

Asp Ala Ala Lys Ala Met Trp Ile Phe Tyr Glu Tyr Pro Asp Phe Thr
            100                 105                 110

Phe Glu Gln Ala Val Val Pro Phe Gly Leu Pro Glu Leu Arg Gln Lys
        115                 120                 125
```

```
Ala Lys Phe Val Ala Ile Pro Ser Thr Ser Gly Thr Ala Thr Glu Val
    130                 135                 140

Thr Ala Phe Ser Val Ile Thr Asn Tyr Thr Glu Lys Ile Lys Tyr Pro
145                 150                 155                 160

Leu Ala Asp Phe Asn Ile Thr Pro Asp Ile Ala Ile Val Asp Pro Val
                165                 170                 175

Leu Ala Gln Thr Met Pro Lys Thr Leu Thr Ala His Thr Gly Met Asp
            180                 185                 190

Ala Leu Thr His Ala Ile Glu Ala Tyr Thr Ala Ser Leu Arg Ser Asn
        195                 200                 205

Phe Ser Asp Pro Leu Ala Ile Lys Ala Leu Gln Met Val Gln Glu Asn
    210                 215                 220

Leu Ile Lys Ser Phe Glu Gly Asp Lys Glu Ala Arg Asn Leu Met His
225                 230                 235                 240

Glu Ala Gln Cys Leu Ala Gly Met Ala Phe Ser Asn Ala Leu Leu Gly
                245                 250                 255

Ile Val His Ser Met Ala His Lys Val Gly Ala Val Phe His Ile Pro
            260                 265                 270

His Gly Cys Ala Asn Ala Ile Phe Leu Pro Tyr Val Ile Gln Tyr Asn
        275                 280                 285

Arg Thr Lys Cys Glu Asp Arg Tyr Ala Asp Ile Ala Arg Ala Leu Lys
    290                 295                 300

Leu Glu Gly Asn Thr Asp Ser Glu Leu Thr Asp Ser Leu Ile Gly Met
305                 310                 315                 320

Ile Asn Lys Met Asn Ser Asp Leu Asn Ile Pro His Ser Met Lys Glu
                325                 330                 335

Tyr Gly Val Thr Glu Glu Asp Phe Lys Ala Asn Leu Ser Phe Ile Ala
            340                 345                 350

His Asn Ala Val Leu Asp Ala Cys Thr Gly Ser Asn Pro Arg Glu Ile
        355                 360                 365

Asp Asp Ala Thr Met Glu Lys Leu Phe Glu Cys Thr Tyr Tyr Gly Thr
    370                 375                 380

Lys Val Glu Leu
385
```

<210> SEQ ID NO 14
<211> LENGTH: 1167
<212> TYPE: DNA
<213> ORGANISM: Clostridium beijerinckii

<400> SEQUENCE: 14

```
atggcacgtt ttactttacc tagggacttg tatcatggag aaggggcact tgaagtactt      60

aaaactttaa aaggcaaaaa agcttttgta gttgttggtg gaggatcaat gaaaagattt     120

ggttttctta aacaagttga agattattta acagaagcag gaatggaagt agaactattt     180

gaaggagtag aaccagatcc atcagtagaa acagtaatga agggtgccga agcaatgaga     240

aacttcgagc ctgattggat agttgctatg ggtggaggat caccaataga tgctgcaaaa     300

gctatgtgga tattctatga atacccagat tttacttttg aacaagctgt tgttccattt     360

ggtttaccag agcttagaca aaaagctaaa tttgtagcta ttccatcaac aagtggtaca     420

gctacagaag ttacagcttt ttcagttata acaaattaca cagaaaagat taaatatcct     480

ttagctgatt ttaacataac tccagatata gcaatagttg atccagtatt agctcaaact     540

atgccaaaaa cattaacagc tcatactgga atggatgcac taactcatgc tatagaagca     600
```

-continued

```
tatactgcat cgcttagatc aaatttttct gatcctttag caattaaggc attgcaaatg    660

gtacaagaaa atttaatcaa gtcttttgaa ggagacaagg aagctagaaa tctaatgcat    720

gaagctcaat gtttagcagg aatggcattt tctaatgcat tacttggaat agttcattca    780

atggctcaca aggttggtgc tgtattccat attcctcatg gatgtgcgaa tgctatattc    840

ttaccatatg taattcaata taatagaaca aaatgcgaag atagatatgc tgatattgct    900

agagcattaa aattagaagg aaacacagat tcagaattaa ctgattcatt aattggaatg    960

attaataaaa tgaatagtga tttaaatatt cctcattcaa tgaaagaata tggagttact   1020

gaagaagatt ttaaagcaaa tctttcattc attgctcata atgcagtgtt agatgcatgt   1080

acaggatcaa atcctagaga aatagatgat gcgacaatgg aaaaactatt tgaatgcaca   1140

tattatggga caaaggttga actatag                                        1167
```

<210> SEQ ID NO 15
<211> LENGTH: 388
<212> TYPE: PRT
<213> ORGANISM: Clostridium beijerinckii

<400> SEQUENCE: 15

```
Met Ala Arg Phe Thr Leu Pro Arg Asp Leu Tyr His Gly Glu Gly Ala
 1               5                  10                  15

Leu Glu Val Leu Lys Thr Leu Lys Gly Lys Lys Ala Phe Val Val Val
            20                  25                  30

Gly Gly Gly Ser Met Lys Arg Phe Gly Phe Leu Lys Gln Val Glu Asp
        35                  40                  45

Tyr Leu Thr Glu Ala Gly Met Glu Val Glu Leu Phe Glu Gly Val Glu
    50                  55                  60

Pro Asp Pro Ser Val Glu Thr Val Met Lys Gly Ala Glu Ala Met Arg
 65                  70                  75                  80

Asn Phe Glu Pro Asp Trp Ile Val Ala Met Gly Gly Gly Ser Pro Ile
                85                  90                  95

Asp Ala Ala Lys Ala Met Trp Ile Phe Tyr Glu Tyr Pro Asp Phe Thr
            100                 105                 110

Phe Glu Gln Ala Val Val Pro Phe Gly Leu Pro Glu Leu Arg Gln Lys
        115                 120                 125

Ala Lys Phe Val Ala Ile Pro Ser Thr Ser Gly Thr Ala Thr Glu Val
    130                 135                 140

Thr Ala Phe Ser Val Ile Thr Asn Tyr Thr Glu Lys Ile Lys Tyr Pro
145                 150                 155                 160

Leu Ala Asp Phe Asn Ile Thr Pro Asp Ile Ala Ile Val Asp Pro Val
                165                 170                 175

Leu Ala Gln Thr Met Pro Lys Thr Leu Thr Ala His Thr Gly Met Asp
            180                 185                 190

Ala Leu Thr His Ala Ile Glu Ala Tyr Thr Ala Ser Leu Arg Ser Asn
        195                 200                 205

Phe Ser Asp Pro Leu Ala Ile Lys Ala Leu Gln Met Val Gln Glu Asn
    210                 215                 220

Leu Ile Lys Ser Phe Glu Gly Asp Lys Glu Ala Arg Asn Leu Met His
225                 230                 235                 240

Glu Ala Gln Cys Leu Ala Gly Met Ala Phe Ser Asn Ala Leu Leu Gly
                245                 250                 255

Ile Val His Ser Met Ala His Lys Val Gly Ala Val Phe His Ile Pro
            260                 265                 270
```

His Gly Cys Ala Asn Ala Ile Phe Leu Pro Tyr Val Ile Gln Tyr Asn
        275                 280                 285

Arg Thr Lys Cys Glu Asp Arg Tyr Ala Asp Ile Ala Arg Ala Leu Lys
    290                 295                 300

Leu Glu Gly Asn Thr Asp Ser Glu Leu Thr Asp Ser Leu Ile Gly Met
305                 310                 315                 320

Ile Asn Lys Met Asn Ser Asp Leu Asn Ile Pro His Ser Met Lys Glu
                325                 330                 335

Tyr Gly Val Thr Glu Glu Asp Phe Lys Ala Asn Leu Ser Phe Ile Ala
            340                 345                 350

His Asn Ala Val Leu Asp Ala Cys Thr Gly Ser Asn Pro Arg Glu Ile
        355                 360                 365

Asp Asp Ala Thr Met Glu Lys Leu Phe Glu Cys Thr Tyr Tyr Gly Thr
    370                 375                 380

Lys Val Glu Leu
385

<210> SEQ ID NO 16
<211> LENGTH: 216
<212> TYPE: DNA
<213> ORGANISM: Clostridium beijerinckii

<400> SEQUENCE: 16
atgcatatgt catcaaataa tagtggaaga aatagaacat tagtaccaga agcaaaacaa 60
ggattaaaca gattaaaaac tgaggttgct tcagaagttg gattaagcaa ttatgaaagc 120
atggataaag gaaacctttc ttcaagacaa aatggatatg ttggcggata tatggtaaaa 180
catatgatcg aagattatga acaaggtctt aagtaa 216

<210> SEQ ID NO 17
<211> LENGTH: 71
<212> TYPE: PRT
<213> ORGANISM: Clostridium beijerinckii

<400> SEQUENCE: 17

Met His Met Ser Ser Asn Asn Ser Gly Arg Asn Arg Thr Leu Val Pro
1               5                   10                  15

Glu Ala Lys Gln Gly Leu Asn Arg Leu Lys Thr Glu Val Ala Ser Glu
            20                  25                  30

Val Gly Leu Ser Asn Tyr Glu Ser Met Asp Lys Gly Asn Leu Ser Ser
        35                  40                  45

Arg Gln Asn Gly Tyr Val Gly Gly Tyr Met Val Lys His Met Ile Glu
    50                  55                  60

Asp Tyr Glu Gln Gly Leu Lys
65                  70

<210> SEQ ID NO 18
<211> LENGTH: 210
<212> TYPE: DNA
<213> ORGANISM: Clostridium beijerinckii

<400> SEQUENCE: 18
atgtcatcaa ataatagtgg aagaaacaga acattagtac cagaagcaaa acaaggatta 60
aacagattaa aaactgaggt tgcttcagaa gtaggattac atgattacga aaatcaagat 120
aaaggaaatt tatcttcaag acaaaatgga tacgttggcg gatacatggt taagcacatg 180
attgaaagct acgaacaagg tttaaagtaa 210

-continued

<210> SEQ ID NO 19
<211> LENGTH: 69
<212> TYPE: PRT
<213> ORGANISM: Clostridium beijerinckii

<400> SEQUENCE: 19

```
Met Ser Ser Asn Asn Ser Gly Arg Asn Arg Thr Leu Val Pro Glu Ala
 1               5                  10                  15

Lys Gln Gly Leu Asn Arg Leu Lys Thr Glu Val Ala Ser Glu Val Gly
            20                  25                  30

Leu His Asp Tyr Glu Asn Gln Asp Lys Gly Asn Leu Ser Ser Arg Gln
        35                  40                  45

Asn Gly Tyr Val Gly Gly Tyr Met Val Lys His Met Ile Glu Ser Tyr
    50                  55                  60

Glu Gln Gly Leu Lys
 65
```

<210> SEQ ID NO 20
<211> LENGTH: 21
<212> TYPE: DNA
<213> ORGANISM: Clostridium beijerinckii

<400> SEQUENCE: 20
ttttaggagg aaatatttat g 21

<210> SEQ ID NO 21
<211> LENGTH: 23
<212> TYPE: DNA
<213> ORGANISM: Clostridium beijerinckii

<400> SEQUENCE: 21
tttaaggagg tgtatttttc atg 23

<210> SEQ ID NO 22
<211> LENGTH: 23
<212> TYPE: DNA
<213> ORGANISM: Artificial Sequence
<220> FEATURE:
<223> OTHER INFORMATION: Synthetic construct

<400> SEQUENCE: 22
tttaaggagg tgtatttcat atg 23

<210> SEQ ID NO 23
<211> LENGTH: 78
<212> TYPE: DNA
<213> ORGANISM: Clostridium pasteurianum

<400> SEQUENCE: 23
tttaaaaagt ttaaaaacat gatacaataa gttatggtaa acttatgatt aaaattttaa 60
ggaggtgtat ttcatatg 78